United States Patent [19]

Hamann et al.

[11] Patent Number: 5,877,296
[45] Date of Patent: Mar. 2, 1999

[54] PROCESS FOR PREPARING CONJUGATES OF METHYLTRITHIO ANTITUMOR AGENTS

[75] Inventors: Philip Ross Hamann, Garnerville; Lois Hinman, N. Tarrytown; Irwin Hollander, Monsey, all of N.Y.; Ryan Holcomb, Glen Rock, N.J.; William Hallett; Hwei-Ru Tsou, both of New City, N.Y.; Martin J. Weiss, Ft. Lee, N.J.

[73] Assignee: American Cyanamid Company, Madison, N.J.

[21] Appl. No.: 452,164

[22] Filed: May 26, 1995

Related U.S. Application Data

[62] Division of Ser. No. 253,877, Jun. 3, 1994, Pat. No. 5,773,001.

[51] Int. Cl.⁶ .......................... C07K 16/00; A01N 43/04; C12P 19/44
[52] U.S. Cl. .......................... 530/391.7; 514/25; 514/26; 514/53; 514/168; 530/391.1; 530/391.9
[58] Field of Search .............................. 530/391.1, 391.7, 530/391.9; 514/25, 26, 53, 168

[56] References Cited

U.S. PATENT DOCUMENTS

| | | | |
|---|---|---|---|
| 5,028,697 | 7/1991 | Johnson et al. | 424/181.1 |
| 5,045,451 | 9/1991 | Uhr et al. | 435/7.23 |
| 5,053,394 | 10/1991 | Ellestad et al. | 514/25 |
| 5,094,849 | 3/1992 | Cullinan et al. | 424/181.1 |
| 5,106,951 | 4/1992 | Morgan et al. | 530/391.9 |

OTHER PUBLICATIONS

Borrebreck, J. Immunological Meth., 123:157–165 (1989).
Waldmann, Science, 252:1657–1662 (1991).
Osband et al., Immunol. Today, 11:193–195 (1990).
Harris et al., TIBTECH, 11:42–44 (1993).
Dillman, Annals of Internal Medicine, vol. III, pp. 592–603 (1989).
Bach et al., Immunol. Today, 14:421–425 (1993).
Hermentin et al., Behring Inst. Mitt No. 82, pp. 197–215 (1988).
Seaver, Genetic Engineering News, vol. 14, pp. 10 and 21 (1994).

*Primary Examiner*—Ponnathapura Achutamurthy
*Attorney, Agent, or Firm*—Elizabeth M. Barnhard; H. G. Jackson

[57] ABSTRACT

This invention describes carrier-drug conjugates prepared from disulfide analogs of the calicheamicin family of potent antitumor antibiotics and their derivatives, as well as similar analogs from related antitumor antibiotics such as the esperamicins. The carrier can be an antibody, growth factor, or steroid which targets an undesired population of cells, such as those of a tumor. Whole protein carriers as well as their antigen-recognizing fragments and their chemically or genetically manipulated counterparts are useful for the targeting portion of the conjugates. This invention includes compounds required for the synthesis of these conjugates, appropriate pharmaceutical compositions of the carrier-drug conjugates, and their method of use.

15 Claims, 29 Drawing Sheets

```
  1                                          10                            20                               30
Asp-Ile-Gln-Met-Thr-Gln-Ser-Pro-Ser-Thr-Leu-Ser-Ala-Ser-Val-Gly-Asp-Arg-Val-Thr-Ile-Thr-Cys-Arg-Ala-Ser-Gln-Ser-Ile-Asn- 40                              50                               60
Thr-Trp-Leu-Ala-Trp-Tyr-Gln-Gln-Lys-Pro-Gly-Lys-Ala-Pro-Lys-Leu-Leu-Met-Tyr-Lys-Ala-Ser-Ser-Leu-Glu-Ser-Gly-Val-Pro-Ser- 70                              80                               90
Arg-Phe-Ile-Gly-Ser-Gly-Ser-Gly-Thr-Glu-Phe-Thr-Leu-Thr-Ile-Ser-Ser-Leu-Gln-Pro-Asp-Asp-Phe-Ala-Thr-Tyr-Tyr-Cys-Gln-Gln- 100                             110                              120
Tyr-Asn-Ser-Asp-Ser-Lys-Met-Phe-Gly-Gln-Gly-Thr-Lys-Val-Glu-Val-Lys-Gly-Thr-Val-Ala-Ala-Pro-Ser-Val-Phe-Ile-Phe-Pro-Pro- 130                             140                              150
Ser-Asp-Glu-Gln-Leu-Lys-Ser-Gly-Thr-Ala-Ser-Val-Val-Cys-Leu-Leu-Asn-Asn-Phe-Tyr-Pro-Arg-Glu-Ala-Lys-Val-Gln-Trp-Lys-Val- 160                             170                              180
Asp-Asn-Ala-Leu-Gln-Ser-Gly-Asn-Ser-Gln-Glu-Ser-Val-Thr-Glu-Gln-Asp-Ser-Lys-Asp-Ser-Thr-Tyr-Ser-Leu-Ser-Ser-Thr-Leu-Thr- 190                             200                              210
Leu-Ser-Lys-Ala-Asp-Tyr-Glu-Lys-His-Lys-Val-Tyr-Ala-Cys-Glu-Val-Thr-His-Gln-Gly-Leu-Ser-Ser-Pro-Val-Thr-Lys-Ser-Phe-Asn-

214
Arg-Gly-Glu-Cys
```

FIG. 3
PRIOR ART

```
1                                                         10                                            20                                              30
PCA-Val-Gln-Leu-Val-Gln-Ser-Gly-Ala-Glu-Val-Lys-Lys-Pro-Gly-Ser-Ser-Val-Lys-Val-Ser-Cys-Lys-Ala-Ser-Gly-Gly-Thr-Phe-Ser- 40                                            50                                              60
Arg-Ser-Ala-Ile-Ile-Trp-Val-Arg-Gln-Ala-Pro-Gly-Gln-Gly-Leu-Glu-Trp-Met-Gly-Gly-Ile-Val-Pro-Met-Phe-Gly-Pro-Pro-Asn-Tyr- 70                                            80                                              90
Ala-Gln-Lys-Phe-Gln-Gly-Arg-Val-Thr-Ile-Thr-Ala-Asp-Glu-Ser-Thr-Asn-Thr-Ala-Tyr-Met-Glu-Leu-Ser-Ser-Leu-Arg-Ser-Glu-Asp- 100                                           110                                             120
Thr-Ala-Phe-Tyr-Phe-Cys-Ala-Gly-Gly-Tyr-Gly-Ile-Tyr-Ser-Pro-Glu-Glu-Tyr-Asn-Gly-Gly-Leu-Val-Thr-Val-Ser-Ser-Ala-Ser-Thr- 130                                           140                                             150
Lys-Gly-Pro-Ser-Val-Phe-Pro-Leu-Ala-Pro-Ser-Ser-Lys-Ser-Thr-Ser-Gly-Gly-Thr-Ala-Ala-Leu-Gly-Cys-Leu-Val-Lys-Asp-Tyr-Phe- 160                                           170                                             180
Pro-Glu-Pro-Val-Thr-Val-Ser-Trp-Asn-Ser-Gly-Ala-Leu-Thr-Ser-Gly-Val-His-Thr-Phe-Pro-Ala-Val-Leu-Gln-Ser-Ser-Gly-Leu-Tyr- 190                                           200                                             210
Ser-Leu-Ser-Ser-Val-Val-Thr-Val-Pro-Ser-Ser-Ser-Leu-Gly-Thr-Gln-Thr-Tyr-Ile-Cys-Asn-Val-Asn-His-Lys-Pro-Ser-Asn-Thr-Lys- 220                                           230                                             240
Val-Asp-Lys-Arg-Val-Glu-Pro-Lys-Ser-Cys-Asp-Lys-Thr-His-Thr-Cys-Pro-Pro-Cys-Pro-Ala-Pro-Glu-Leu-Leu-Gly-Gly-Pro-Ser-Val-

250
Phe-Leu-Phe-Pro-Pro-Lys-Pro-Lys-Asp-Thr-Leu-Met-
```

FIG.4
PRIOR ART

HEAVY CHAIN FORWARD PRIMERS

| | | |
|---|---|---|
| CH1 | 5'GCGCGCAAGCTTGCCGCCACCATGAAATGCAGCTGGGTCATSTTCTT | 47 |
| CH2 | 5'GCGCGCAAGCTTGCCGCCACCATGGGATGGAGCTRTATCATSYTCTT | 47 |
| CH3 | 5'GCGCGCAAGCTTGCCGCCACCATGAAGWTGTGGTTAAACTGGGTTTT | 47 |
| CH4 | 5'GCGCGCAAGCTTGCCGCCACCATGRACTTTGGGYTCAGCTTGRT | 44 |
| CH5 | 5'GCGCGCAAGCTTGCCGCCACCATGGACTCCAGGCTCAATTTAGTTTT | 47 |
| CH6 | 5'GCGCGCAAGCTTGCCGCCACCATGGCTGTCYTRGYGCTRCTCTTCTG | 47 |
| CH7 | 5'GCGCGCAAGCTTGCCGCCACCATGGRATGGAGCBGGRTCTTTMTCTT | 47 |
| CH8 | 5'GCGCGCAAGCTTGCCGCCACCATGAGAGTGCTGATTCTTTTGTG | 44 |
| CH9 | 5'GCGCGCAAGCTTGCCGCCACCATGGMTTGGGTGTGGAMCTTGCTATT | 47 |
| CH10 | 5'GCGCGCAAGCTTGCCGCCACCATGGGCAGACTTACATTCTCATTCCT | 47 |
| CH11 | 5'GCGCGCAAGCTTGCCGCCACCATGGATTTTGGGCTGATTTTTTTATTG | 49 |
| CH12 | 5'GCGCGCAAGCTTGCCGCCACCATGATGGTGTTAAGTCTTCTGTACCT | 47 |

Hind3

HEAVY CHAIN BACK PRIMER V/C JUNCTION

| | | |
|---|---|---|
| CH13 | 5'CAGATGGGCCCTTCGTTGAGGCTGMRGAGACDGTGA | 36 |

LIGHT CHAIN FORWARD PRIMERS

| | | |
|---|---|---|
| CL1 | 5'GGACTGTTCGAAGCCGCCACCATGAAGTTGCCTGTTAGGCTGTTGGTGCT | 50 |
| CL2 | 5'GGACTGTTCGAAGCCGCCACCATGGAGWCAGACACACTCCTGYTATGGGT | 50 |
| CL3 | 5'GGACTGTTCGAAGCCGCCACCATGAGTGTGCTCACTCAGGTCCT | 44 |
| CL4 | 5'GGACTGTTCGAAGCCGCCACCATGAGGRCCCCTGCTCAGWTTYTTGG | 47 |
| CL5 | 5'GGACTGTTCGAAGCCGCCACCATGGATTTWCAGGTGCAGATTWTCAGCTT | 50 |
| CL6 | 5'GGACTGTTCGAAGCCGCCACCATGAGGTBCYYTGYTSAGYTYCTGRG | 47 |
| CL7 | 5'GGACTGTTCGAAGCCGCCACCATGGGCWTCAAGATGGAGTCACA | 44 |
| CL8 | 5'GGACTGTTCGAAGCCGCCACCATGTGGGGAYCTBTTTYCMMTTTTTCAAT | 50 |
| CL9 | 5'GGACTGTTCGAAGCCGCCACCATGGTRTCCWCASCTCAGTTCCTT | 45 |
| CL10 | 5'GGACTGTTCGAAGCCGCCACCATGTATATATGTTTGTTGTCTATTTC | 47 |
| CL11 | 5'GGACTGTTCGAAGCCGCCACCATGGAAGCCCCAGCTCAGCTTCTCTT | 47 |

KAPPA LIGHT CHAIN BACK PRIMER V/C JUNCTION

| | | |
|---|---|---|
| CL12 | 5'GGATACAGTTGGTGCAGCATCCGTACGTTT 3' | 30 |

Spl1

KEY: M=A/C, R=A/G, W=A/T, S=C/G, Y=T/C, B=T/G, D=A,G,T, H=A,C,T

FIG. 17
PRIOR ART

A. LIGHT CHAIN

```
              T
ATG GGC ATC AAG ATG GAG TCA CAG ACC CAG GTC TTT GTA TTC GTG TTG CTC TGG
 M   G   I   K   M   E   S   Q   T   Q   V   F   V   F   V   L   L   W

F
TTG TCT GGT GTT GAT GGA GAC ATT GTG ATG ACC CAG TCT CAA AAA TTC ATG TCC
 L   S   G   V   D   G   D   I   V   M   T   Q   S   Q   K   F   M   S
                         1                                  10

ACA TCA GTA GGA GAC AGG GTC AGC ATC ACC TGC AAG GCC AGT CAG AAT GTT CGT
 T   S   V   G   D   R   V   S   I   T   C   K   A   S   Q   N   V   R
                                 20                                  30

ACT GTT GTA GCC TGG TAT CAA CAG AAA CCA GGG CAG TCT CCT AAA ACA CTG ATT
 T   V   V   A   W   Y   Q   Q   K   P   G   Q   S   P   K   T   L   I
                             40

TAC TTG GCC TCC AAC CGG CAC ACT GGA GTC CCT GAT CGC TTC ACA GGC AGT GGA
 Y   L   A   S   N   R   H   T   G   V   P   D   R   F   T   G   S   G
     50                                      60

TCT GGG ACA GAT TTC ACT CTC ACC ATT AGC AAT GTG CAA TCT GAA GAC CTG GCA
 S   G   T   D   F   T   L   T   I   S   N   V   Q   S   E   D   L   A 70                                          80
GAT TAT TTC TGT CTG CAA CAT TGG AGT TAT CCT CTC ACG TTC GGC TCG GGG ACA
 D   Y   F   C   L   Q   H   W   S   Y   P   L   T   F   G   S   G   T
                         90

AAG TTG GAA GTA AAA CGT
 K   L   E   V   K   R
```

FIG.19A
PRIOR ART

B. HEAVY CHAIN

```
                    T           A
   CC ACC ATG AAC TTT GGG CTC AGC TTG GTT TTC CTT GTC CTA ATT TTA AAA GGT
         M   N   F   G   L   S   L   V   F   L   V   L   I   L   K   G
                         F           I
```

```
GTC CAG TGT GAA GTG AAG CTG GTG GAG TCT GGG GGA GGC TTA GTG AAG CCT GGA
 V   Q   C   E   V   K   L   V   E   S   G   G   G   L   V   K   P   G
         1                                       10
```

```
GGG TCC CTG AAA CTC TCC TGT GCA GCC TCT GGA TTC GCT TTC AGT ACC TAT GAC
 G   S   L   K   L   S   C   A   A   S   G   F   A   F   S   T   Y   D
                 20                                       30
```

```
ATG TCT TGG GTT CGC CAG ACT CCG GAG AAG AGG CTG GAG TGG GTC GCA ACC ATT
 M   S   W   V   R   Q   T   P   E   K   R   L   E   W   V   A   T   I
                         40                                       50
```

```
AGT AGT GGT GGT AGT TAC ACC TAC TAT TTA GAC AGT GTG AAG GGC CGA TTC ACC
 S   S   G   G   S   Y   T   Y   Y   L   D   S   V   K   G   R   F   T
     α                               60
```

```
ATC TCC AGA GAC AGT GCC AGG AAC ACC CTA TAC CTG CAA ATG AGC AGT CTG AGG
 I   S   R   D   S   A   R   N   T   L   Y   L   Q   M   S   S   L   R
     70                                      80
```

```
TCT GAG GAC ACG GCC TTG TAT TAC TGT GCA CCG ACT ACG GTA GTC CCG TTT GCT
 S   E   D   T   A   L   Y   Y   C   A   P   T   T   V   V   P   F   A
                         90                                       100
                                             T           C
   TAC TGG GGC CAA GGG ACT CTG GTC ACC GTC TCT GCA
    Y   W   G   Q   G   T   L   V   T   V   S   A
                                 110         113
```

FIG.19B
PRIOR ART

```
         BstBI
5' GCGGGACTGTTCGAAGCCGCCACC 3'
    3'CCTGACAAGCTTCGGCGGTGGTACAGACAGGGGTGGGTTCAGGAGCCTGAGGACGACGAC
        G  L  F  E  A  A  T  M  S  V  P  T  Q  V  L  G  L  L  L

5' TGGCTTACAGATGCCAGATGTGATATCCAGATGACTCAGAGTCCAAGTAGTCTCAGTGTA
                               ACCGAATGTCTACGGTCTACA 5'
    W  L  T  D  A  R  C  D  I  Q  M  T  Q  S  P  S  S  L  S  V

AGTGTAGGTGATAGGGTAACT 3'
TCACATCCACTATCCCATTGATAGTGAACATTCCGGTCAGTCTTACAAGCATGACAACAT
 S  V  G  D  R  V  T  I  T  C  K  A  S  Q  N  V  R  T  V  V

5'CAGCAGAAACCAGGTCTCGCCCCAAAAACTCTCATCTATTTGGCCTCCAAC
CGGACCATAGTCGTCTTTGGTCCAGAGCGG 5'
 A  W  Y  Q  Q  K  P  G  L  A  P  K  I  L  I  Y  L  A  S  N
```

```
                         XbaI
CGGCACACTGGAGTACCATCTAGATTCAGTGGTAGCGGTAGT 3'
                        TCTAAGTCACCATCGCCATCACCATGACTAAAGTGAAAG
 R  H  T  G  V  P  S  R  F  S  G  S  G  S  G  T  D  F  T  F
```

```
                  5'GATATCGCCACTTACTTCTGCCTGCAACATTGGAGT
TGATAGTCATCAGAGGTCGGTCTTCTATAGCGGTGAATGAAGACGGAC 5'
 T  I  S  S  L  Q  P  E  D  I  A  T  Y  F  C  L  Q  H  W  S
```

```
                                                    SpII
TATCCTCTCACGTTCGGTCAGGGTACTAAAGTAGAAGTAAAACGTACGGGCCGG 3'
                                    3'CTTCATTTTGCATGCCCGGCC 5'
 Y  P  L  T  F  G  Q  G  T  K  V  E  V  K  R  t  g  r
```

FIG.20

```
                Hind3
5'  GCGCGCAAGCTTGCCGCCACC  3'
3'  CGCGCGTTCGAACGGCGGTGGTACCTTACCTCGACCCAGAAAGAGAAGAAGGACAGTCAT
    A  R  K  L  A  A  T  M  E  W  S  W  V  F  L  F  F  L  S  V 5'GTCCATTCTGAGGTGCAGCTGCTGGAGTCTGGAGGAGGACTGGTGCAGCCT
TGATGTCCTCAGGTAAGACTCCACGTCGAC  5'
  T  T  G  V  H  S  E  V  Q  L  L  E  S  G  G  G  L  V  Q  P GGAGGATCTCTGAGACTGTCTTGTGCAGCATCTGGATTCGCTTTC  3'
                  3'CGTCGTAGACCTAAGCGAAAGTCATGGATACTGTAC
  G  G  S  L  R  L  S  C  A  A  S  G  F  A  F  S  T  Y  D  M
                                        Xhol
                             5'GTGGCAACCATTAGTAGTGGT
AGAACCCACTCTGTCCGTGGACCTTTTCCTGAGCTCACCCACCGTTGGTAATCATCACCA  5'
  S  W  V  R  Q  A  P  G  K  G  L  E  W  V  A  T  I  S  S  G GGTAGTTACACCTACTATTTAGACAGTGTGAAGGGAAGATTCACAATTTCCAGAGACTCT
                                                3'AGGTCTCTGAGA
  G  S  Y  T  Y  Y  L  D  S  V  K  G  R  F  T  I  S  R  D  S AGCAAGAAT  3'
TCGTTCTTATGTGACATGGACGTCTACTTAAGAGACGTCCGTCTCCTGAGACGTTAAATG
  S  K  N  T  L  Y  L  Q  M  N  S  L  Q  A  E  D  S  A  I  Y 5'TGTGCACCGACTACGGTAGTCCCGTTTGCTTACTGGGGACAGGGAACACTGGTGACA
ATGACACGTGGCTGATGCCATCAG  5'
  Y  C  A  P  T  T  V  V  P  F  A  Y  W  G  Q  G  T  L  V  T
                    Apa 1
GTGTCTTCTGCCTCAACGAAGGGCCCGCGCGC  3'
          3'GAGTTGCTTCCCGGGCGCGCG  5'
  V  S  S  a  s  t  k  g  p  r
```

FIG.21
PRIOR ART

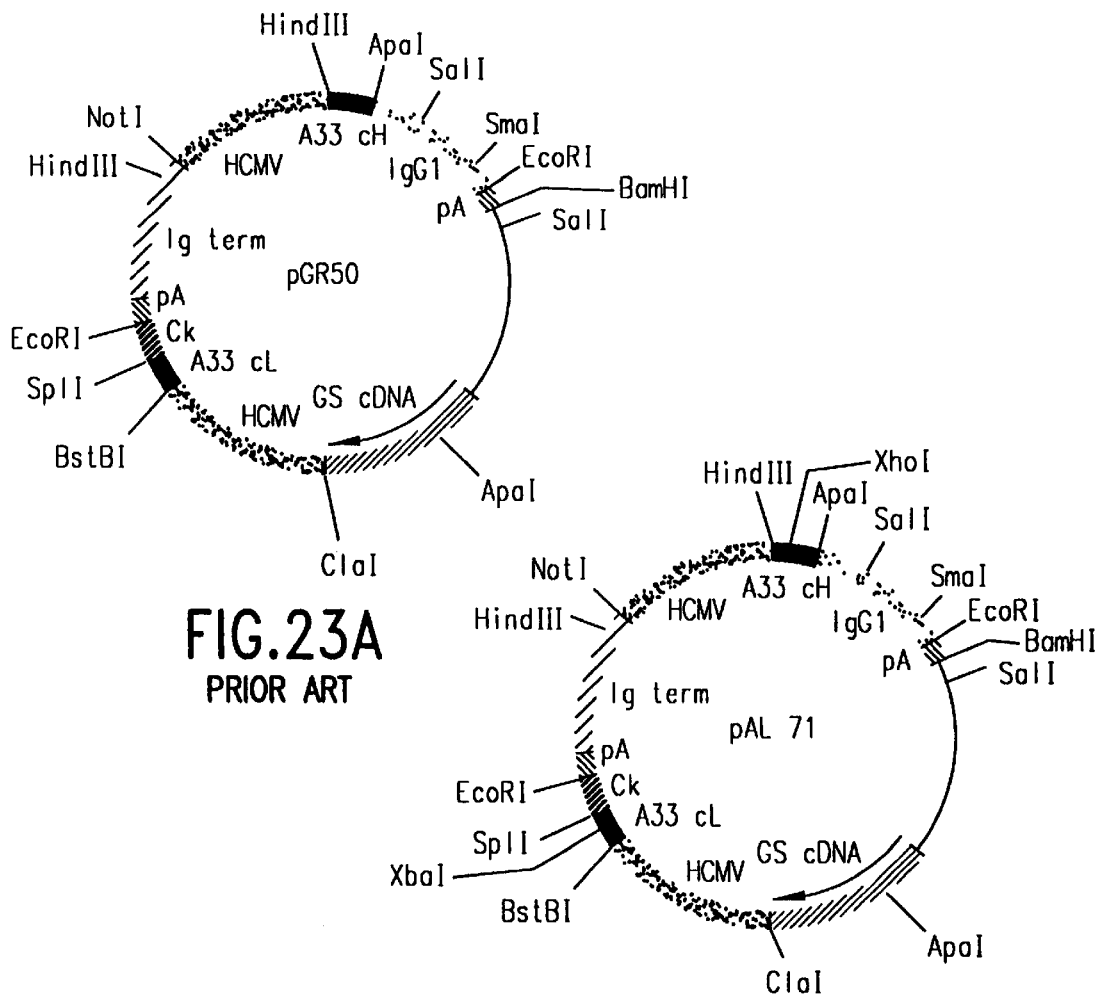
FIG.23A PRIOR ART
FIG.23B PRIOR ART
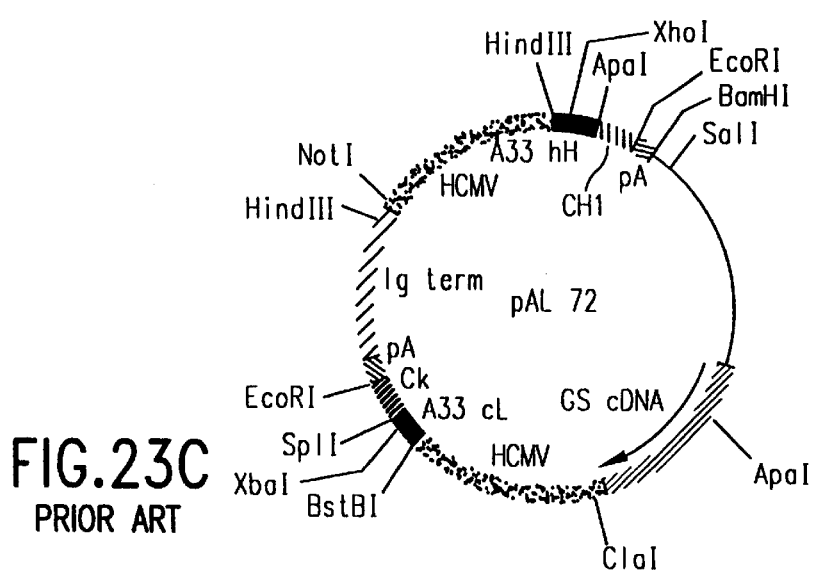
FIG.23C PRIOR ART

PROCESS FOR PREPARING CONJUGATES OF METHYLTRITHIO ANTITUMOR AGENTS

This is a divisional of application Ser. No. 08/253,877 filed on Jun. 3, 1994 now U.S. Pat No. 5,773,001.

SUMMARY OF THE INVENTION

This invention describes carrier-drug conjugates prepared from disulfide analogs of the calicheamicin family of potent antitumor antibiotics and their derivatives, as well as similar analogs from related antitumor antibiotics such as the esperamicins. The carrier can be an antibody, growth factor, or steroid which targets an undesired population of cells, such as those of a tumor. Whole protein carriers as well as their antigen-recognizing fragments and their chemically or genetically manipulated counterparts are useful for the targeting portion of the conjugates. This invention includes compounds required for the synthesis of these conjugates, appropriate pharmaceutical compositions of the carrier-drug conjugates, and their method of use.

More specifically, one aspect of the invention includes a cytotoxic drug conjugate of the formula:

$$Z^3[CO\text{-}Alk^1\text{-}Sp^1\text{-}Ar\text{-}Sp^2\text{-}Alk^2\text{-}C(Z^1)=Z^2]_m$$

wherein
- $Z^3$ is a protein selected from mono- and polyclonal antibodies, their antigen-recognizing fragments, and their chemically or genetically manipulated counterparts and growth factors and their chemically or genetically manipulated counterparts, wherein a covalent bond to the protein is an amide formed from reaction with lysine side chains, or a steroid, wherein the covalent bond to the steroid is an amide or an ester;
- m is from about 0.1 to 15;
- $Alk^1$ and $Alk^2$ are independently a bond or branched or unbranched ($C_1$–$C_{10}$) alkylene chain;
- $Sp^1$ is a bond, —S—, —O—, —CONH—, —NHCO—, —NR'—, —N($CH_2CH_2$)$_2$N—, or —X—AR'—Y—($CH_2$)$_n$—Z wherein X, Y, and Z are independently a bond, —NR'—, —S—, or —O—, with the proviso that when n=0, then at least one of Y and Z must be a bond and AR' is 1,2-, 1,3-, or 1,4-phenylene optionally substituted with one, two, or three groups of ($C_1$–$C_5$) alkyl, ($C_1$–$C_4$) alkoxy, ($C_1$–$C_4$) thioalkoxy, halogen, nitro, COOR', CONHR', O($CH_2$)$_n$COOR', S($CH_2$)$_n$COOR', O($CH_2$)$_n$CONHR', or S($CH_2$)$_n$CONHR', with the proviso that when $Alk^1$ is a bond, $Sp^1$ is also a bond;
- n is an integer from 0 to 5;
- R' is a branched or unbranched ($C_1$–$C_5$) chain optionally substituted by one or two groups of —OH, ($C_1$–$C_4$) alkoxy, ($C_1$–$C_4$) thioalkoxy, halogen, nitro, ($C_1$–$C_3$) dialkylamino, or ($C_1$–$C_3$) trialkylammonium-$A^-$ where $A^-$ is a pharmaceutically acceptable anion completing a salt;
- $Sp^2$ is a bond, —S—, or —O—, with the proviso that when $Alk^2$ is a bond, $Sp^2$ is also a bond;
- $Z^1$ is H, ($C_1$–$C_5$) alkyl, or phenyl optionally substituted with one, two, or three groups of ($C_1$–$C_5$) alkyl, ($C^1$–$C_4$) alkoxy, ($C_1$–$C_4$) thioalkoxy, halogen, nitro, COOR', CONHR', O($CH_2$)$_n$COOR', S($CH_2$)$_n$COOR', O($CH_2$)$_n$CONHR', or S($CH_2$)$_n$CONHR' wherein n and R' are as hereinbefore defined;
- Ar is 1,2-, 1,3-, or 1,4-phenylene optionally substituted with one, two, or three groups of ($C_1$–$C_6$) alkyl, ($C_1$–$C_5$) alkoxy, ($C_1$–$C_4$) thioalkoxy, halogen, nitro, COOR', CONHR', O($CH_2$)$_n$COOR', S($CH_2$)$_n$COOR', O($CH_2$)$_n$CONHR', or S($CH_2$)$_n$CONHR' wherein n and R' are as hereinbefore defined or a 1,2-, 1,3-, 1,4-, 1,5-, 1,6-, 1,7-, 1,8-, 2,3-, 2,6-, or 2,7-naphthylidene or

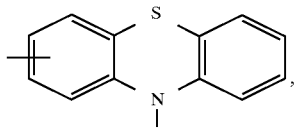

each naphthylidene or phenothiazine optionally substituted with one, two, three, or four groups of ($C_1$–$C_6$) alkyl, ($C_1$–$C_5$) alkoxy, ($C_1$–$C_4$) thioalkoxy, halogen, nitro, or COOR', CONHR', O($CH_2$)$_n$COOR', S($CH_2$)$_n$COOR', O($CH_2$)$_n$CONHR', or S($CH_2$)$_n$CONHR' wherein n and R' are as hereinbefore defined, with the proviso that when Ar is naphthylidene, $Z^1$ is not hydrogen and with the proviso that when Ar is phenothiazine, $Sp^1$ is a bond only connected to nitrogen;

$Z^2$ is Q-Sp-S-S-W, wherein W is

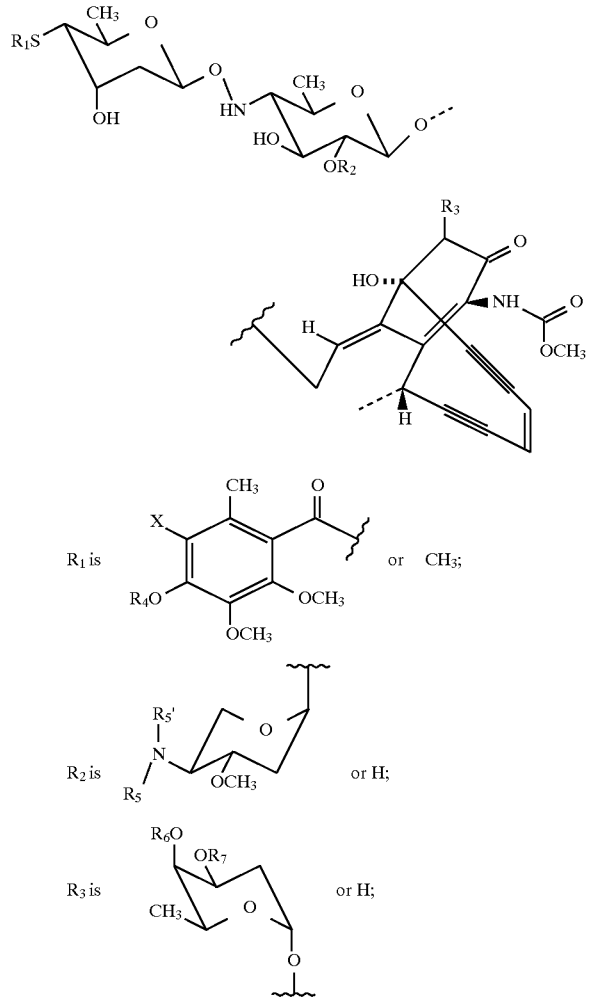

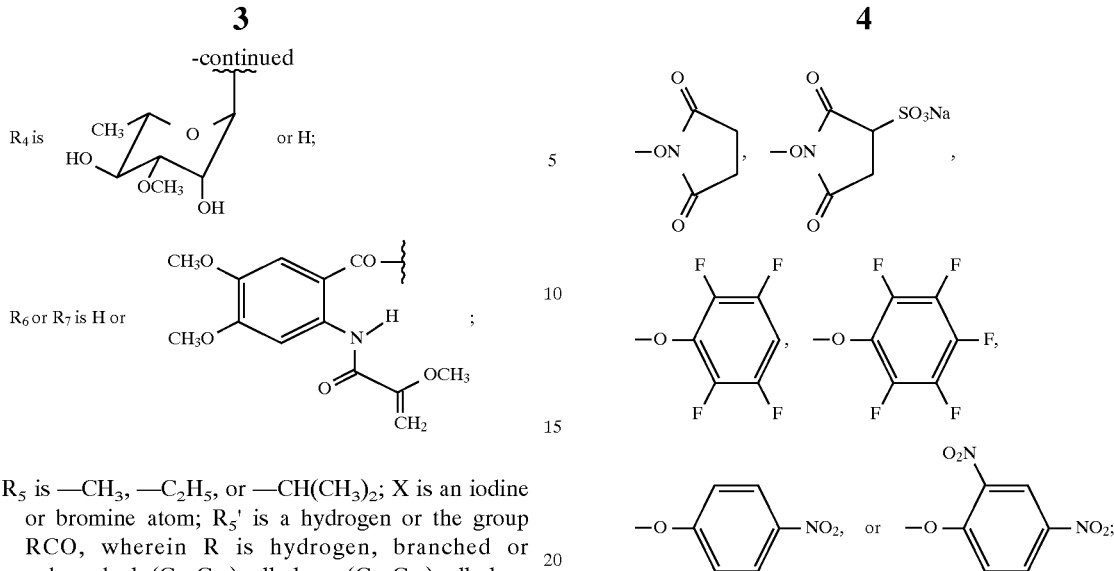

$R_4$ is ... or H;

$R_6$ or $R_7$ is H or ...

$R_5$ is —CH$_3$, —C$_2$H$_5$, or —CH(CH$_3$)$_2$; X is an iodine or bromine atom; $R_5'$ is a hydrogen or the group RCO, wherein R is hydrogen, branched or unbranched (C$_1$–C$_{10}$) alkyl or (C$_1$–C$_{10}$) alkylene group, a (C$_6$–C$_{11}$) aryl group, a (C$_6$–C$_{11}$) aryl-alkyl (C$_1$–C$_5$) group, or a heteroaryl or heteroaryl-alkyl (C$_1$–C$_5$) group wherein heteroaryl is defined as 2- or 3-furyl, 2- or 3-thienyl, 2- or 3-(N-methylpyrrolyl), 2-, 3-, or 4-pyridly, 2-, 4-, or 5-(N-methylimidazolyl), 2-, 4-, or 5-oxazolyl, 2-, 3-, 5-, or 6-pyrimidinyl, 2-, 3-, 4-, 5-, 6-, 7-, or 8-quinolyl, or 1-, 3-, 4-, 5-, 6-, 7-, or 8-isoquinolyl, all aryl and heteroaryl groups optionally substituted by one or more hydroxy, amino, carboxy, halo, nitro, lower (C$_1$–C$_3$) alkoxy, or lower (C$_1$–C$_5$) thioalkoxy groups;

Sp is a straight or branched-chain divalent or trivalent (C$_1$–C$_{18}$) radical, divalent or trivalent aryl or heteroaryl radical, divalent or trivalent (C$_3$–C$_{18}$) cycloalkyl or heterocycloalkyl radical, divalent or trivalent aryl- or heteroaryl-alkyl (C$_1$–C$_{18}$) radical, divalent or trivalent cycloalkyl- or heterocycloalkyl-alkyl (C$_1$–C$_{18}$) radical or divalent or trivalent (C$_2$–C$_{18}$) unsaturated alkyl radical, wherein heteroaryl is furyl, thienyl, N-methylpyrrolyl, pyridinyl, N-methylimidazolyl, oxazolyl, pyrimidinyl, quinolyl, isoquinolyl, N-methylcarbazoyl, aminocoumarinyl, or phenazinyl and wherein if Sp is a trivalent radical, it can be additionally substituted by lower (C$_1$–C$_5$) dialkylamino, lower (C$_1$–C$_5$) alkoxy, hydroxy, or lower (C$_1$–C$_5$) alkylthio groups; and Q is =NHNCO—, =NHNCS—, =NHNCONH—, =NHNCSNH—, or =NO— and includes the conjugates use as antitumor agents.

A second aspect of this invention involves modified drugs, useful as intermediates for constructing conjugates, of the formula:

$Z^3$[CO-Alk$^1$-Sp$^1$-Ar-Sp$^2$-Alk$^2$-C(Z$^1$)=Z$^2$]m wherein $Z^1$, $Z^2$, Alk$^1$, Sp$^1$, Ar, Sp$^2$, and Alk$^2$ are as hereinbefore defined;

$Z^3$ is halogen, hydroxy, OM wherein M is a metal completing a salt, —N$_3$,

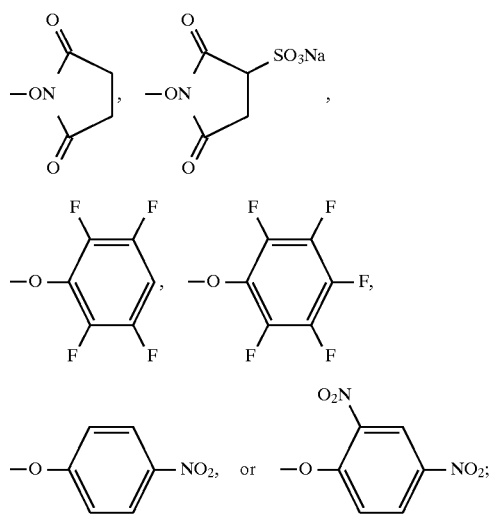

and m is 1.

A third aspect of this invention involves linkers, useful for constructing drug conjugates, of the formula:

$Z^3$[CO-Alk$^1$-Sp$^1$-Ar-Sp$^2$-Alk$^2$-C(Z$^1$)=Z$^2$]m wherein $Z^3$ is halogen, hydroxy, OM wherein M is a metal completing a salt, —N$_3$, Alk$^1$ and Alk$^2$ are independently a bond or branched or unbranched (C$_1$–C$_{10}$) alkylene chain;

Sp$^1$ is a bond, —S—, —O—, —CONH—, —NHCO—, —NR'—, —N(CH$_2$CH$_2$)$_2$N—, or —X—AR'—Y—(CH$_2$)$_n$ —Z wherein X, Y, and Z are independently a bond, —NR'—, —S—, or —O—, with the proviso that when n=0, then at least one of Y and Z must be a bond and Ar' is 1,2-, 1,3-, or 1,4-phenylene optionally substituted with one, two, or three groups of (C$_1$–C$_5$) alkyl, (C$_1$–C$_4$) alkoxy, (C$_1$–C$_4$) thioalkoxy, halogen, nitro, COOR', CONHR', O(CH$_2$)$_n$COOR', S(CH$_2$)$_n$COOR', O(CH$_2$)$_n$CONHR', or S(CH$_2$)$_n$CONHR', with the proviso that when Alk$^1$ is a bond, Sp$^1$ is a bond;

n is an integer from 0 to 5;

R' is a branched or unbranched (C$_1$–C$_5$) chain optionally substituted by one or two groups of —OH, (C$_1$–C$_4$)

alkoxy, $(C_1-C_4)$ thioalkoxy, halogen, nitro, $(C_1-C_3)$ dialkylamino, or $(C_1-C_3)$ trialkylammonium —A— where $A^-$ is a pharmaceutically acceptable anion completing a salt;

Ar is 1,2-, 1,3-, or 1,4-phenylene optionally substituted with one, two, or three groups of $(C_1-C_6)$ alkyl, $(C_1-C_5)$ alkoxy, $(C_1-C_4)$ thioalkoxy, halogen, nitro, or COOR', CONHR', $O(CH_2)_n COOR'$, $S(CH_2)_n COOR'$, $O(CH_2)_n CONHR'$, or $S(CH_2)_n CONHR'$ wherein n and R' are as hereinbefore defined or a 1,2-, 1,3-, 1,4-, 1,5-, 1,6-, 1,7-, 1,8-, 2,3-, 2,6-, or 2,7-naphthylidene or

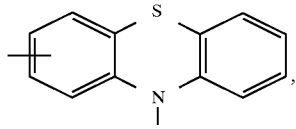

each naphthylidene or phenothiazine optionally substituted with one, two, three, or four groups of $(C_1-C_6)$ alkyl, $(C_1-C_5)$ alkoxy, $(C_1-C_4)$ thioalkoxy, halogen, nitro, or COOR', CONHR', $O(CH_2)_n COOR'$, $S(CH_2)_n COOR'$, $O(CH_2)_n CONHR'$, or $S(CH_2)_n CONHR'$ wherein n and R' are as hereinbefore defined, with the proviso that when Ar is naphthylidene, $Z^1$ is not hydrogen and with the proviso that when Ar in phenothiazine, $Sp^1$ is a bond only connected to nitrogen;

$Sp^2$ is a bond, —S—, or —O—, with the proviso that when $Alk^2$ is a bond, $Sp^2$ is a bond;

$Z^1$ is H, $(C_1-C_5)$ alkyl, or phenyl optionally substituted with one, two, or three groups of $(C_1-C_5)$ alkyl, $(C_1-C_4)$ alkoxy, $(C_1-C_4)$ thioalkoxy, halogen, nitro, COOR', CONHR', $O(CH_2)_n COOR'$, $S(CH_2)_n COOR'$, $O(CH_2)_n CONHR'$, or $S(CH_2)_n CONHR'$ wherein n and R' are as hereinbefore defined;

$Z^2$ is oxygen; and m is 1, with the proviso that when Ar is unsubstituted 2,6-naphthylene or 1,3- or 1,4-phenylene optionally substituted with one group of $(C_1-C_6)$ alkyl or $(C_1-C_5)$ alkoxy and $Alk^2$ is a bond, then $Sp^1$ is not a bond, —O—, or —NHCO—.

DESCRIPTION OF THE DRAWINGS

FIG. 1: DNA and amino acid sequences (SEQ ID NO:1) for h-P67.6 light chain.

FIG. 2: DNA and amino acid sequences (SEQ ID NO:3) for h-P67.6 heavy chain.

FIG. 3 is the amino acid sequence for the light chain of the γG1-immunoglobulin Eu.

FIG. 4 is the amino acid sequence of residues 1-252 of the heavy chain of the γG1-immunoglobulin Eu.

FIG. 17 shows the oligonucleotide primers for PCR cloning of murine variable region sequences.

FIG. 18A is a schematic diagram of the chimeric light chain expression vector pRO108. FIG. 18B is a schematic diagram of the chimeric heavy chain expression vector pRO107.

FIG. 19A–B shows the amino acid sequences of the variable regions of the A33 light chain (FIG. 19A) and heavy chain (FIG. 19B). Sequences for the signal sequence are underlined and the mature variable region are shown in upper case. DNA sequences defined by the PCR primers are italicized. CDR regions are double underlined.

FIG. 20 shows oligonucleotide sequences used for the assembly of the A33 humanized light chain variable region. These oligonucleotide sequences are underlined. The expected coding sequence for the signal sequence is italicized, the mature variable region is in upper case, and the N terminal sequence of the human kappa constant region is in lower case, and all are shown below the underlined oligonucleotide sequences. The CDR regions and the non-CDR residues derived from the murine sequence are double underlined.

FIG. 21 shows oligonucleotide sequences used for the assembly of the A33 humanized heavy chain variable region. These oligonucleotide sequences are underlined. The expected coding sequence for the signal sequence is italicized, the mature variable region is in upper case, and the N terminal sequence of the human CH1 domain region is in lower case, and all are shown below the underlined oligonucleotide sequences. The CDR regions and the non-CDR residues derived from the murine sequence are double underlined.

FIG. 23A–C are schematic diagrams of the chimeric and humanized A33 GS expression vectors. FIG. 23A is a schematic diagram of the chimeric A33(γ1) expression vector pGR50. FIG. 23B is a schematic diagram of the humanized A33(γ1) expression vector pAL71. FIG. 23C is a schematic diagram of the humanized A33 FAB'(γ4Δcys) expression vector pAL72. Only relevant restriction sites are shown.

BACKGROUND OF THE INVENTION

Figure 5:
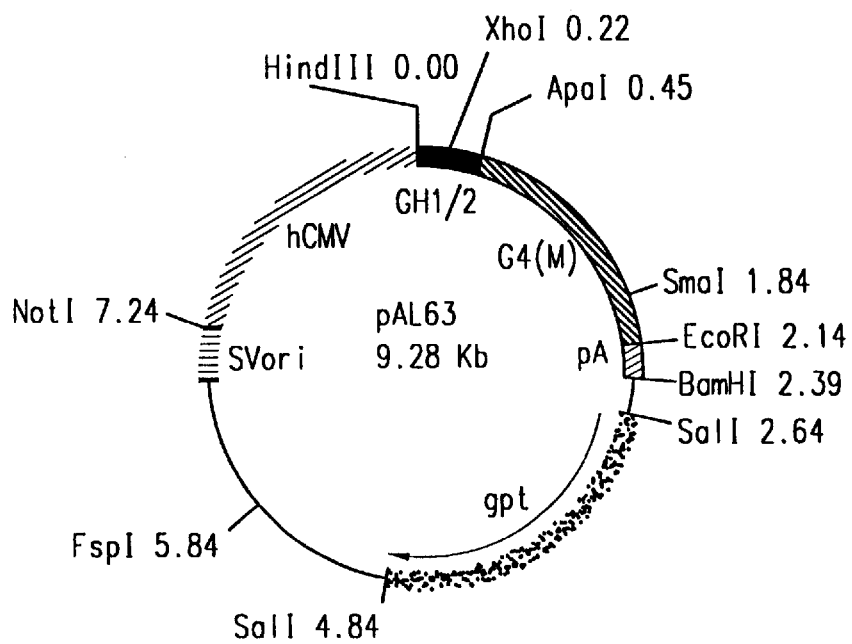
FIG. 5: Plasmid for h-P67.6 heavy chain expression.

Since the discovery of methodology for producing monoclonal antibodies was published in the 1970's (G. Kohler and C. Milstein, "Nature" 256, 495 (1975)), numerous attempts have been made to use these proteins to achieve selective targeting of antitumor agents to tumors. (E.g., see T. Ghose and A. H. Blair, "CRC Critical Rev. Drug Carrier Systems" 3, 263 (1987), G. A. Koppel, "Bioconjugate Chem." 1, 13 (1990), and J. Upeslacis and L. Hinman, "Ann. Rep. Med. Chem." 23, 151 (1988).) Although progress continues to be made in this field, most classical antitumor agents produce antibody conjugates which are relatively ineffective for a variety of reasons. Among the reasons for this ineffectiveness is the lack of potency of the chemotherapeutic agent and its poor utilization due to the lack of efficient release of the drug at its site of action.

The potent family of antibacterial and antitumor agents, known collectively as the calicheamicins or the LL-E33288 complex, are described and claimed in U.S. Pat. No. 4,970,198 (1990). The most potent of the agents is designated $\gamma_1^I$, which is herein referred to simply as gamma. The dihydro derivatives of these compounds are described in U.S. Pat. No. 5,037,651 (1991) and the N-acylated derivatives are described in U.S. Pat. No. 5,079,233 (1992). Related compounds which are also useful in this invention include the esperamicins which are described and claimed in U.S. Pat. No. 4,675,187 (1987); 4,539,203; 4,554,162; and U.S. Pat. No. 4,837,206. All of these compounds contain a methyltrisulfide that can be reacted with appropriate thiols to form disulfides, at the same time introducing a functional group such as a hydrazide or similar nucleophile. Examples of this reaction with the calicheamicins are given in U.S. Pat. No. 5,053,394 which also discloses targeted forms of the calicheamicins. All information in the above-mentioned patent citations is incorporated herein by reference. Two compounds which are useful for the synthesis of conjugates with carrier molecules, as disclosed and claimed in U.S. Pat. No. 5,053,394, are shown in Table 1.

TABLE 1

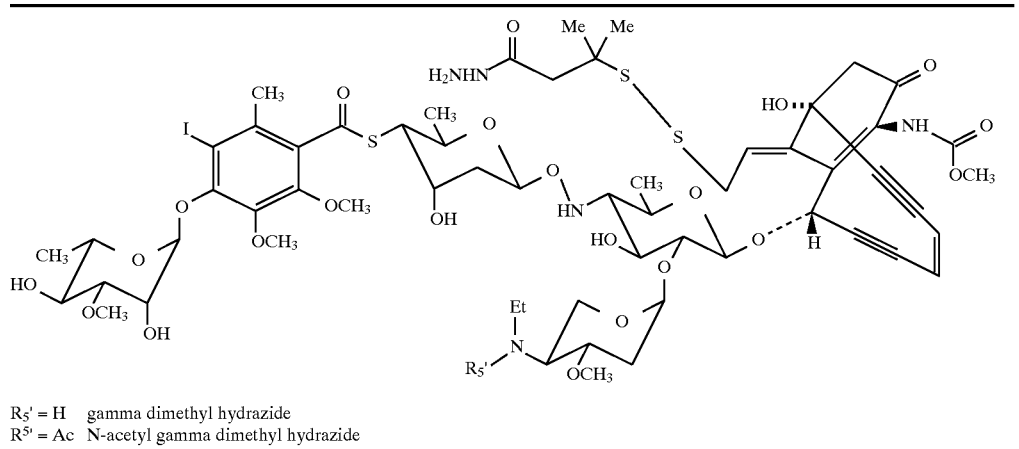

$R_5' = H$  gamma dimethyl hydrazide
$R^{5'} = Ac$  N-acetyl gamma dimethyl hydrazide Included as carrier molecules in U.S. Pat. No. 5,053,394 are steroids, growth factors, antibodies, antibody fragments, and their genetically or enzymatically engineered counterparts, hereinafter referred to singularly or as a group as carrier. The essential property of the carrier is its ability to recognize an antigen or receptor associated with an undesired cell line. Examples of carriers are given in U.S. Pat. No. 5,053,394, and such carriers are also appropriate in the present invention. Antibody carriers can be from almost any mammalian species (eg. mouse, human, dog, etc.) and can be produced by various methods (eg. murine antibodies via hybridomas, human antibodies via hybridomas from transgenetic mice, etc).

Specific examples of carriers which are exemplified herein are the antibodies P67.6, A33, CT-M-01 and the "anti-Tac" antibody of Waldman. These antibodies are used here in two forms: a murine form, designated by an "m" (e.g., m-P67.6), and a genetically engineered, humanized form, designated by an "h" (e.g., h-P67.6) whenever appropriate. The basic technology for humanization is disclosed by Winter in U.S. Pat. No. 5,225,539 (1993) and by Adair in WO 91/09967 (1991). m-P67.6 is disclosed in I. D. Bernstein et al., "J. Clin. Invest." 79, 1153 (1987) and recognizes the CD33 antigen which is prevalent on certain human myeloid tumors, especially acute non-lymphocytic leukemia (ANLL).

Figure 1:
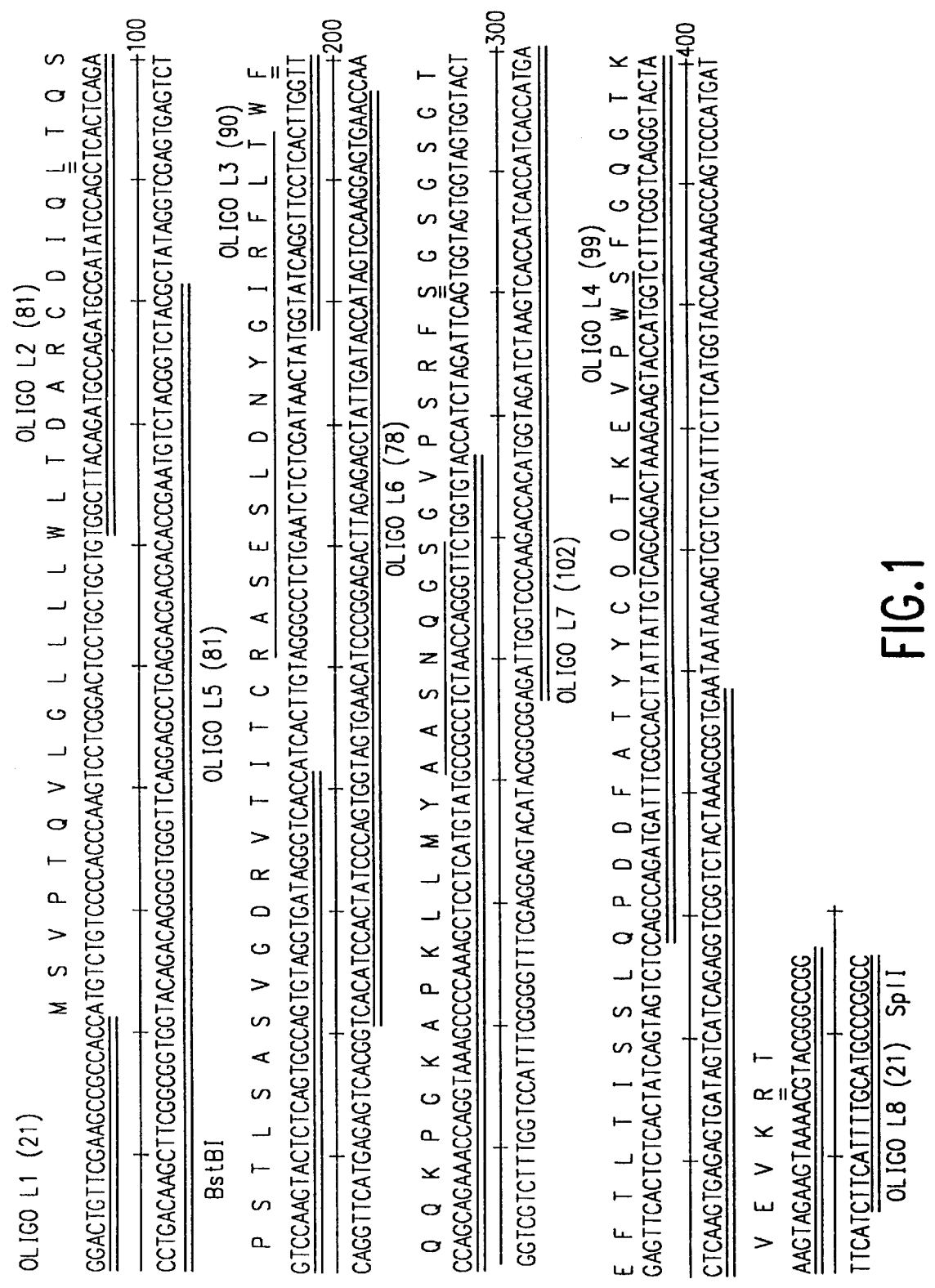
Figure 2:
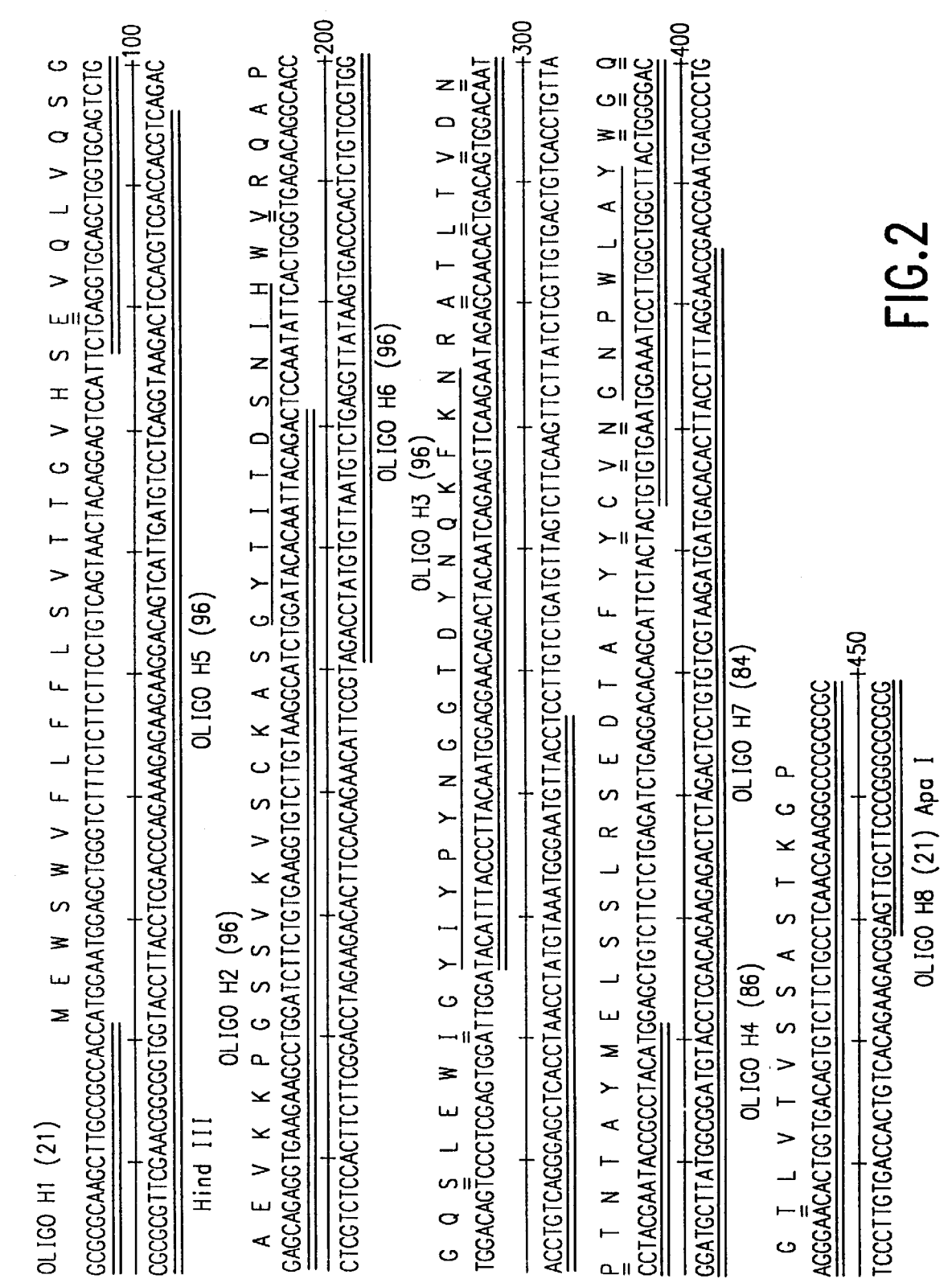

FIG. 1 and FIG. 2 show the DNA coding and predicted amino acid sequences of the variable regions of one particular h-P67.6 that is particularly suitable for use in the present invention. The framework for this antibody is the EU framework for human $IgG_4$ shown in Gottlieb et al., "Biochemistry: 9, 3155 and 3161 (1970) and the amino acid sequences set forth in FIG. 1 (SEQ ID NO: 2) and FIG. 2 (SEQ ID NO: 4). The antibody was prepared using the general strategy described in WO 91/09967. It is first of all necessary to sequence the DNA coding for the heavy and light chain variable regions of the donor antibody, to determine their amino acid sequences. It is also necessary to choose appropriate acceptor heavy and light chain variable regions, of known amino acid sequence. The CDR-grafted chain is then designed starting from the basis of the acceptor sequence. It will be appreciated that in some cases the donor and acceptor amino acid residues may be identical at a particular position and thus no change of acceptor framework residue is required.
1. As a first step, donor residues are substituted for acceptor residues in the CDRs. For this purpose the CDRs are preferably defined as follows:
   Heavy chain—CDR1: residues 26–35
      —CDR2: residues 50–65
      —CDR3: residues 95–102
   Heavy chain —CDR1: residues 24–34
      —CDR2: residues 50–56
      —CDR3: residues 89–97 The positions at which donor residues are to be substituted for acceptor in the framework are then chosen as follows, first of all with respect to the heavy chain and subsequently with respect to the light chain.
2. Heavy Chain
2.1 Choose donor residues at all of positions 23, 24, 49, 71, 73 and 78 of the heavy chain or all of positions 23, 24 and 49 (71, 73 and 78 are always either all donor or all acceptor).
2.2 Check that the following have the same amino acid in donor and acceptor sequences, and if not preferably choose the donor: 2, 4, 6, 25, 36, 37, 39, 47, 48, 93, 94, 103, 104, 106 and 107.
2.3 To further optimize affinity, consider choosing donor residues at one, some or any of:
   i. 1, 3
   ii. 72, 76
   iii. If 48 is different between donor and acceptor sequences, consider 69
   iv. If at 48 the donor residue is chosen, consider 38 and 46
   v. If at 69 the donor residue is chosen, consider 80 and then 20
   vi. 67
   vii. If at 67 the donor residue is chosen, consider 82 and then 18
   viii. 92
   ix. 88
   x. 9, 11, 41, 87, 108, 110, 112
3. Light Chain
3.1 Choose donor at 46, 48, 58 and 71
3.2 Check that the following have the same amino acid in donor and acceptor sequences, if not preferably choose donor: 2, 4, 6, 35, 38, 44, 47, 49, 62, 64–69 inclusive, 85, 87, 98, 99, 101 and 102
3.3 To further optimize affinity, consider choosing donor residues at one, some or any of:
   i. 1,3
   ii. 63
   iii. 60, if 60 and 54 are able to form potential salt bridge
   iv. 70, if 70 and 24 are able to form potential salt bridge
   v. 73, and 21 if 47 is different between donor and acceptor
   vi. 37, and 45 if 47 is different between donor and acceptor
   vii. 10, 12, 40, 80, 103,105

In order to transfer the binding site of an antibody into a different acceptor framework, a number of factors need to be considered.

1. The extent of the CDRs
The CDRs (Complementary Determining Regions) were defined by Wu and Kabat [(Wu, T. T., and Kabat, E. A., J. Exp. Med. 132: 211–250 (1979); Kabat, E. A., et al., Sequences of Proteins of Immunological Interest, U.S. Dept. of Health and Human Services, NIH, 1987 (hereinafter "Kabat et al.") on the basis of an analysis of the variability of different regions of antibody variable regions. Three regions per domain were recognized. In the light chain, the sequences are 24–34, 50–56, 89–97 (numbering according to Kabat et al., Eu Index) inclusive and in the heavy chain the sequences are 31–35, 50–65 and 95–102 inclusive.

When antibody structures became available, it became apparent that these CDR regions corresponded in the main to loop regions which extended from the β barrel framework of the light and heavy variable domains. For H1 there was a discrepancy in that the loop was from 26 to 32 inclusive and for H2 the loop was 52 to 56 and for L2 from 50 to 53. However, with the exception of H1, the CDR regions encompassed the loop regions and extended into the β strand frameworks. In H1 residue, 26 tends to be a serine and 27 a phenylalanine or tyrosine, residue 29 is a phenylalanine in most cases. Residues 28 and 30 which are surface residues exposed to solvent might be involved in antigen-binding. A prudent definition of the H1 CDR therefore would include residues 26–35 to include both the loop region and the hypervariable residues 33–35.

It is of interest to note the example of Riechmann et al., Nature, 332: 323–3241 (1988), who used the residue 31–35 choice for CDR-H1. In order to produce efficient antigen binding, residue 27 also needed to be recruited from the donor (rat) antibody.

2. Non-CDR residues which contribute to antigen binding

By examination of available X-ray structures, a number of residues have been identified which may have an effect on net antigen binding and which can be demonstrated by experiment. These residues can be subdivided into a number of groups.

2.1 Surface residues near CDR (all numbering as in Kabat et al.).

2.1.1 Heavy Chain—Key residues are 23, 71 and 73. Other residues which may contribute to a lesser extent are 1, 3 and 76. Finally, 25 is usually conserved but the murine residue should be used if there is a difference.

2.1.2 Light Chain—Many residues close to the CDRs, e.g. 63, 65, 67 and 69 are conserved. If conserved, none of the surface residues in the light chain are likely to have a major effect. However, if the murine residue at these positions is unusual, then it would be of benefit to analyze the likely contribution more closely. Other residues which may also contribute to binding are 1 and 3, and also 60 and 70 if the residues at these positions and at 54 and 24, respectively, are potentially able to form a salt bridge, i.e., 60+54; 70+24.

2.2 Packing residues near the CDRs.

2.2.1 Heavy Chain—Key residues are 24, 49 and 78. Other key residues would be 36 if not a tryptophan, 94 if not an arginine, 104 and 106 if not glycines and 107 if not a threonine. Residues which may make a further contribution to stable packing of the heavy chain and hence improved affinity are 2, 4, 6, 38, 46, 67 and 69. 67 packs against the CDR residue 63 and this pair could be either both mouse or both human. Finally, residues which contribute to packing in this region but from a longer range are 18, 20, 80, 82 and 86. 82 packs against 67 and in turn 18 packs against 82. 80 packs against 69 and in turn 20 packs against 80. 86 forms an H bond network with 38 and 46. Many of the mouse-human differences appear minor, e.g., Leu-lle, but could have a minor impact on correct packing which could translate into altered positioning of the CDRs.

2.2.2 Light Chain—Key residues are 48, 58 and 71. Other key residues would be 6 if not glutamine, 35 if not tryptophan, 62 if not phenylalanine or tyrosine, 64, 66, 68, 99 and 101 if not glycines and 102 if not a threonine. Residues which make a further contribution are 2, 4, 37, 45 and 47. Finally, residues 73 and 21 and 19 may make long distance packing contributions of a minor nature.

2.3 Residues at the variable domain interface between heavy and light chains—In both the light and heavy chains most of the non-CDR interface residues are conserved. If a conserved residue is replaced by a residue of different character, is replaced by a residue of different character, e.g., size or charge, it should be considered for retention as the murine residue.

2.3.1 Heavy Chain—Residues which need to be considered are 37 if the residue is not a valine but is of larger side chain volume or has a charge or polarity. Other residues are 39 if not a glutamine, 45 if not a leucine, 47 if not a tryptophan, 91 if not a phenylalanine or tyrosine, 93 if not an alanine and 103 if not a tryptophan. Residue 89 is also at the interface but is not in a position where the side chain could be or great impact.

2.3.2 Light Chain—Residues which need to be considered are 36, if not a tyrosine, 38 if not a glutamine, 44 if not a proline, 46, 49 if not tyrosine, residue 85, residue 87 if not a tyrosine and 98 if not a phenylalanine.

2.4 Variable-Constant region interface—The elbow angle between variable and constant regions may be affected by alterations in packing of key residues in the variable region against the constant region which may affect the position of $V_L$ and $V_H$ with respect to one another. Therefore it is worth noting the residues likely to be in contact with the constant region. In the heavy chain the surface residues potentially in contact with the variable region are conserved between mouse and human antibodies, therefore the variable region contact residues may influence the V-C interaction. In the light chain, the amino acids found at a number of the constant region contact points vary, and the V & C regions are not in such close proximity as the heavy chain. Therefore the influences of the light chain V-C interface may be minor.

2.4.1 Heavy Chain—contact residues are 7, 11, 41, 87, 108, 100, 112.

2.4.2 Light Chain—In the light chain potentially contacting residues are 10, 12, 40, 80, 83, 103 and 105.

Figure 6:
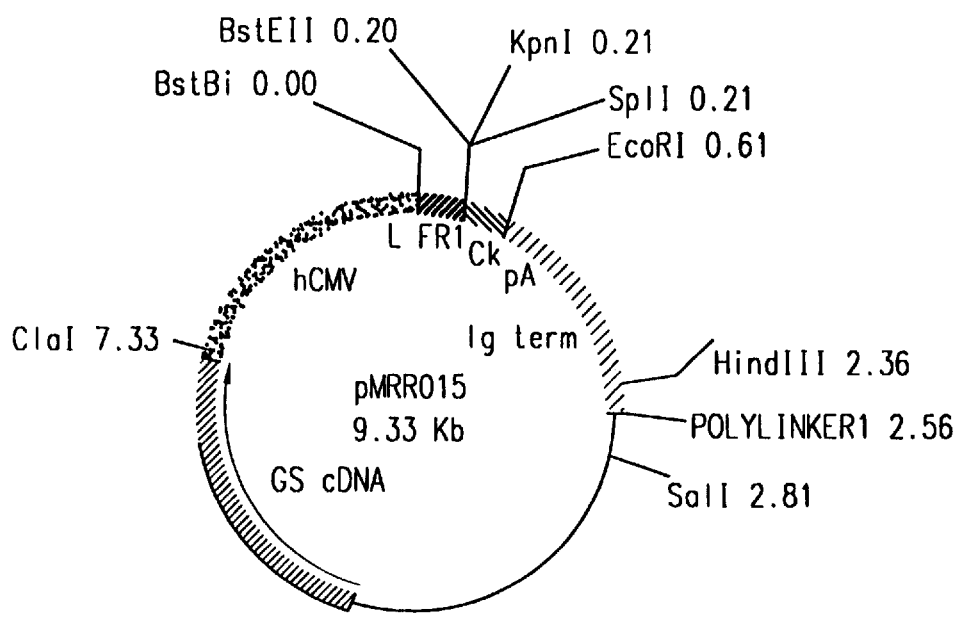
FIG. 6: Plasmid for insertion of h-P67.6 heavy chain.
Figure 7:
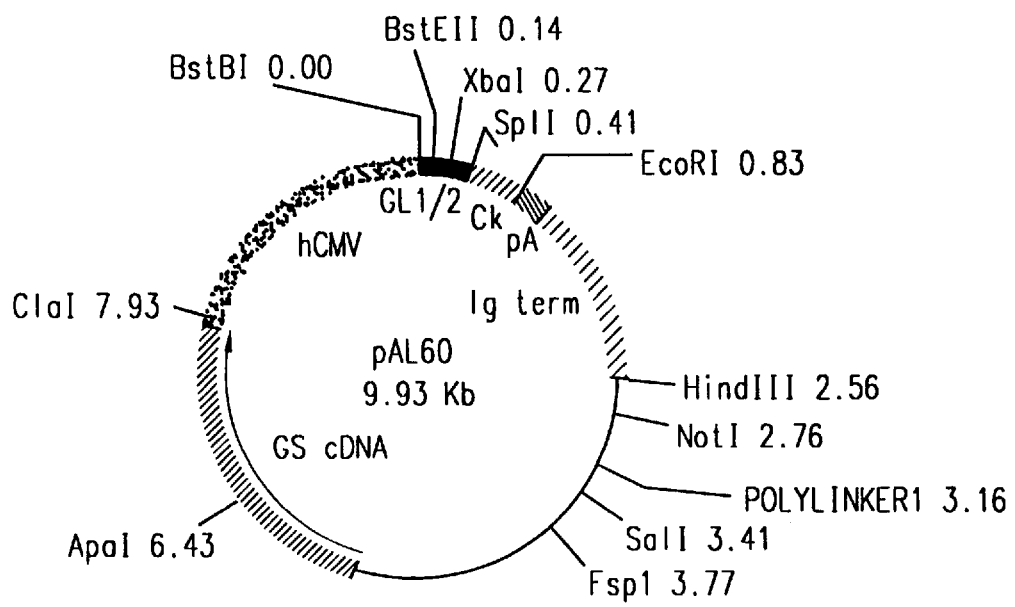
FIG. 7: Plasmid for h-P67.6 light chain expression.
Figure 8:
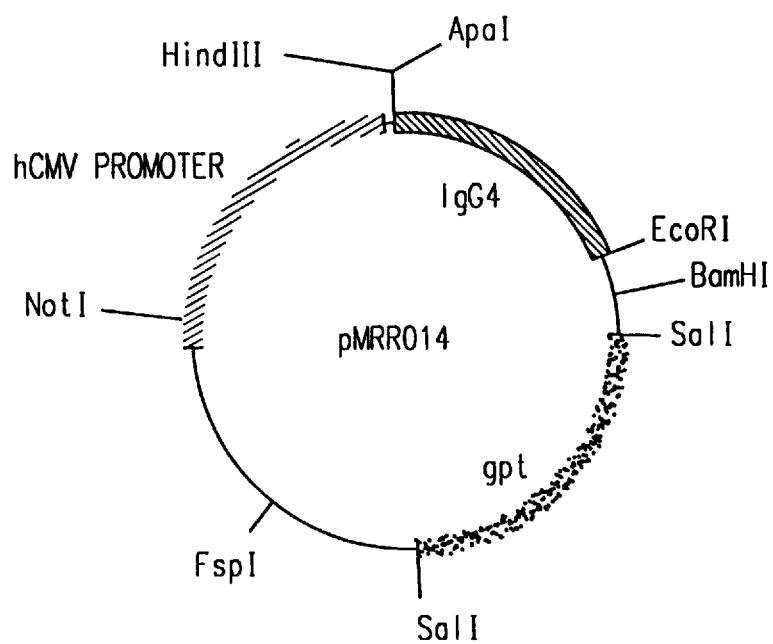
FIG. 8 is a schematic diagram of plasmid pMRRO14.

With reference to FIG. 1 and FIG. 2, the overlapping oligonucleotides that were synthesized (Oligo L1 through L8) are shown with double underlines, and the PCR assembly procedure (cf. WO 92/01059) was applied to these sequences. The CDR regions of the protein are designated with single underlines and other amino acids that were taken from the murine sequences are shown with a double underline. The restriction sites that were used to splice the sequences into plasmids are indicated at the beginning and end of the sequences. The variable portion of the heavy chain was cloned into plasmid pMRR14 (WO 93/06231) to give the plasmid designated pAL63 (FIG. 5) and the variable portion of the light chain was cloned into plasmid pMRR15 (FIG. 6) to give pAL60 (FIG. 7). Plasmids pMRR14 and pMRR15 contained the constant regions of the heavy and light chains, respectively, and therefore pAL63 and pAL60 contained complete sequences for the P67.6 heavy and light chains. Plasmid pMRR14 has an hCMV-MIE promoter, a polylinker site, and a nucleotide coding sequence which encodes the three constant domains of a human IgG4 antibody (FIG. 8). The plasmids were cotransfected into CHO-L761 cells to generate a h-P67.6 producing line from which the h-P67.6 was purified by standard methods. The resultant h-P67.6 bound to HL60 cells in competition with murine antibody with about a 50% loss in immunoaffinity. This binding was inhibited by pre-incubation with soluble CD33 antigen.

The antibody m-CT-M-01 is disclosed in E.P. 86 401482.4/0208615 and recognizes the polyepithelial mucin (PEM) antigen present on many human solid tumors, particularly breast, lung, and ovarian. The humanized version of this antibody, h-CT-M-01, is described in WO 93/06231 (1993). The procedures from WO 93/06231 which were employed to make h-CT-M-01 are as follows.

The DNA and predicted amino acid sequences for the unprocessed variable domains of the CTM01 heavy chain are shown in the Sequence Listing as SEQ ID NO: 7 and 8, respectively. The DNA and predicted amino acid sequences for the unprocessed variable domains of the CTM01 light chain are shown in the Sequence Listing as SEQ ID NO: 9 and 10, respectively. SEQ ID NO: 7 shows the sequence coding for the VH domain and SEQ ID NO: 8 shows the predicted amino acid sequence. The Leader Sequence for the heavy chain runs from residue 1 to residue 19 as shown in SEQ ID NO: 7. SEQ ID NO: 9 shows the sequence coding for the VL domain and SEQ ID NO: 10 shows the predicted amino acid sequence. The leader sequence for the light chain runs from residue 1 to residue 20 as shown in SEQ ID NO: 9. Examination of the derived amino acid sequences revealed considerable homology with other characterized immunoglobulin genes. The CTM01 MAb was confirmed to be an IgG1-kappa antibody.

Preparation of CDR-grafted Antibody Products

It was decided to use the EU human antibody framework (as defined by Kabat, E. A. et al., Sequences of Proteins of Immunological Interest, U.S. Dept. of Health and Human Services, NIH, USA, 1987 and Wu, T. T. and Kabat, E. A., J. Exp. Med., 132: 211–250 (1970) (hereinafter "Kabat references")) for carrying out the CDR-grafting. The strategy followed for CDR-grafting was as set out in International Patent Specification No. WO-A-91/09967, which is described above.

Two CDR-grafted heavy chains were designed. In the first, gH1, all three CDRs (as defined by the Kabat references) were changed to murine residues. In addition, residues 2, 37, 71, 73, 94, 103, 104, 105 and 107, which are outside the Kabat CDRs, were also changed to murine residues. In the second gH2, in addition to those murine residues in gH1, residues 48, 67 and 69 were changed to murine residues with a view to improving packing of the VH domain.

Two CDR-grafted light chains were also designed. In the first, gL1, all three CDRs (as defined by the Kabat references) were changed to murine residues. In addition, residues 3, 36, 63 and 108, which are outside the Kabat CDRs, were changed to murine resides. In the second, gL2, in addition to those murine residues in gL1, residues 37, 45 and 48 were changed to murine residues with a view to improving packing.

Figure 9:
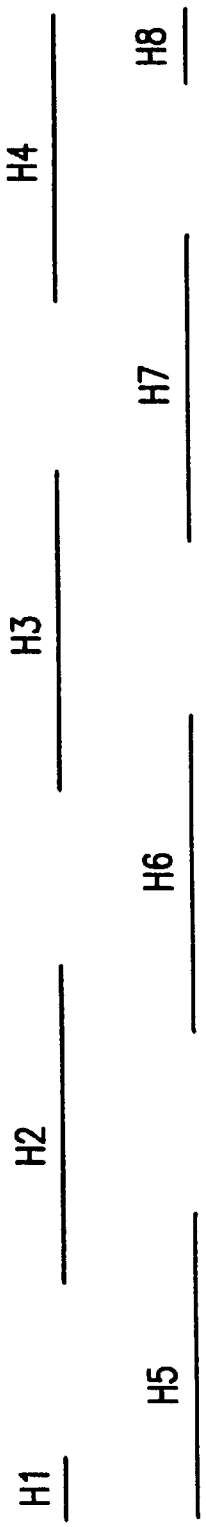
FIG. 9 shows the alignment of oligonucleotides H1 to H8 in the formation of the gH1 coding sequence.

A nucleotide sequence coding for the gH1 variable domain was produced by oligonucleotide assembly using oligonucleotides H1 to H8. The sequences for these oligonucleotides are given in the Sequence Listing under SEQ ID NOS: 11 to 18. The way in which these oligonucleotides are assembled to produce the gH1 coding sequence is shown in FIG. 9. The amino acid sequence coded for by this gH1 sequence is shown in the sequence listing under SEQ ID NO: 19.

A nucleotide sequence coding for the gH2 variable domain was also produced by oligonucleotide assembly using oligonucleotides H1, H2, H3A, H4, H5, H6A, H7 and H8. Oligonucleotide H3A differs from oligonucleotide H3 (SEQ ID NO: 13) in that residues 55 to 57 have been changed from GTG to GCA and residues 61 to 63 have been changed from ATT to CTG. Oligonucleotide H6A differs from oligonucleotide H6 (SEQ ID NO: 16) in that residues 70 to 72 have been changed from TAC to TAA. Thus, the gH2 variable domain encodes the same sequence as is shown under SEQ ID NO: 19, except that at residue 67, MET has been changed to ILE; at residue 87, VAL has been changed to ALA; and at residue 89, ILE has been changed to LEU.

A nucleotide sequence coding for the gL1 variable domain was produced by oligonucleotide assembly using oligonucleotides L1 to L8. The sequences for these oligonucleotides are given in the Sequence Listing under SEQ ID NOS: 20 to 27. The way in which these nucleotides are assembled is similar to that shown in FIG. 9 for the gH1 coding sequence (except that L is substituted for H). The amino acid sequence coded for by the assembled gL1 variable domain coding sequence is shown in the Sequence Listing under SEQ ID NO: 25.

A nucleotide sequence coding for the gL2 variable domain was produced by oligonucleotide assembly using oligonucleotides L1, L2A, L3A and L4 to L8. Oligonucleotide L2A differs from oligonucleotide L2 (SEQ ID NO: 21) in that residues 28 to 30 have been changed from CAG to GTA. Oligonucleotide L3A differs from oligonucleotide L3 (SEQ ID NO: 22) in that residues 25–27 have been changed from CAG to CTC, residues 49–52 have been changed from AAG to CAG and residues 59–61 have been changed from CAT to ATC. Thus, the gL2 variable domain encodes the same sequence as is shown under SEQ ID NO: 28, except that: at residue 23, Gln has been changed to Val; at residue 62, Gln has been changed to Leu; at residue 60, Lys has been changed to Gln; and at residue 73, Met has been changed to Ile.

For gene assembly 1 pmol of H2–H8 or L2–L7 was mixed with 10 pmol H1 and H8 or L1 and L8 in a 100 ml reaction with 5U Taq polymerase. A PCR reaction was done using 30 cycles (95° C., 1 min.; 50° C. 1 min; 72° C. 1 min). The resulting fragments were cut with HindIII and ApaI for VL with Bstb1 and SPII for VH.

Figure 10:
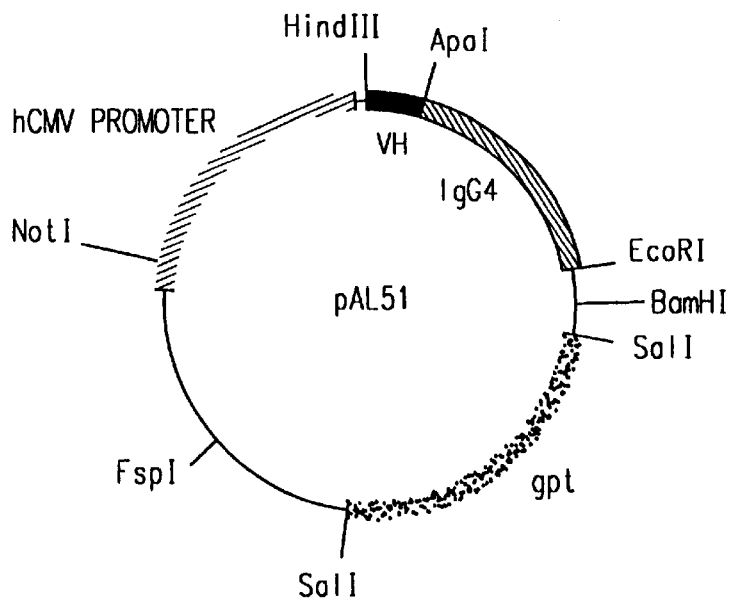
FIG. 10 is a schematic diagram of plasmid pAL51.
Figure 11:
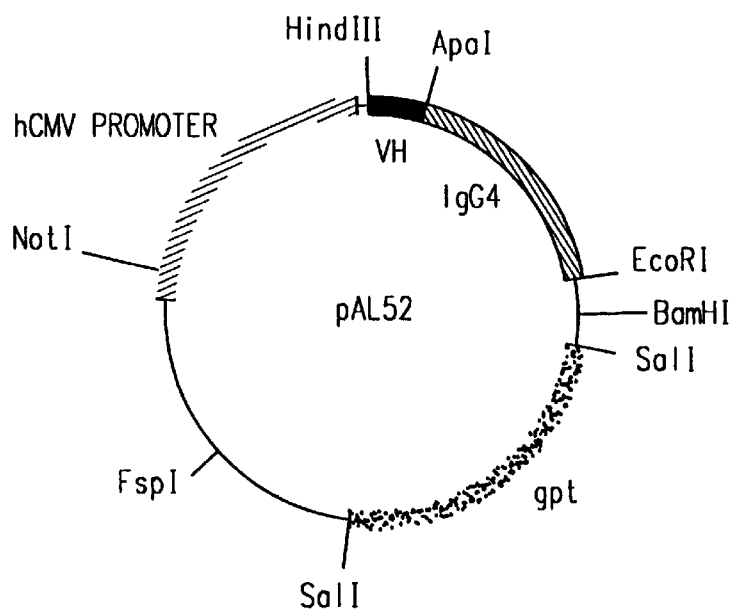
FIG. 11 is a schematic diagram of plasmid pAL52.

The nucleotide sequences coding for gH1 and gH2 were cloned as HindIII-ApaI fragments into plasmid pMRR014 (FIG. 8) to produce plasmids pAL51 and pAL52 (FIGS. 10 and 11, respectively).

Figure 12:
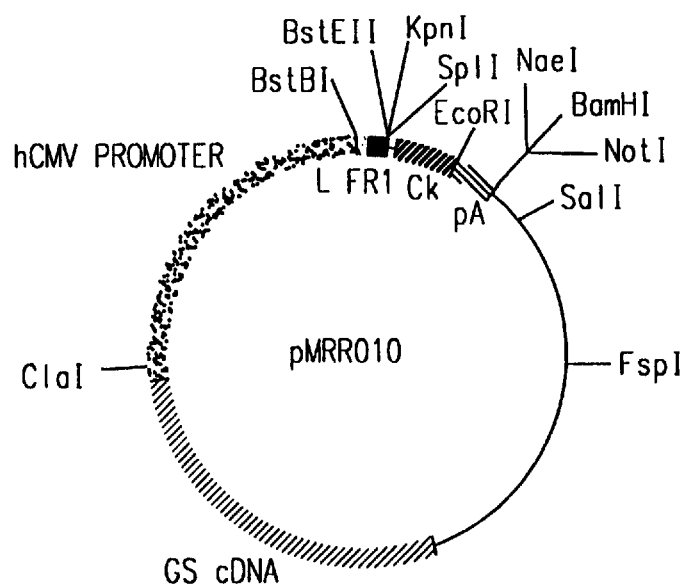
FIG. 12 is a schematic diagram of plasmid pMRRO10.
Figure 13:
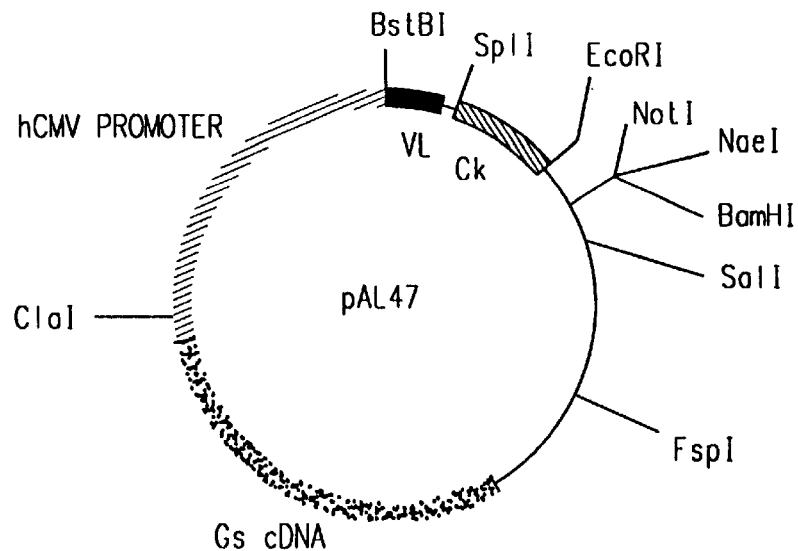
FIG. 13 is a schematic diagram of plasmid pAL47.
Figure 14:
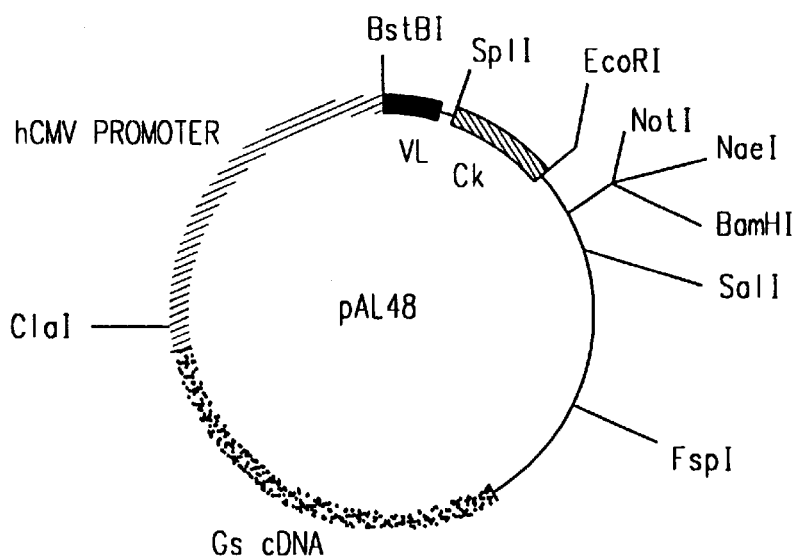
FIG. 14 is a schematic diagram of plasmid pAL48.

The nucleotide sequences coding for gL1 and gL2 were cloned as HindIII-ApaI fragments into plasmid pMRR010 (FIG. 12) to produce plasmids pAL47 and pAL48 (FIGS. 13 and 14, respectively).

Transient Expression of CDR-grafted/CDR-grafted Antibodies

The following pairs of plasmids: pAL47, pAL51; pAL47, pAL52; pAL48, pAL51; and pAL48, pAL52; were cotransfected into CHO-L761 cells.

Direct binding assays were carried out on the culture supernatants produced by the doubly transfected cell lines.

Figure 15:
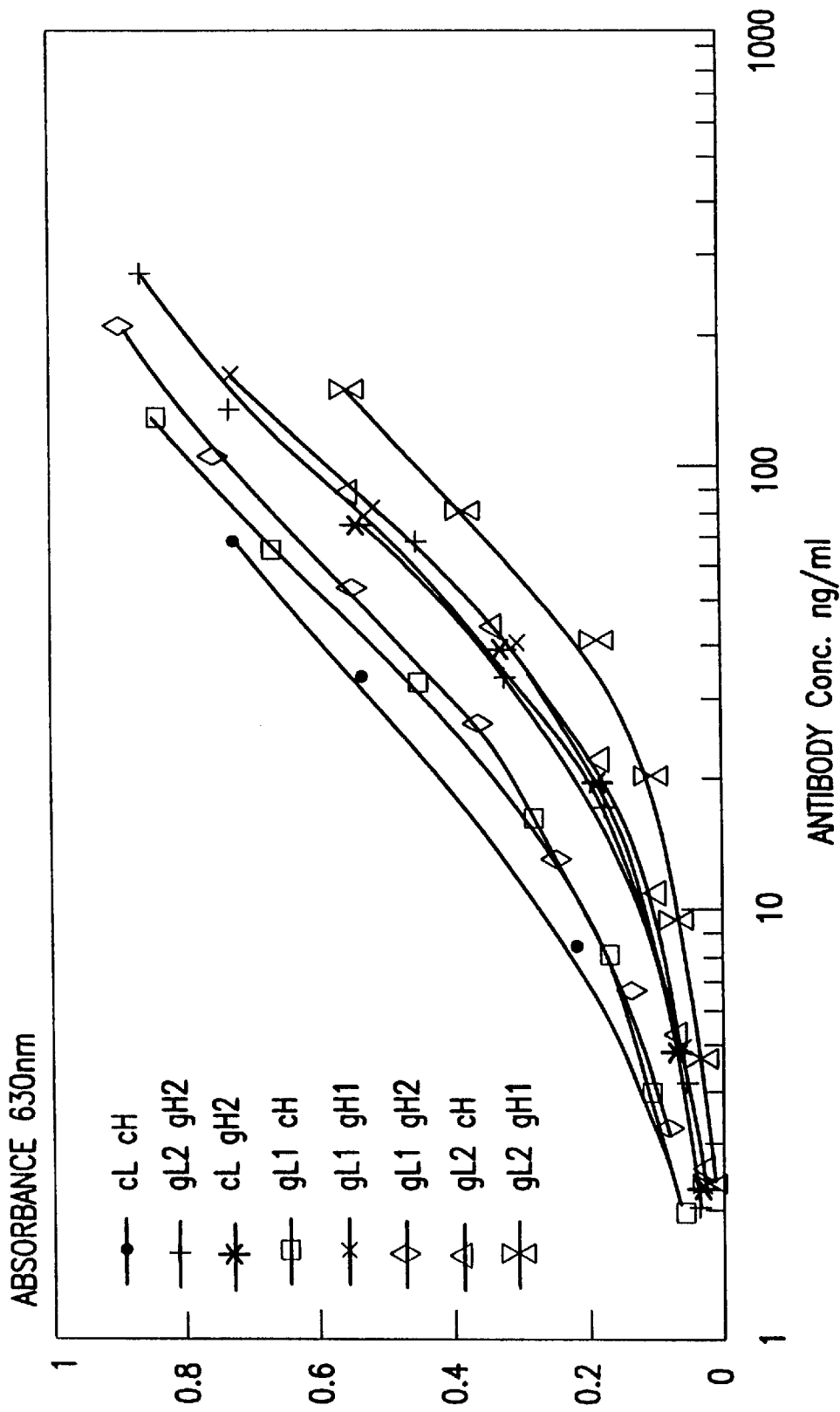
FIG. 15 is a graph of a direct binding ELISA on transiently expressed CDR-grafted antibodies.

The results of these assays are shown in FIG. 15, together with some results for chimeric/CDR-grafted antibodies.

From all the direct binding assays referred to above, it can be determined that the order of binding activity of the various antibodies produced by transient expression is as follows:

cLcH3>gL1ch=gL1gH2>cLgH2=gL2H2=gL1gH1=gL2cH>gL2gH1.

(wherein: cL=chimeric light chain;
cH=chimeric heavy chain;
gL1=CDR-grafted light chain with lowest number of amino acid changes;
gL2=CDR-grafted light chain with highest number of amino acid changes;
gH1=CDR-grafted heavy chain with lowest number of amino acid changes;
gH2=CDR-grafted heavy chain with highest number of amino acid changes).

The more active variants (CLcH, gL1cH, gL1gH2 and gL2gH2) together with the CTM01 MAb were tested in a competition enzyme immunoassay (EIA). Microwell plates were coated with PEM obtained as follows:

An affinity column was prepared by attaching the CTM01 MAb to a suitable chromatographic medium in a conventional manner. In a first method, pooled human urine samples were applied directly to the affinity column. In a second method, human milk was subjected to low speed centrifugation to separate the cream from skimmed milk. The skimmed milk was then subjected to high speed centrifugation to product an aqueous and a iipid component. The aqueous component was applied to the affinity column.

Once the affinity column was loaded, by either of the two methods, column fractions were eluted at high and low pHs, neutralized and assayed for reactivity with the CTM01 MAb. Fractions showing reactivity were pooled and dialyzed. The pooled fractions contained the polymorphic epithelial mucin (PEM) recognized by the CTM01 MAb.

The CTM01 MAb was biotinylated and was used to compete with the four variants referred to above. Bound biotinylated CTM01 MAb was revealed and quantified using a streptavidin-HRP conjugate and TMB.

Figure 16:
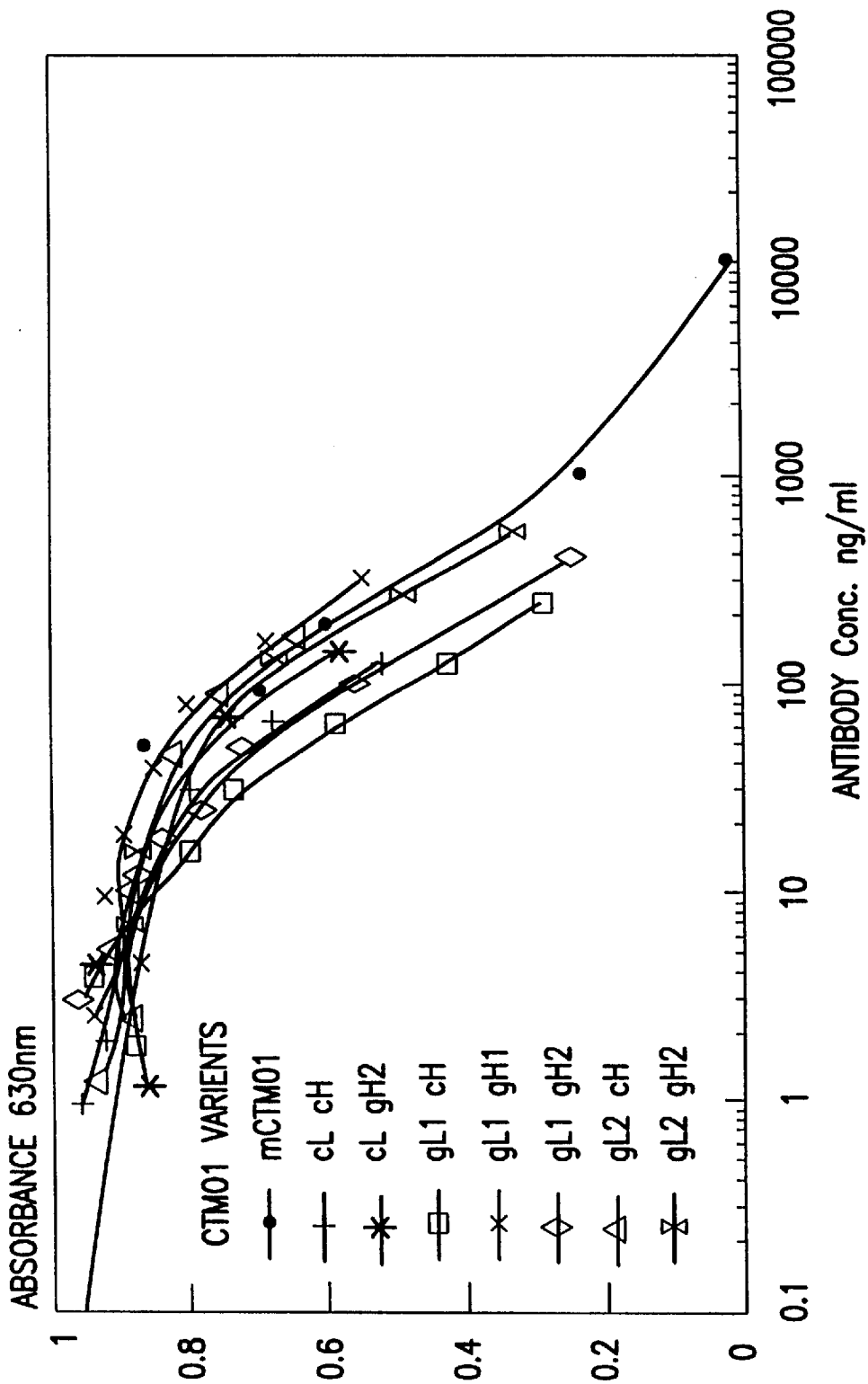
FIG. 16 is a graph of a competition EIA on transiently expressed chimeric and CDR-grafted antibodies.

The results of the competition EIA are shown in FIG. 16, which shows the same ranking of binding activity as set out above, except that the gL1cH combination shows greater activity than the cLcH combination.

It can thus be seen that CDR-grafted antibodies which recognize the same antigen as the CTM01 MAb have successfully been produced. The antibody m-A33 is disclosed in U.S. Pat. Nos. 5,160,723 and 5,431,897 and is a murine antibody which recognizes a glycoprotein antigen present on colon cancer cells. The humanized version of this antibody, h-A33, is disclosed in UK Patent Application 9,315,249.4. Examples of human frameworks which may be used to construct CDR-grafted humanized antibody molecules (HAMs) are LAY, POM, TUR, TEI, KOL, NEWM, REI and EU (Kabat, E. A. et al., Sequences of Proteins of Immunological Interest, U.S. Dept. of Health and Human Services, NIH, 1987) KOL and NEWM are suitable for heavy chain construction. REI is suitable for light chain construction and EU is suitable for both heavy chain and light chain construction. Preferably, however, the LAY framework is used as the human framework for both heavy and light chain variable domains in view of its high level of homology with MAb A33.

To demonstrate antigen binding both direct and competition ELISA format binding assays were used using solid phase anti-Fcg chain to capture the antibody. In the direct binding assay ASPC-1 or Colo205 cells were incubated at 4_C for 1 hour in the presence of various amounts of murine or humanized A33, or non-specific antibody controls. After washing the cells to remove unbound antibody, the presence of bound antibody was revealed by further incubation with FITC-labelled anti-murine or anti-human Fc and by detection in the FACScan analyzer (Becton Dickinson).

In competition format increasing amounts of the test antibody were coincubated with saturating amounts of FITC-labelled murine antibody and the ASPC-1 or Colo205 cells as above. After washing the cells to remove unbound antibody, the binding of the FITC labelled murine antibody to the cells was detected in the FACScan analyzer.

Cloning of A33 Variable Region Sequences

Murine A33 (IgG2a/k), (Welt, S., et al., J. Clin. Oncol. 8: 1894–1896 (1990)), was obtained from culture of 1.5 L of hybridoma supernatant. (ATCC, HB 8779). 32.5 mg was purified by Protein A Sepharose. This material was used as an assay standard and the separated heavy and light chains were subjected to N terminal sequencing.

The variable region sequences were obtained by the use of specific oligonucleotide primers (Jones and Bendig, Bio/Technology 9:88–89 (1990)), modified to allow cloning into Celltech expression vectors (see FIG. 17 and SEQ ID NOS: 29 to 53), to amplify sequences in cDNA derived from polyA+ mRNA from the A33 hybridoma. Sequence amplification was done using the Polymerase Chain Reaction (PCR, Saiki, R. K., et al., Science 230:1350–1354 (1985)), with denaturation, annealing and amplification conditions of 92° C, 1 minute; 55° C., 1 minute; 72° C., 1 minute, with 30 cycles of amplification, and using the Taq Polymerase (Perkin Elmer-Cetus). 100 ng of first strand cDNA synthesized using the Amersham International cDNA synthesis kit, and 10 pmoles of oligonucleotide primers were used in a 100 mL reaction volume.

Figure 18A:
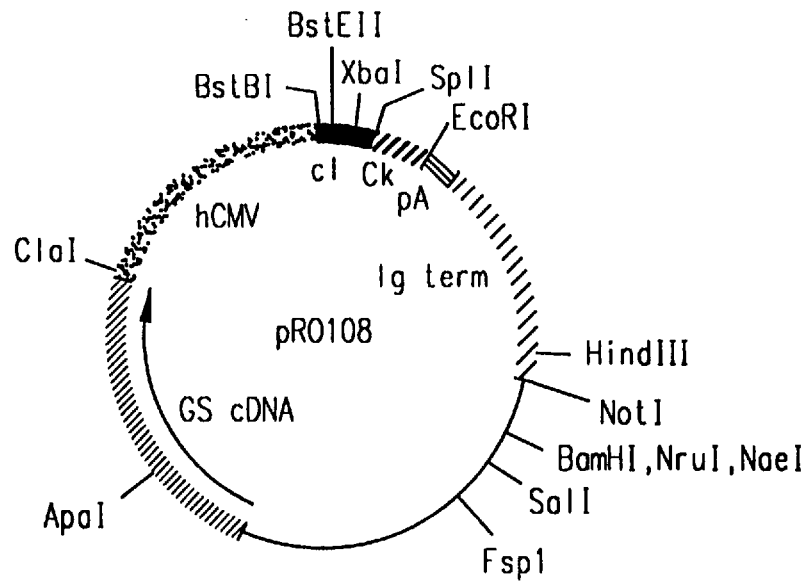
FIG. 18A–B are schematic diagrams of the chimeric A33 expression vectors.
Figure 18B:
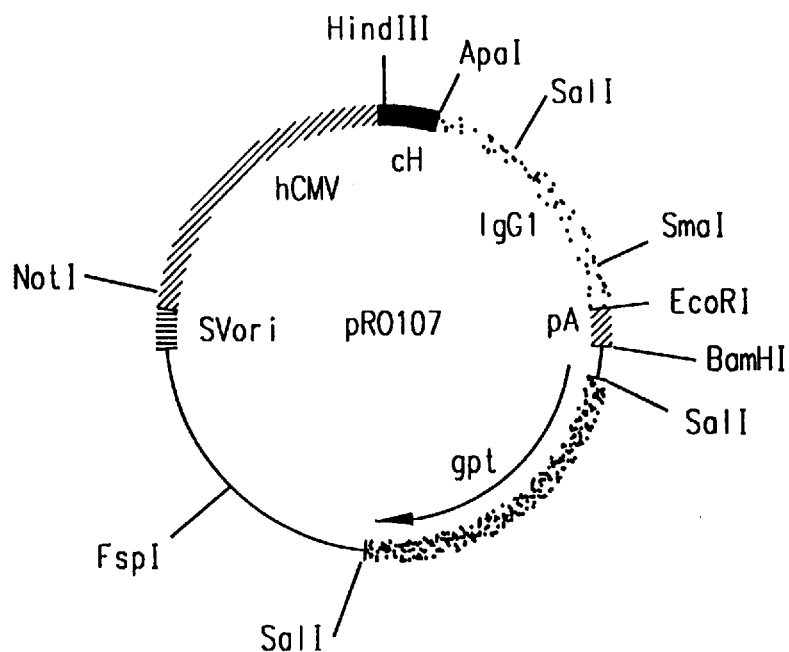

The PCR amplified products were cleaved with BstBI and SpII for the light chain and HindIII and ApaI for the heavy chain. These fragments were cloned into the human kappa light chain acceptor vector, pMRR15.1, and the human heavy chain, IgG1, acceptor vector, pMRR011, respectively, to give chimeric expression vectors pRO108 for the light chain (FIG. 18) and pRO107 for the heavy chain (FIG. 18), respectively.

For each plasmid the variable regions from four independent clones were sequenced. For both variable regions the DNA sequence between the priming regions was the same in each of the four clones. Within the priming region sequence variability was seen, derived from the redundancy in the sequences of the primers used. For both heavy and light chains, the deduced amino acid sequences obtained for the first 11 residues of the mature variable domain were in agreement with the results of N terminal peptide sequencing of the murine antibody.

The DNA sequences were further confirmed by a second PCR experiment using forward primers that anneal in framework 1 (Orlandi, R., et al., Proc. Natl. Acad. Sci. USA 86:3833–3837 (1989)). The sequences obtained (SEQ ID NOS: 54 and 56) agreed with those found in the first experiment. The amino acid sequences of the A33 light and heavy chain variable regions are shown in FIG. 19 and SEQ ID NOS: 55 and 57.

Design of Humanized A33

The murine variable regions of A33 were humanized according to the strategy described in Adair et al., (1991), and by reference to other recently published data on antibody humanization (Co, M. S., et al., Proc. Natl. Acad. Sci. USA 88:2869–2873 (1991)). The $V_H$ of A33 shows closest homology (70%) to the consensus sequence of human subgroup $V_H$III, while the $V_L$ shows greatest homology to the consensus sequence of $V_L$I and $V_L$IV (62%). From these subgroups LAY, which has a $V_H$III heavy chain and $V_L$I light chain, was chosen as the human framework. For the light chain residues 1–23, 35–45, 47–49, 57–86, 88 and 98–108 inclusive were derived from the LAY sequence, (numbering as in Kabat et al., 1987) and the residues 24–34, 46, 50–56, 87 and 89–97 inclusive were derived from the murine sequence. Residues 24–34, 50–56 and 89–97 correspond to the Complementarity Determining Regions (Kabat et al., 1987)(see FIG. 20). Residues 46 and 87 are predicted to be at the interface of the light and heavy variable regions. Residue 46 is usually a leucine. Residue 87 is usually either a phenylalanine or tyrosine.

For the heavy chain residues 2–26, 36–49, 66–71, 74–82a, 82c-85, 87–93 and 103 to 113 inclusive were derived from the LAY sequence while residues 1, 27–35, 50–65, 72, 73, 82b, 86 and 94–102 inclusive were derived from the murine sequence (see FIG. 21). Residues 31–35, 50–65 and 95–102 in the heavy chain correspond to the Complementarity Determining Regions (Kabat et al., 1987). The murine derived amino acids in the framework regions were included for the following reasons. Residue 1 is usually solvent accessible and in the vicinity of the CDR region. LAY has a residue, alanine, not normally found at this position in human or murine $V_H$ sequences and therefore the murine residue was used. At positions 72 and 73 the murine residue was used because of the predicted proximity to CDR2 and also, in the case of residue 72, to remove the possibility of introducing an N-linked glycosylation site into the variable domain by the use of the LAY framework (see also Co, M. S., et al., Proc. Natl. Acad. Sci. USA 88:2869–2873 (1991); European Patent Application No. 0438310 ("Law et al., 1991")). The murine sequence was also used at the interdomain residue 94, where A33 has a proline, not normally found at this position. Murine residues were used at positions 82b and 86 because the use of the human amino acids at these positions in a humanized antibody with LAY frameworks have previously been found to be deleterious for the expression of the heavy chain (International Patent Specification No. WO 92/010509).

Construction of Humanized A33 and Expression in Cho Transients

Figure 22:
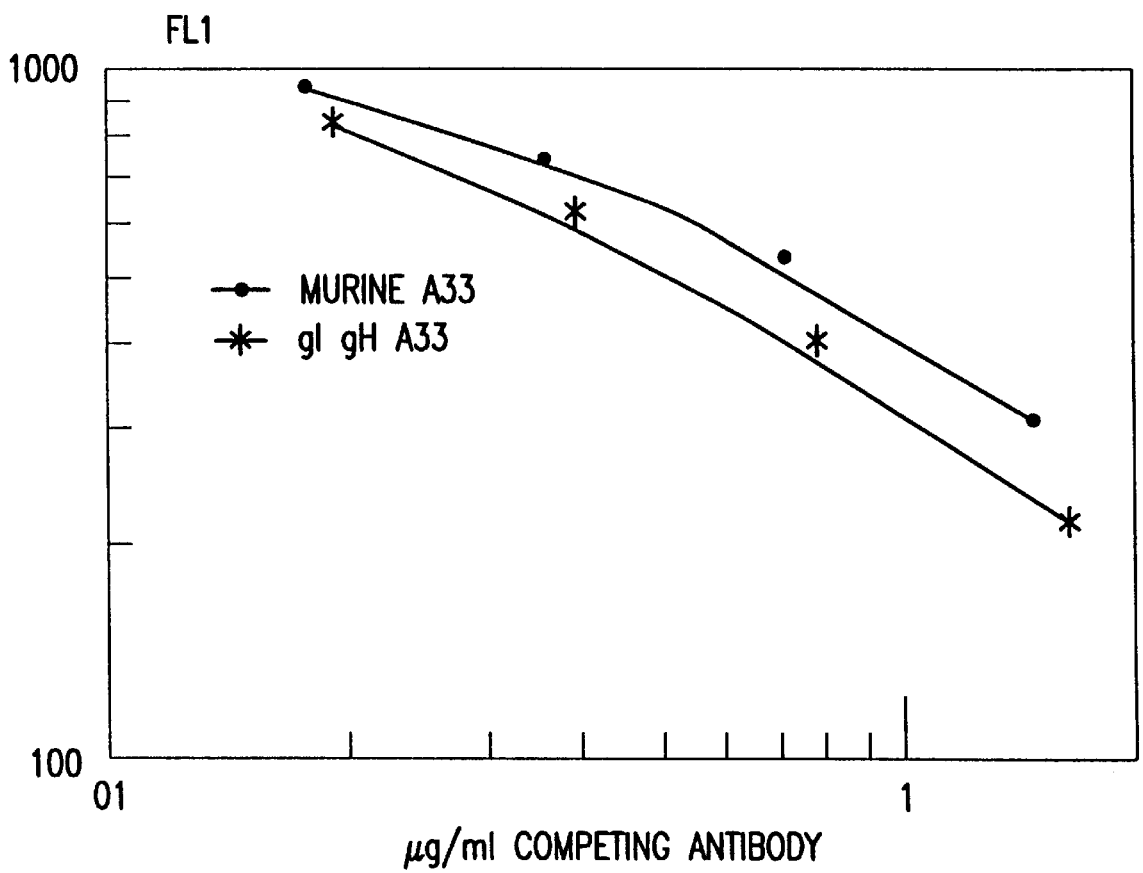
FIG. 22 is a graph of a competition binding assay. Murine A33 and humanized A33 prepared from CHO-K1 transient expression experiments were used to compete for binding to Colo205 cells with FITC-labeled murine A33. Residual FITC-mA33 bound to cells was measured in a FACScan analyzer and fluorescence (Y axis) was related to input unlabeled antibody (X axis).

The humanized variable regions were assembled from overlapping oligonucleotides using a PCR assembly procedure (International Patent Specifications Nos WO 92/010509 and WO 92/011383, also Daugherty, B. L., et al., Nucl. Acids Res. 19:2471–2476 (1991); Law et al. 1991). The oligonucleotides are given in FIG. 20 (SEQ ID NOS: 58 to 65) for the light chain and FIG. 21 (SEQ ID NOS: 66 to 73) for the heavy chain. The oligonucleotides were assembled using either 1 pmole of the longer internal oligonucleotides for the heavy chain variable region or 0.01 pmole for the light chain, with 10 pmole of the shorter terminal oligonucleotides in both cases. The reaction conditions were 30 cycles of 92° C., 1 minute; 55° C. 1 minute; 72° C. 1 minute using Taq polymerase. The PCR products were digested with the appropriate restriction enzymes as described for the chimeric antibody constructions and cloned into pMRRO15.1 for the light chain, and pMRR011 for the heavy chain to give pCG16 and pRO109 respectively.

pRO 108 (CL expression vector) and pCG 16 (hL expression vector) were each co-transfected with pRO107 (cH expression vector) or pRO109 (hH expression vector) into CHO L761h cells, and the antibody in the culture supernatant was calibrated and shown to compete for binding with FITC-labelled murine A33 for antigen on Colo205 cells by FACScan analysis (FIG. 22). The relative potency of the fully humanized antibody was calculated to be 75% of that of the murine antibody based on the competition $IC_{50}$ values.

Construction of Stable Cell Lines in NSO for hA33 (γ1), hFab'(γ4Δcys)

Expression vectors based on the GS amplification system (Bebbington, C. R., et al., Bio/Technology 10:169–175 (1992); European Patent Specification No. 256055) were constructed for the humanized A33 and also for a vector capable of producing a humanized Fab'(γ4Δcys) fragment.

The humanized A33 expression vector pAL71 (FIG. 23), capable of coexpressing both hL and hH chains, was constructed by obtaining a Not1-BamH1 vector fragment from pCG16 which contains the shuttle vector sequences, the GS cDNA selectable marker, a copy of the hCMV-MIE promoter/enhancer 5' to the humanized light chain which is followed by the SV40 polyadenylation sequences and the Ig terminator sequence. This vector fragment was combined with the Not1-BamH1 fragment from pRO109 which contains the humanized A33 (γ1) heavy chain between the hCMV/MIE promoter/enhancer and the SV40 polyadenylation sequences.

The heavy chain fragment which combines with light chain to give an antibody Fab' fragment consists of the heavy chain variable domain, the CH1 domain and the hinge sequence (or derivative hinge sequence) and is known as the Fd' fragment. A modified Fd' sequence, in which the hinge sequence has been altered to substitute one of the cysteines for alanine, and so reduce the number of hinge cysteines to one is described in Bodmer, M. W., et al., International Patent Specification No. WO 89/01974 (1989) and is known as the Fd'(γ4ΔCys) sequence.

An expression vector capable of producing A33 hL and A33 hH-Fd'(γ4ΔCys), pAL72 (FIG. 23), was constructed by combining the Not1-BamH1 vector fragment from pCG16 with the Not1-Apa1 fragment from pRO109, which encodes the hCMV-MIE promoter/enhancer 5' to the humanized A33 heavy chain variable region, along with IgG4 CH1 and hinge(DCys) sequences and SV40 polyadenylation sequences on an Apa1-BamH1 fragment derived from the expression vector pAL49 (International Patent Specification No. WO 92/010509).

Plasmids pGR50, pAL71, and pAL72 were linearized with Pvu1 for pGR50, or Fsp1 for pAL71 and pAL72, and 50 mg of DNA was used to transfect $10^7$ NSO cells, by electroporation, using 1500 V and 3 mF with 2×1 second pulses. The cells were distributed into 96 well dishes at $5 \times 10^5$ cells in 50 mL per well in CB2 medium supplemented with 10% dialyzed, heat inactivated, fetal calf serum (10% of dFCS) and 2mM glutamine. After 24 hours at 37° C., 5% $CO_2$ a further 100 mL of CB2 medium containing 10% dFCS, supplemented with 10 mM methionine sulphoximine (MSX) was added to each well. The cells were incubated for 2–3 weeks. Discrete colonies were observed after 19 days of culture. Culture supernatants were harvested from wells containing single colonies and antibody producing colonies were expanded for estimation of specific production rates (SPR) as picograms (pg) of antibody produced per cell, per 24 hours of culture. The cell lines with the highest SPR values were taken for further analysis. Cell stocks were frozen and the cell lines were grown in by transfer into MM1 medium containing<1% dialyzed fetal calf serum, to produce culture supernatants for antibody purification. Some loss of productivity was seen initially with the cIgG1 and hIgG1 cell lines but after culture in MM1 the productivity of the cell lines stabilized.

The highest producing cell lines were for the 8D3 (cA33 (γ1), SPR of 33 pg/cell/24 hours, accumulated yield of 35 mg/L from small scale culture, HC86.7 (hA33(γ1), SPR of 3 pg/cell/24 hours, accumulated yield of 36 mg/L from small scale culture and HC87.21 (hA33 Fab'(γ4Δcys), SPR of 50 pg/cell/24 hours, accumulated yield of 112 mg/L from small scale culture and 170 mg/L from 15 L scale fermentation).

Anti-Tac is disclosed in T. A. Waldman et al., "J. Immunol." 126, 1393 (1981) and is a murine antibody reactive with the IL-2 receptor that is found on activated and functionally mature T cells, including abnormally activated leukemia cells. The procedure for making the Anti-Tac antibody described by T. A. Waldman et al. is as follows:

Production of Anti-Tac Monoclonal Antibody

Cells used for immunization. Cells used for immunization were human cultured T cells (Called CTC 16) that were derived from peripheral blood T cells from a patient with mycosis fungoides and that were continuously growing in the presence of T cell growth-promoting factors contained in the conditioned medium from phytohemagglutinin(PHA)-stimulated lymphocyte cultures (Uchiyama, T., et al., "Immunoregulatory functions of cultured human T lymphocytes," (1980) Trans. Assoc. Am. Phys.; Morgan, D. A., et al., (1976) Science 193:1007). CTC 16 had been in culture for 172 days when they were injected into mice. Cell surface marker analysis showed that more than 95% of these CTC formed spontaneous rosettes with sheep erythrocytes and reacted with the heteroantiserum to 1a (anti P23, Sarmiento, M., et al., (1980) Proc. Natl. Acad. Sci. 77:1111).

Immunization and hybridization. An eight week old female BALB/c mouse was immunized i.v. on 2 occasions, with a three week interval, with $1 \times 10^6$ viable CTC 16 cells in 0.2 ml of RPMI 1640 culture medium (GIBCO, Grand Island, N.Y.). Cell fusion was performed at 3 days after the 2nd injection of CTC 16. Spleen cell suspensions were obtained by gentle teasing of the spleen and lysis of red blood cells with ACK lysing butter ($NH_4Cl$, $KHCO_3$, EDTA, and distilled water). Cell fusion was carried out according to the method of Kohler and Milstein (Nature 256:495 (1975)) and of Gefter et al. (Somatic Cell Genet. 3:231 (1977)) with a slight modification (Ozato, K., et al., (1980) J. Immunol. 124:533). One hundred and fifty million spleen cells were fused with $3 \times 10^7$ NS-1 mouse myeloma cells, using 30% polyethylene glycol (MW 1000, Baker, Phillipsburg, N.J.) dissolved in Dulbecco's modified Eagle's medium (GIBCO). Fused cells were resuspended in 60 ml of Dulbecco's modified Eagle's medium containing 10% NCTC 109 medium (Microbiological Associates, Walkersville, Md.), 15% heat-inactivated fetal calf serum (FCS), 2 mM glutamine, 1% nonessential amino acid solution 100× (GIBCO), 0.2 U/ml crystalline bovine insulin (Sigma Chemical Co., St. Louis, Mo.), 1 mM oxaloacetic acid (Sigma), 0.5 mM sodium pyruvate (Sigma), 50 U/ml penicillin, and 50 μg/ml streptomycin. Cells were distributed into flat-bottom microtiter plates (Falcon Plastics, Oxnard, Calif.) at a concentration of $2.5 \times 10^5$ immune cells in 0.1 ml per well and were cultured at 37° C. with 7% $CO_2$ in a humid atmosphere. Hybridoma cells were selected by feeding with HAT medium containing 0.1 mM hypoxanthine, 0.4 μM aminopterin, and 16 μM thymidine.

Screening for reactivity of hybridoma culture supernatants. Fifteen days after cell fusion, the culture supernatants from wells with cell growth were tested for their antibody activity by a complement-dependent cytotoxicity test. CTC 16 and an Epstein-Barr virus (EBV) transformed B cell line (16B), both of which were derived from the same patient, were labeled with $^{51}Cr$ sodium chromate (Amersham Searle, Arlington Heights, Ill.), and were used as target cells. Fifty μl of hybridoma culture supernatants and 50 μl of target cells at the concentration of 5×10$^5$/ml were mixed in round-bottom microtiter plates (Linbro Scientific Inc., Hamden, Conn.) and incubated at 37° C. for 30 min; then 25 μl of appropriately diluted neonatal rabbit serum as a complement source was added. After another 60 minute incubation at 37° C., the supernatants were collected by a Titertek supernatant Collecting System (Flow Laboratory Inc., Rockville, Md.) and counted with a gamma counter. Specific cytotoxicity was calculated as follows:

Specific cytotoxicity(%) = 100 ×

$$\frac{\text{(Observed }^{51}\text{Cr release with antibody and }C - \text{Spontaneous }^{51}\text{Cr release with }C)}{\text{(Maximal }^{51}\text{Cr release with detergent} - \text{Spontaneous }^{51}\text{Cr release with }C)}$$

Cloning and production of a hybridoma antibody. After screening, hybridoma cultures that showed cytotoxic activity against CTC 16 but not 16B were expanded and cloned by a limiting dilution method. Irradiated (2000 R) rat fibroblasts (Flow Laboratory, McLean, Va.) were used as a feeder layer. Fourteen days later, when hybridoma clones had been expanded, the supernatants were tested again for their cytotoxic activity against the same target cells, using the $^{51}$Cr release cytotoxicity test, and 1 clone-producing antibody reactive with CTC 16 but not 16B was selected and expanded. These cloned hybridoma cells were cultured in 250-ml plastic culture flasks. Supernatants were collected when the cell concentration was between 5×10$^5$ and 9×10$^5$/ml. Culture supernatants obtained on a particular day were used in these studies. In order to obtain ascites containing large quantities of antibodies, 2×10$^5$ hybridoma cells were injected i.p. into BALB/c mice primed with pristane (Aldrich Chemical Co., Milwaukee, Wis.). The monoclonal antibody studied was demonstrated to be of the mouse IgG2a subclass by the positive immunoprecipitation reaction in agarose of ascites fluid with goat anti-mouse IgG2a.

The two basic types of conjugates disclosed in U.S. Pat. No. 5,053,394 are those which are attached to lysine residues of the antibody and those which are attached to the oxidized carbohydrate residues using the method taught in U.S. Pat. No. 4,671,958. Lysine attachment as it is disclosed in U.S. Pat No. 5,053,394 produces conjugates which are stable to hydrolysis under normal physiological conditions. The carbohydrate-based conjugates, which involve the formation of a hydrazone from a hydrazide or similar derivative, are hydrolytically unstable under certain conditions, and that is in many cases an advantage. Some instability is often needed to allow release of the drug once the conjugate has been internalized into the target cell, but a certain degree of stability is important to prevent premature release of the drug from the antibody. However, these carbohydrate-based conjugates suffer from various drawbacks. First, it is necessary to use periodate to generate aldehydes from the carbohydrate residues of the antibody. Antibodies contain cysteines, cystines, methionines, tryptophans, or tyrosines residues which are necessary for proper functioning of the antibody. However, these same amino acids can be sensitive to periodate oxidation, and if such oxidation takes place to an amino acid which either is part of the antigen binding site of the antibody or a structurally important region near the antigen binding site, its immunoaffinity can be significantly diminished. A second drawback of using the carbohydrates for conjugation is the variability of the hydrazones and related structures that are generated from the naturally-occurring sugars and the hydrazide derivative. Not only are the hydrazones subject to different rates of hydrolysis due to differences in their local structure, but other structures, such as hydrated species, piperadines, etc. can also be generated. Any one conjugate may contain structures that are either too stable or too labile for optimum activity.

Limited examples of how to combine some of the properties of the carbohydrate-based conjugates and the lysine-based conjugates have appeared using other less potent classes of anticancer agents. Cullinan in U.S. Pat. No. 5,006,652 and 5,094,849 teaches that certain bifunctional compounds containing both carboxylic acid and aldehyde or keto functionality can be used as spacers between the lysines of antibodies and hydrazide derivatives of the Vinca alkaloids, while Johnson in U.S. Pat. No. 5,028,697 and 5,144,012 teaches similar art for methotrexate analogs. Sinam et al. also disclose similar constructs in WO Pat. No. 90/03401. In none of these cases is it demonstrated that this method is useful for preparing conjugates of the methyltrisulfide antitumor antibiotics, especially the calicheamicins or esperamicins. The cited patents do not demonstrate that these constructs made with either the Vinca alkaloids, the methotrexate analogs, or other agents are superior in their biological profile to conjugates made using lysine-based or carbohydrate-based conjugates.

The present invention describes a series of conjugates prepared from the potent methyltrisulfide antitumor antibiotics made with an improved linker system that gives conjugates which in many cases are vastly superior biologically to conjugates of the same drugs made by other methods.

DETAILED DESCRIPTION OF THE INVENTION

The conjugates of this invention use linkers that can be added to a derivative of a drug, particularly hydrazides and related nucleophiles, prepared from the methyltrisulfide containing antitumor antibiotics. The linkers require a carbonyl group on one end for formation of a Schiff's base, particularly a hydrazone, and a carboxylic acid on the other end. The carboxylic acid can be activated and subsequently reacted with the lysines of an antibody or other targeting protein or with an amine, alcohol, or other appropriate nucleophile on other targeting agents which have been chosen for their ability to target undesired cell populations. These constructs, which for antibodies contain elements of both the lysine-based conjugates and the carbohydrate-based conjugates, not only overcome the disadvantages of previously disclosed constructs, but have the additional advantage that they can be fine-tuned by varying the structure of the linker to "design in" the optimum amount of hydrolytic stability/instability. This can result in maximum toxicity to the target cells with minimal toxicity to the non-target cells. The optimum hydrazone stability/instability is not necessarily the same for each drug and targeting agent combination.

The method of constructing the conjugates described in this patent produces conjugates of the methyltrisulfide antitumor antibiotics which are unexpectedly stable relative to the carbohydrate based conjugates without loss of activity. In some cases, the conjugates are 100 times more potent than the corresponding conjugates made by the carbohydrate-based method and, in addition, show reduced cytotoxicity against non-target cell lines. This results in conjugates with up to 10,000-fold selectivity between target and non-target cell lines.

The linkers required for the construction of these conjugates can be represented by the following formula:

$Z^3$[CO-Alk$^1$-Sp$^1$-Ar-Sp$^2$-Alk$^2$-C(Z$^1$)=Z$^2$]$_m$

Alk$^1$ and Alk$^2$ are independently a bond or branched or unbranched (C$_1$–C$_{10}$) alkylene chain. Sp$^1$ is a bond, —S—, —O—, —CONH—, —NHCO—, —NR'—, —N(CH$_2$CH$_2$)$_2$N—, or —X—AR'—Y—(CH$_2$)$_n$—Z wherein n is an integer from 0 to 5, X, Y, and Z are independently a bond, —NR'—, —S—, or —O—, and AR' is 1,2-, 1,3-, or 1,4-phenylene optionally substituted with one, two, or three groups of (C$_1$–C$_5$) alkyl, (C$_1$–C$_4$) alkoxy, (C$_1$–C$_4$) thioalkoxy, halogen, nitro, COOR', CONHR', O(CH$_2$)$_n$COOR', S(CH$_2$)$_n$COOR', O(CH$_2$)$_n$CONHR', or S(CH$_2$)$_n$CONHR' wherein n is as hereinbefore defined, with the proviso that when Alk$^1$ is a bond, Sp$^1$ is also a bond. R' is a branched or unbranched (C$_1$–C$_5$) chain optionally substituted by one or two groups of —OH, (C$_1$–C$_4$) alkoxy, (C$_1$–C$_4$) thioalkoxy, halogen, nitro, (C$_1$–C$_3$) dialkylamino, or (C$_1$–C$_3$) trialkylammonium—A$^-$ where A$^-$ is a pharmaceutically acceptable anion completing a salt. Sp$^2$ is a bond, —S—, or —O—, with the proviso that when Alk$^2$ is a bond, Sp$^2$ is also a bond. Z$^3$ is a hydroxyl group, and m is 1.

The groups Alk$^1$, Sp$^1$, Alk$^2$ and Sp$^2$ in combination, as well as the group Ar discussed below, allow for spacing of the carbonyl group from the carboxylic acid. Furthermore, Alk$^1$ and Sp$^1$ can influence the reactivity of the carboxyl group both during and after it has been activated. When Alk$^2$ and Sp$^2$ together are a bond, the Sp$^1$ group also influences the reactivity of the carbonyl group on the other end of the linker and the stability of the product formed from reactions at that carbonyl. The group R' can be used to influence the solubility and other physiochemical properties of these compounds. A preferred embodiment for Alk$^1$ is (C$_2$–C$_5$) alkylene, and for Sp$^1$ is an oxygen atom. A preferred embodiment for the groups Alk$^2$ and Sp$^2$ together is a bond.

With reference to the structure shown above, the group z$^2$ is an oxygen atom. The group Z$^1$ is H, (C$_1$–C$_5$) alkyl, or phenyl optionally substituted with one, two, or three groups of (C$_1$–C$_5$) alkyl, (C$_1$–C$_4$) alkoxy, (C$_1$–C$_4$) thioalkoxy, halogen, nitro, COOR', CONHR', O(CH$_2$)$_n$COOR', S(CH$_2$)$_n$COOR', O(CH$_2$)$_n$CONHR', or S(CH$_2$)$_n$CONHR', wherein n and R' are as hereinbefore defined. The group Z$^1$ has a pronounced effect on the reactivity of the carbonyl group and on the stability of the products formed from reactions at the carbonyl. When Z$^1$ is aryl and the product is, for example, a hydrazone, the hydrazone is relatively stable; when Z$^1$ is hydrogen, then an intermediate level of stability is obtained, and when Z$^1$ is (C$_1$–C$_6$) alkyl, relatively less stable hydrazones are formed. As stated earlier, stability is important to prevent premature release of the drug from the antibody, but some instability is needed to allow release of the drug once the conjugate has been internalized into target cells. A preferred embodiment for the Z$^1$ group is (C$_1$ to C$_3$).

The group Ar is 1,2-, 1,3-, or 1,4-phenylene optionally substituted with one, two, or three groups of (C$_1$–C$_6$) alkyl, (C$_1$–C$_5$) alkoxy, (C$_1$–C$_4$) thioalkoxy, halogen, nitro, COOR', CONHR', O(CH$_2$)$_n$COOR', S(CH$_2$)$_n$COOR', O(CH$_2$)$_n$CONHR', or S(CH$_2$)$_n$CONHR' wherein n and R' are as hereinbefore defined or a 1,2-, 1,3-, 1,4-, 1,5-, 1,6-, 1,7-, 1,8-, 2,3-, 2,6-, or 2,7-naphthylidene or

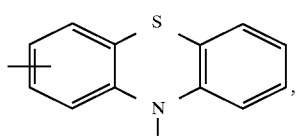

wherein Sp$^1$ a bond only connected to the nitrogen of the phenothiazine, each optionally substituted with one, two, three, or four groups of (C$_1$–C$_6$) alkyl, (C$_1$–C$_5$) alkoxy, (C$_1$–C$_4$) thioalkoxy, halogen, nitro, or COOR', CONHR', O(CH$_2$)$_n$COOR', S(CH$_2$)$_n$COOR', O(CH$_2$)$_n$CONHR', or S(CH$_2$)$_n$CONHR' wherein n and R' are as hereinbefore defined;

The choice of Ar has a significant influence on the stability of the products derived from the carbonyl when Alk$^2$ and Sp$^2$ are together a bond. Both the relative position of Sp$^1$ and Sp$^2$ as well as the presence of additional substituents on Ar can be used to fine-tune the hydrolytic behavior of the product formed from the carbonyl. A preferred embodiment for Ar is 1,2-, 1,3-, or 1,4-phenylene, or 1,2-, 1,3-, 1,4-, 1,5-, 1,6-, 1,7-, 1,8-, 2,3-, 2,6-, or 2,7-naphthylidene.

The structures of specific examples of linkers which are useful in the present invention are as follows:

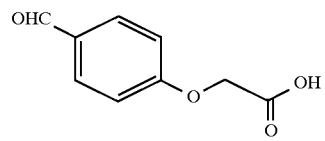

1

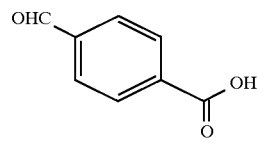

2

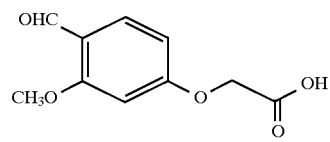

3

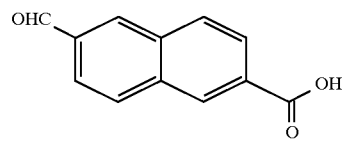

4

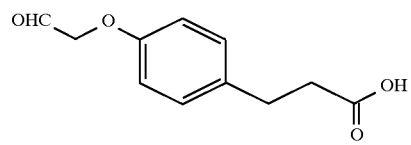

5

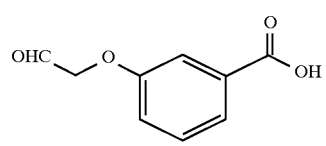

6

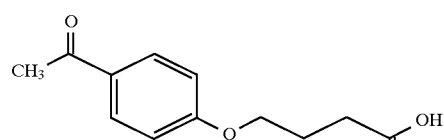

7

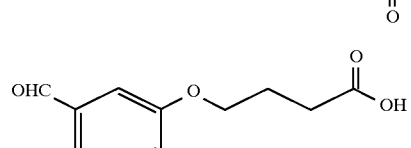

8

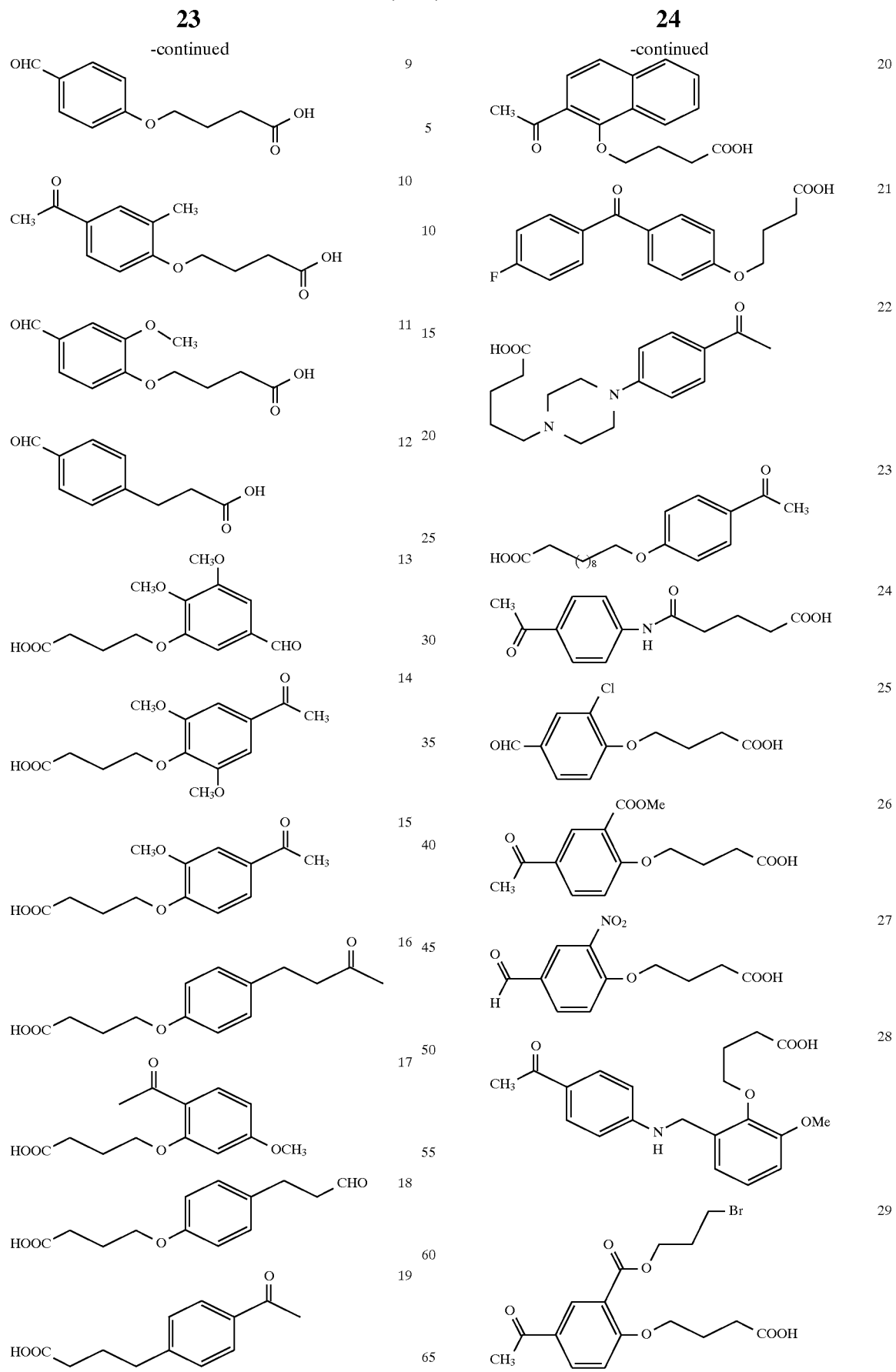

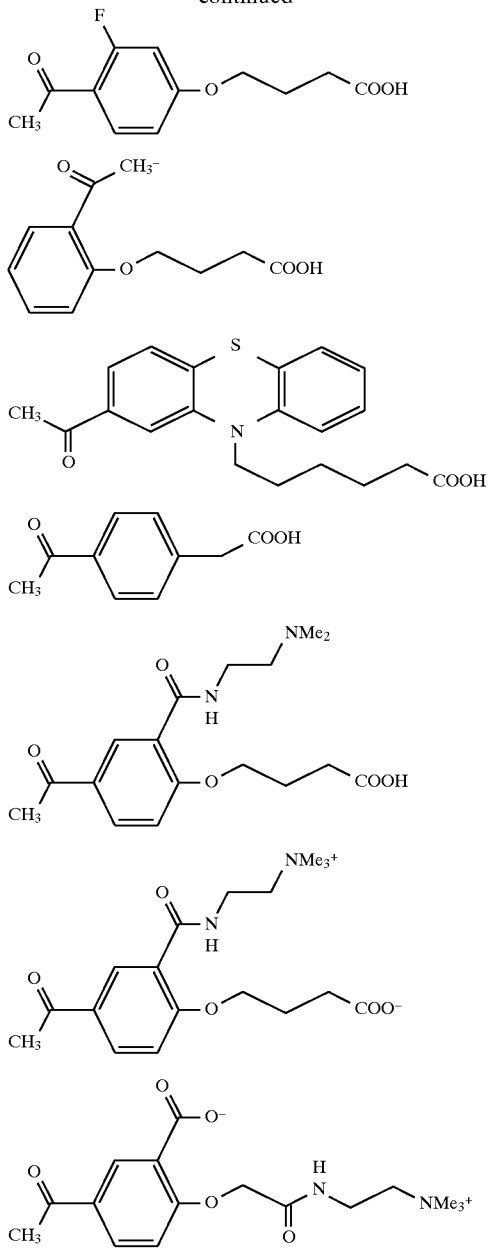

Only a few of the more simple of these linkers are commercially available, i.e., linkers 1, 2, 3, 19, 23, 24, and 33. Linker 20 is listed by the Chemical Abstract Services with registry number 5084-45-7. Many linkers which contain aryl ethers as a part of their structure, such as 7, 8, 10, 13, 14, 15, 16, 17, 20, 21, 25, 28, 30, and 31, can be made by alkylating a phenolic ketone with an electrophile, such as ethyl 4-bromobutyrate, using an appropriate base, such as potassium carbonate, in an appropriate solvent, such as N,N-dimethyl formamide, and then converting the ester into the required carboxylic acid by hydrolysis with, for example, sodium hydroxide or potassium carbonate in aqueous methanol. This strategy can also be used with linkers such as 5, 6, 9, 11, 18, or 27, where the carbonyl is carried through the initial steps of the preparation in a masked form, such as an olefin or an alcohol. The carbonyl can then be generated later, as described in the examples, by oxidation with ozone or pyridinium chlorochromate, resp. This procedure is especially valuable when a more reactive carbonyl is present in the final linker.

When necessary, the required carboxylic acid can be introduced in a masked form as in the preparation of linker 26. In this case the phenol is alkylated with 5-bromo-1-pentene and the acid is liberated from the olefin by reaction with ozone followed by pyridinium chlorochromate oxidation. Linkers such as 22 or 32 can be made by alkylating an appropriate secondary amine (a piperazine or phenothiazine derivative, resp.) with an appropriate electrophile and then exposing the required carboxylic acid in a later step, similar to the previously mentioned strategies. Linker 12 was made by reduction of the corresponding cinnamate with hydrogen. Although this reaction gave a relatively impure product, the crude mixture was useful for conversion to the required hydrazone because none of the by-products contained aldehyde groups. Structures with more elaborate substituents, such as linkers 33, 34, 35, or 36, can be made from simpler structures by, for example, reacting an ester with an appropriate nucleophile or by quaternizing an amine with an electrophile, such as methyl iodide.

The linkers defined above can be used to form conjugates as follows:

Scheme 1

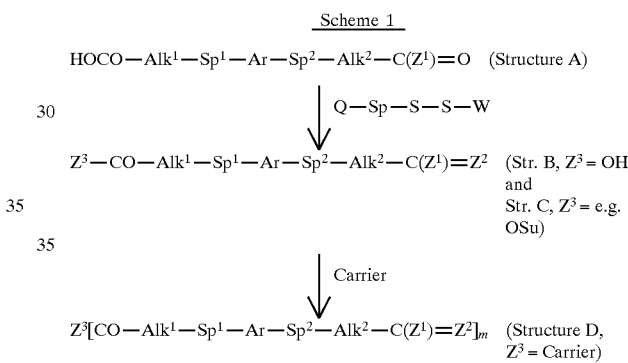

With reference to Scheme 1 above, the linker of structure A, wherein $Z^1$, $Alk^1$, $Sp^1$, $Ar$, $Sp^2$, and $Alk^2$ are as hereinbefore defined, is condensed with a compound of structure W-S-S-Sp-Q, which itself is derived from a methyltrithio antitumor antibiotic, and wherein W is

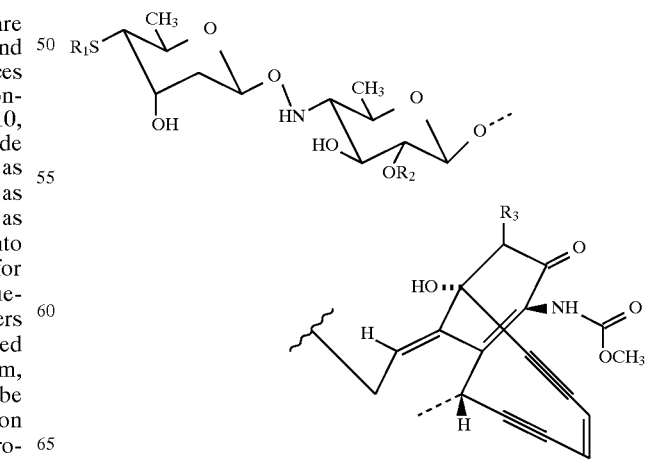

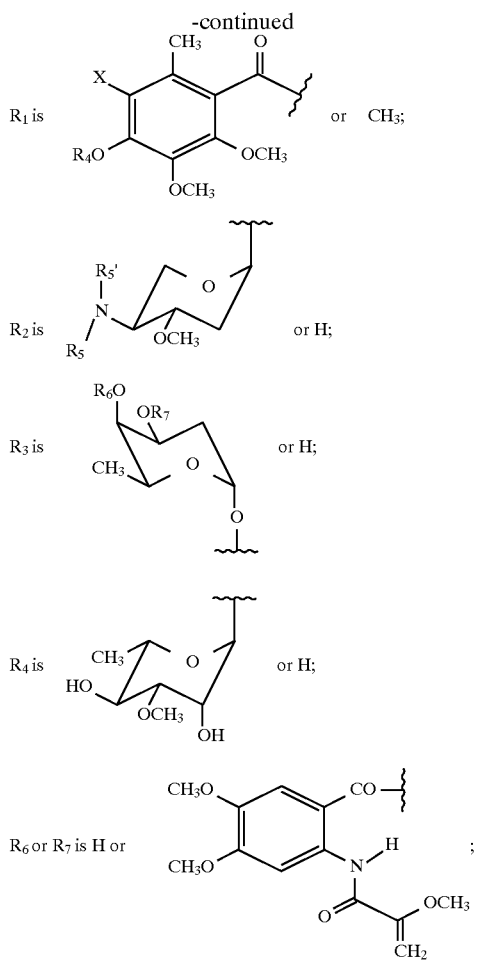

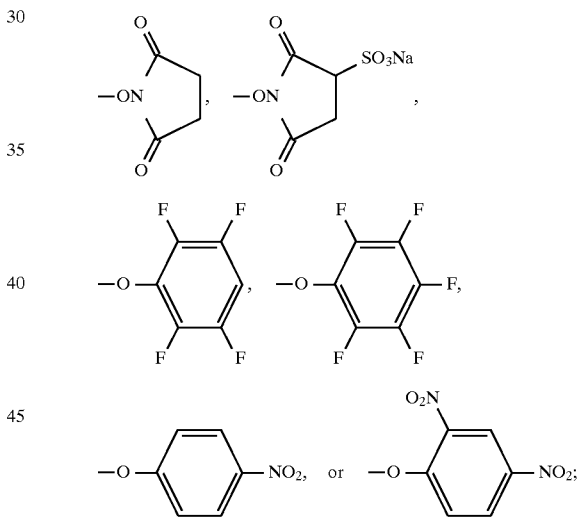

$R_5$ is —$CH_3$, —$C_2H_5$, or —$CH(CH_3)_2$; X is an iodine or bromine atom; $R_5'$ is a hydrogen or the group RCO, wherein R is hydrogen, branched or unbranched ($C_1$–$C_{10}$) alkyl or ($C_1$–$C_{10}$) alkylene group, a ($C_6$–$C_{11}$) aryl group, a ($C_6$–$C_{11}$) aryl-alkyl ($C_1$–$C_5$) group, or a heteroaryl or heteroaryl-alkyl ($C_1$–$C_5$) group wherein heteroaryl is defined as 2- or 3-furyl, 2- or 3-thienyl, 2- or 3-(N-methylpyrrolyl), 2-, 3-, or 4-pyridinyl, 2-, 4-, or 5-(N-methylimidazolyl), 2-, 4-, or 5-oxazolyl, 2-, 3-, 5-, or 6-pyrimidinyl, 2-, 3-, 4-, 5-, 6-, 7-, or 8-quinolyl, or 1-, 3-, 4-, 5-, 6-, 7-, or 8-isoquinolyl, all aryl and heteroaryl optionally substituted by one or more hydroxy, amino, carboxy, halo, nitro, lower ($C_1$–$C_3$) alkoxy, or lower ($C_1$–$C_5$) thioalkoxy groups; Sp is a straight or branched-chain divalent or trivalent ($C_1$–$C_{18}$) radical, divalent or trivalent aryl or heteroaryl radical, divalent or trivalent ($C_3$–$C_{18}$) cycloalkyl or heterocycloalkyl radical, divalent or trivalent aryl- or heteroaryl-alkyl ($C_1$–$C_{18}$) radical, divalent or trivalent cycloalkyl- or heterocycloalkyl-alkyl ($C_1$–$C_{18}$) radical or divalent or trivalent (C2–$C_{18}$) unsaturated alkyl radical, wherein heteroaryl is furyl, thienyl, N-methylpyrrolyl, pyridinyl, N-methylimidazolyl, oxazolyl, pyrimidinyl, quinolyl, isoquinolyl, N-methylcarbazoyl, aminocoumarinyl, or phenazinyl and wherein if Sp is a trivalent radical, it can be additionally substituted by lower ($C_1$–$C_5$) dialkylamino, lower ($C_1$–$C_5$) alkoxy, hydroxy, or lower ($C_1$–$C_5$) alkylthio groups; and Q is $H_2$NHNCO—, $H_2$NHNCS—, $H_2$NHNCONH—, $H_2$NHNCSNH—, or $H_2$NO—, to produce a compound of structure B, wherein $Z^1$, $Alk^1$, $Sp^1$, Ar, $Sp^2$, and $Alk^2$ are as hereinbefore defined, $Z^2$ is Q-Sp-S-S-W, wherein Sp and W are as herein above defined, Q is =NHNCO—, =NHNCS—, =NHNCONH—, =NHNCSNH—, or =NO—, and $Z^3$ is —OH.

The condensation can be run in most compatible organic solvents, but is particularly efficient in alcoholic solvents such as methanol or ethanol. This condensation reaction is acid catalyzed. The carboxylic acid in the linkers themselves is sufficient in many cases to catalyze this reaction, but adding a compatible acid catalyst, such as about 5% acetic acid, helps improve the rate of reaction in many cases. The temperature of this reaction can be from about ambient temperature to the reflux temperature of the solvent. The products are isolated in pure form by removing the volatile solvents and purifying the mixture by chromatography on a suitable medium such as BIOSIL A™, a modified silica gel available from Bio-Rad. It should be understood that the products of structure B, as well as the products from the further transformation of these compounds, exist as easily-interconverted syn and anti isomers at the locus defined as Q, and that these products can exist in different hydrated forms, depending on the exact conditions of solvent and the pH at which these compounds are examined. Such differing physical forms are also included within the scope of this patent.

The carboxylic acid of structure B ($Z^3$=—OH) is next converted to an activated ester in preparation for conjugation of these intermediates with carrier molecules. Such transformations convert $Z^3$ (structure B) to halogen, —$N_3$, For example, reaction of the carboxyl form of structure B ($Z^3$=—OH) with a coupling agent, such as 1,3-dicyclohexylcarbodiimide or 1-(3-dimethylaminopropyl)-3-ethylcarbodiimide hydrochloride, and N-hydroxysuccinimide or other comparable carboxyl-activating group in an inert solvent, such as N,N-dimethylformamide, tetrahydrofuran, or acetonitrile, leads to the formation of an activated ester, such as the N-hydroxysuccinimide ester described herein. These active esters can be isolated in pure form by removal of the volatile solvents and chromatography on an appropriate medium, such as BIOSIL A™. Alternately, the coupling reaction can be quenched with a polymeric carboxylic acid, filtered, and stripped of organic solvents, and the crude product can be used in the following step without further purification. This is especially useful if the active ester is difficult to handle, such as when

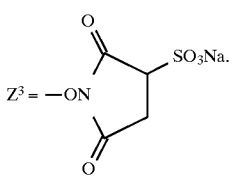

The final step in the construction of the conjugates of this patent involves the reaction of an activated ester (structure C) with a targeting molecule, as shown in Scheme 1. This produces a compound of structure D, wherein $Z^1$, $Z^2$, $Alk^1$, $Sp^1$, Ar, $Sp^2$, and $Alk^2$ are as hereinbefore defined, m is 0.1 to 15, and $Z^3$ is a protein such as a growth factor or a mono- or polyclonal antibody, their antigen-recognizing fragments, or their chemically or genetically manipulated counterparts or a steroid, wherein a covalent bond to a protein is an amide formed from reaction with lysine side chains and the covalent bond to a steroid is an amide or an ester.

This conjugation reaction can be carried out in various appropriate buffers, such as borate, phosphate, or HEPES at slightly basic pH (pH~7.4 to 8.5). The final construct can then be purified by appropriate methods, such as gel-exclusion chromatography, to remove unattached drug and aggregates to yield monomeric conjugates. This sequence of steps constitutes Method A as described in greater detail in the Examples section of this patent.

Alternative methods for constructing the conjugates of Scheme 1 are also contemplated as shown in Scheme 2.

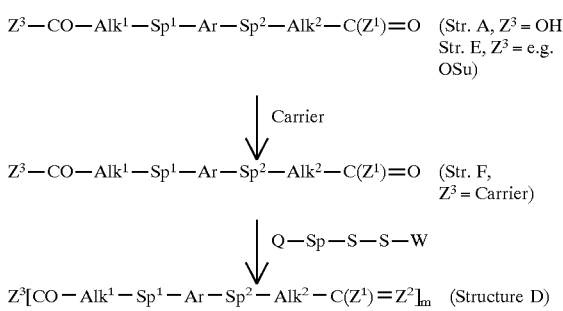

For example, the linker (structure A as defined above) can be converted to an active ester and reacted with the targeting molecule prior to the reaction with the drug. Such manipulations convert structure A into structure E, wherein $Z^1$, $Alk^1$, $Sp^1$, Ar, $Sp^2$, and $Alk^2$ are as hereinbefore defined, $Z^2$ is an oxygen atom, and $Z^3$ is halogen, —$N_3$,

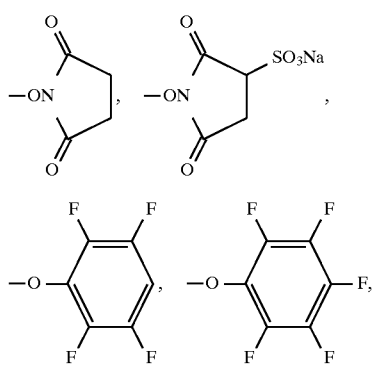

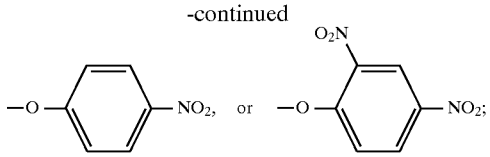

The activated ester is then reacted with the carrier to produce structure F, wherein $Z^1$, $Alk^1$, $Sp^1$, Ar, $Sp^2$, and $Alk^2$ are as hereinbefore defined, $Z^2$ is an oxygen atom, m is about 1 to about 20, and $Z^3$ is a protein selected from mono- and polyclonal antibodies, their antigen-recognizing fragments, and their chemically or genetically manipulated counterparts and growth factors and their chemically or genetically manipulated counterparts, wherein a covalent bond to the protein is an amide formed from reaction with lysine side chains, or a steroid, wherein the covalent bond to the steroid is an amide or an ester.

Once the targeting molecule has been modified with the linker, it can be reacted with a compound of structure Q-Sp-S-S-W, which itself is derived from a methyltrithio antitumor antibiotic, and wherein W and Sp are as hereinbefore defined, and Q is $H_2NHNCO$—, $H_2NHNCS$—, $H_2NHNCONH$—, $H_2NHNCSNH$—, or $H_2NO$— to produce a compound of Structure D (vida supra).

Figure 24:
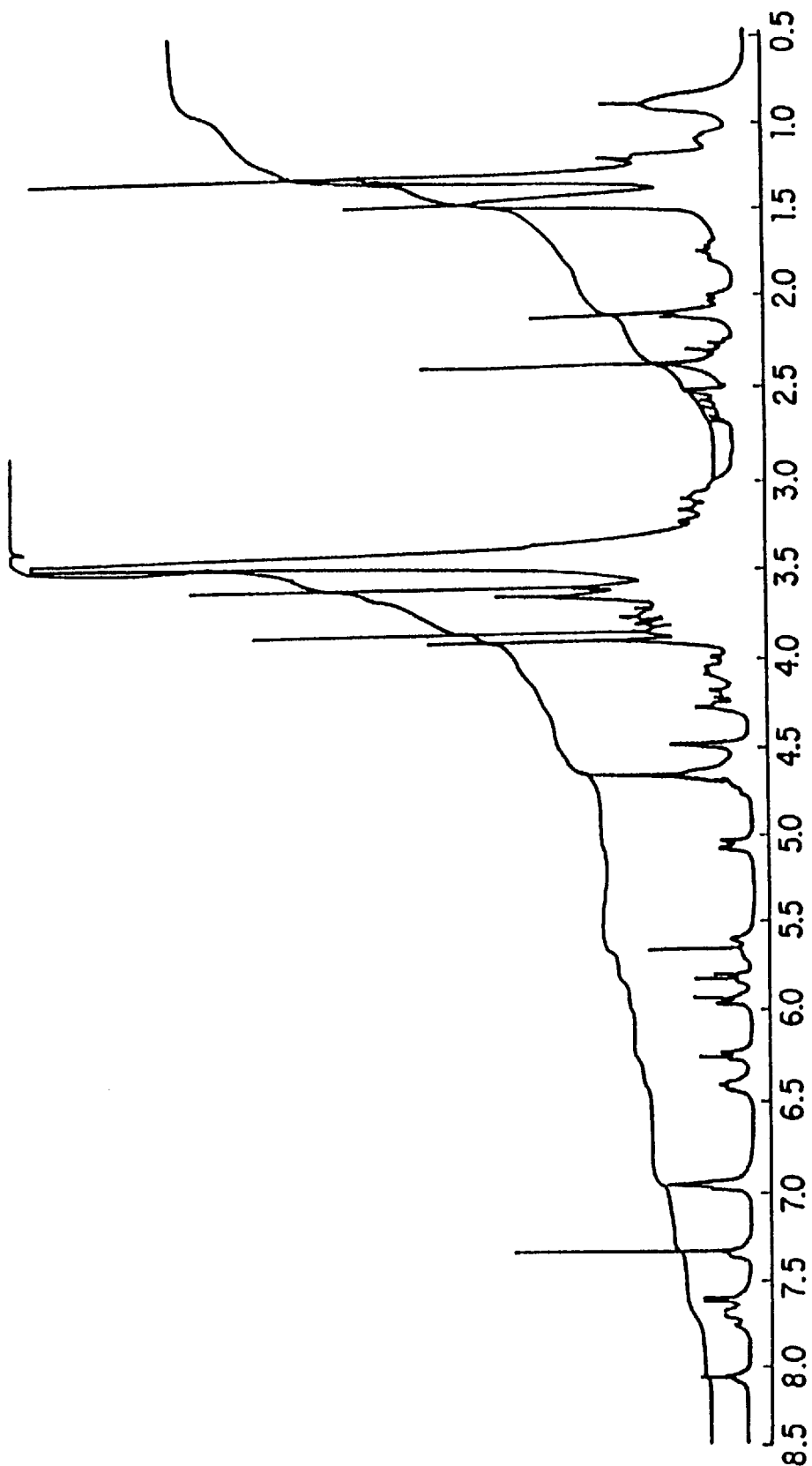
FIG. 24: The proton magnetic resonance spectrum of 4-formylphenoxyacetic acid condensed with Calicheamicin N-acetyl gamma dimethyl hydrazide.
Figure 25:
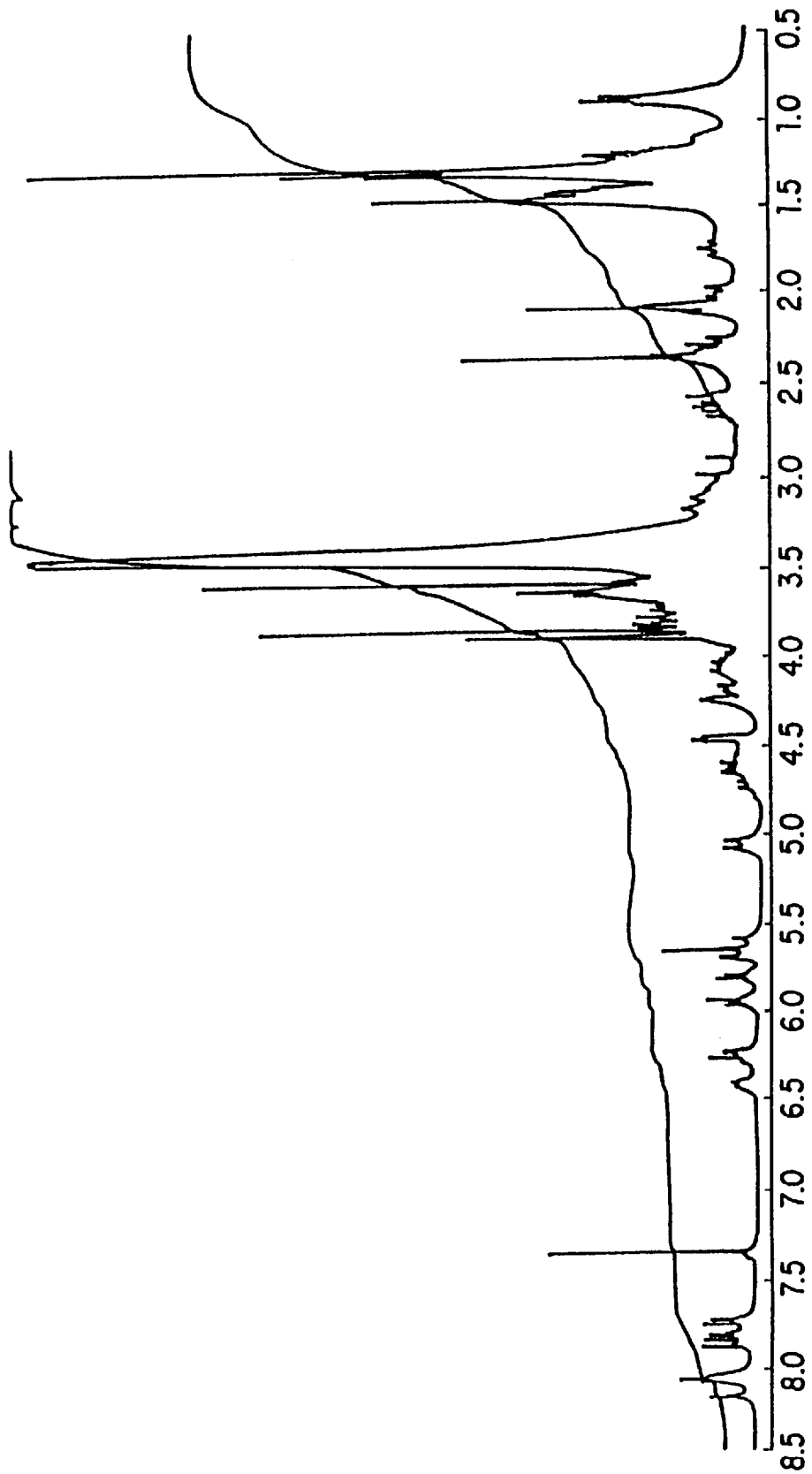
FIG. 25: The proton magnetic resonance spectrum of 4-formylbenzoic acid condensed with Calicheamicin N-acetyl gamma dimethyl hydrazide.

This sequence of steps in Scheme 2 constitutes Method B in the Examples section of this patent. Similar antibody-carbonyl constructs are covered in U.S. Pat. No. 5,144,012 mentioned above. Most of the linkers exemplified herein are new and offer the advantage that a much broader range of structural types and hence a broader range of stabilities is demonstrated. As a specific example, the acetophenone linkers, which are new to this patent, produced conjugates with better hydrolytic release properties of drug and which are more potent when used with the examples of the antibodies shown here. Specifically, the two conjugates prepared from h-P67.6 using 4-formylbenzenepropanoic acid or 4-acetylbenzenebutanoic acid condensed with calicheamicin N-acetyl gamma hydrazide (the two conjugates only differ by having $Z^1$=—H and $Z^1$=—$CH_3$, respectively, in structure 3 of FIG. 24) gave in vitro $IC_{50}$'s of 1.0 and 0.012 ng/mL, and specificity indices of 950 and 26,000, respectively. Although the acetophenone based linkers are seen to be superior in this case, it is not necessarily easy to predict which linker will be superior for any given targeting agent-drug construct.

BIOLOGICAL CHARACTERIZATION

Assessment of the biological properties of the conjugates included measuring their ability to recognize the antigen on target cell lines, relative to the unmodified antibody, and determining their selectivity and cytotoxic potentials, using the following methods:

IMMUNOAFFINITY ASSAYS

Relative immunoaffinities of conjugates are determined in a competitive binding assay in which varying concentrations of test conjugate are allowed to compete with a fixed amount of the same antibody labeled with $^{125}$I-Bolton Hunter reagent for binding to a fixed number of cells. For m- or h-P67.6, HEL 92.1.7 human erythroleukemia cells [ATCC (American Type Culture Collection) TIB 180] are used at a concentration of $10^7$ cells/mL; for CT-M-01, cell line A2780DDP (E. M. Newman, et al., "Biochem. Pharmacol." 37, 443 (1988)) is used; and for m- or h-A33, cell line COLO 205 (ATCC CCL 222) is used. The concentration of test conjugate required to obtain 50% inhibition of binding of the labeled antibody to target cells is compared with the concentration of a reference preparation of native antibody required for 50% inhibition.

Samples for assay are adjusted to ~300 μg protein/mL in medium and six serial four-fold dilutions of each are prepared in medium (RPMI-1640 containing 5% heat-inactivated fetal calf serum), for a total of seven concentrations of each sample. The reference antibody is diluted in the same way. An aliquot of 0.05 mL of each dilution is transferred to a 12×75 mm plastic tube, and 0.05 mL of labeled reference antibody at 4 μg/mL is added. The tubes are mixed and chilled at 4° C. Then 0.1 mL of chilled cell suspension is added to each tube. All tubes are mixed again, and incubated for 1 hr at 40° C.

Controls to determine maximal binding and non-specific binding are included in each assay. Maximal binding is determined by mixing 0.05 mL of medium, 0.05 mL of $^{125}$I-antibody, and 0.1 mL of cells; non-specific binding is determined by mixing 0.05 mL of 500 μg/mL of native antibody, 0.05 mL of iodinated antibody, and 0.1 mL of cells.

At the end of the incubation, cells are washed twice, by centrifugation and resuspension, with 3 mL of cold PBS each time. The cells are resuspended in 0.5 mL of PBS, transferred to clean tubes, and radioactivity is determined in a gamma-counter.

The percent inhibition of binding is calculated by the following equation:

$$\% I = \{[(cpm_{max\,binding} - cpm_{non-specific}) - (cpm_{sample} - cpm_{non-specific})] \div (cpm_{max\,binding} - cpm_{non-specific})\} \times 100$$

The percent inhibition values are plotted against sample concentrations, and from the resulting curves the sample concentration that gives 50% inhibition of binding ($IC_{50}$) is interpolated. The relative immunoaffinity of each tested conjugate is then determined as follows:

Relative Immunoaffinity=$IC_{50}$(reference)÷$IC_{50}$(sample)

IN VITRO CYTOTOXICITY ASSAY

Cytotoxic activities are determined in an in vitro pulse assay in which varying concentrations of test conjugate are incubated with antigen-positive and antigen-negative cells for 1 hr, then cultured for three days. Viability is assessed by [$^3$H]thymidine incorporation during the final 24 hr of culture. As a measure of potency, the concentration of test conjugate required to inhibit [$^3$H]thymidine incorporation by 50% ($IC_{50}$) is determined from the titration curve. The specificity is determined by comparing $IC_{50}$ values on antigen-positive and antigen-negative cells for P67.6, A33, and m-CT-M-01 or by use of a conjugate of the same drug with the non-targeting antibody P67.6 for h-CT-M-01 conjugates or MOPC-21 for anti-Tac conjugates. MOPC-21 (F. Melchers, "Biochem. J." 119, 765 (1970)) is an antibody which does not recognize any normally occurring, physiologically pertinent antigen.

For P67.6, antigen-positive HL-60 human promyelocytic leukemia cells (ATCC CCL 240) and antigen-negative Raji human Burkitt lymphoma cells (ATCC CCL 86) are used; for A33, antigen-positive COLO 205 cells and antigen-negative Raji cells are used; and for h-CT-M-01, ZR-75-1 cells (ATCC CRL1500) are used. For m-CT-M-01 antigen-positive A2780DDP cells and antigen-negative Raji cells are used, and for h-CT-M-01, ZR-75-1cells (ATCC CRL1500) are used. Cells are collected by centrifugation, counted, and resuspended in fresh medium (RPMI-1640+5% heat-inactivated fetal calf serum+antibiotics) at a cell concentration of ~$10^6$/mL.

Samples for assay are readjusted to ~1 μg/mL of drug equivalents in medium and five serial ten-fold dilutions of each are prepared in medium, for a total of six concentrations of each sample. In addition, a medium control is included with each sample set, as well as calicheamicin N-acetyl gamma as a drug control. An aliquot of 0.1 mL of cell suspension is added to 17×100 mm plastic tubes containing 0.1 mL of sample; a separate series of tubes is prepared for each cell line. The tubes are loosely capped and incubated for 1 hr at 37° C. in a humidified atmosphere of 5% $CO_2$ in air. At the end of the incubation, cells are washed twice by centrifugation and resuspended with 8 mL of medium each time. Cell pellets are resuspended in 1 mL of medium and plated in triplicate in 96-well microtiter plates at 0.2 mL/well. The plates are incubated for 2 days at 37° C. as above. Then 0.1 mL of medium is removed from each well and replaced with 0.1 mL of fresh medium containing 0.1 μCi of [$^3$H]thymidine. Plates are returned to the incubator for one more day. Plates are frozen and thawed, and cells are harvested on glass fiber filter mats. The amount of [$^3$H]thymidine incorporated is determined by liquid scintillation counting.

The measured cpm of the triplicate cultures of each sample dilution are averaged and the percent inhibition of [$^3$H]thymidine incorporation is calculated by the following equation, where the values for no inhibition and maximal inhibition come from the medium controls, and the highest concentration of calicheamicin N-acetyl gamma, respectively:

$$\% I = \{[(cpm_{no\,inhibition} - cpm_{max\,inhibition}) - (cpm_{sample} - cpm_{max\,inhibition})] \div (cpm_{no\,inhibition} - cpm_{max\,inhibition})\} \times 100$$

The percent inhibition values are plotted against sample concentrations, and from the resulting curves the sample concentration that gives 50% inhibition of [$^3$H]thymidine incorporation ($IC_{50}$) is interpolated. For P67.6, A33, and m-CT-M-01 conjugates, the specificity of a particular conjugate for antigen-positive cells is calculated by taking the ratio of the $IC_{50}$ against non-target cells to the $IC_{50}$ against target cells. The same ratio is calculated for the free drug. Then, to correct for inherent differences in the sensitivities of the two cell lines to the drug, the Specificity Index for each sample is calculated as follows:

Specificity Index = $[IC_{50\,(sample\,on\,antigen\,neg)} \div IC_{50\,(sample\,on\,antigen\,pos)}] \div [IC_{50\,(drug\,on\,antigen\,neg)} \div IC_{50\,(drug\,on\,antigen\,pos)}]$ For conjugates of Anti-Tac or h-CT-M-01, the Specificity Index is calculated as the ratio of $IC_{50}$'S for the non-targeting conjugate and the targeting conjugate as follows:

Specificity Index=$IC_{50}$ (non-targeting conjugate)÷$IC_{50}$ (targeting conjugate)

IN VIVO ANTITUMOR ASSAY

Human tumors (either ~$10^7$–$10^8$ cells or 5 to 8 fragments of solid tumors 2 mm$^3$ in size) are implanted subcutaneously into athymic mice (nude mice) and test samples are inoculated intraperitoneally (ip) at several dose levels on a q 4 day×3 schedule, starting 2–3 days after tumor implantation with 5 mice per test group and 10 in the saline control group. Tumor mass is estimated by measuring the tumor length and width once weekly up to 42 days post tumor implantation with a Fowler ultra CAL II electronic caliper and using the formula: mg tumor={Length(mm)×Width(mm)}/2. Tumor growth inhibition is calculated as the ratio of the mean tumor mass of treated animals compared with untreated controls and is expressed as "% T/C". (0% T/C implies no detectable tumor. All control animals routinely develop easily measurable tumor.)

EX VIVO INHIBITION OF COLONY FORMATION

For P67.6 conjugates, human leukemic bone marrow cells which are CD-33 positive are plated in the presence of 2 ng/mL drug equivalents. The number of colonies which form are counted and reported as the percent versus a control which consists of a h-CT-M-O1 conjugate which does not recognize the CD-33 antigen. All the data reported were generated with bone marrow from one patient whose leukemic cells had good antigen expression and good response to this general type of treatment.

For anti-Tac, peripheral blood from CML patients was tested. Progenitor cells for cells of the various hematopoietic lineages can be detected by culturing bone marrow cells and blood cells in a semisolid matrix such as methylcellulose and observing the formation of colonies containing mature differentiated cells. There are progenitor cells that proliferate to form colonies of granulocytes or macrophages, or both, called colony-forming units for granulocytes-macrophages (CFU-GM). Some CFU-GM form colonies within seven days (D7 CFU-GM); some require fourteen days for colony formation (D14 CFU-GM) [N. Jacobsen, et al., "Blood" 52: 221, (1978), and Ferrero D et al."Proc. Natl. Acad. Sci. USA" 80: 4114, (1983)]. Inhibition of the growth of D14 CFU-GM on blood cells treated with anti-Tac was compared to those treated with non-targeting MOPC 21 conjugates. The number of D14 CFU-GM colonies are plotted against sample concentrations, and from the resulting curves the sample concentration that gives 50% inhibition of D14 CFU-GM colony growth is interpolated. Specificity was measured by the ratio of the $IC_{50}$ of the non-targeting conjugate versus the $IC_{50}$ of the targeting conjugate. Normal blood does not produce CFU-GM colonies and normal bone marrow D14 CFU-GM colonies are not inhibited by anti-Tac conjugates.

The invention is further described with the following non-limiting preparations and examples. (Preparations describe the syntheses of compounds useful in this invention but for which there is known prior art. Examples describe the syntheses of compounds which are useful and new to this invention.)

SYNTHESIS OF STRUCTURES A (Scheme 1 and Scheme 2)

EXAMPLE 1, COMPOUND 5

4-(2-Oxoethoxy)benzenepropanoic acid

4-Hydroxybenzenepropanoic acid (500 mg, 3.01 mmol) is allowed to react with 910 mg (7.52 mmol) of allyl bromide by the same procedure described in Example 2 to give 610 mg (82%) of 2-propenyl-4-(2-propenyloxy)-benzenepropanoic ester as a colorless oil. The product is utilized in the next reaction without further purification. The $^1$H NMR (300 MHz, CDCl$_3$) is consistent with the desired product; IR (neat) 3450, 1740, 1650, 1610, 1510 cm$^{-1}$; MS (CI low res) m/e 247 (M+H), 229, 215, 187, 175; Analysis calculated for $C_{15}H_{18}O_3$: C, 73.15; H, 7.37; found: C, 73.09; H, 6.74.

2-Propenyl-4-(2-propenyloxy)benzenepropanoic ester (271 mg, 1.1 mmol) is treated with 0.14 mL (1.38 mmol) of 10M sodium hydroxide solution according to the same procedure described for Example 2 to give 196 mg (86%) of 4-(2-propenyloxy)benzenepropanoic acid as a white powder. The product is utilized in the next reaction without further purification: m.p. 88°–89°; the $^1$H NMR (300 MHz, CDCl$_3$) is consistent with the desired product; IR (KBr) 3200, 1720, 1700, 1610 cm$^{-1}$; MS (CI low res) m/e 207 (M+H), 189, 175, 147; Analysis calculated for $C_{12}H_{14}O_3$: C, 69.89; H, 6.84; found: C, 69.87; H, 6.68.

4-(2-Propenyloxy)benzenepropanoic acid (120 mg, 0.58 mmol) is treated with ozone by the procedure described in Example 2 to give 100 mg (82%) of 4-(2-oxoethoxy) benzenepropanoic acid as a white powder: m.p. 95°–100°; the $^1$H NMR (300 MHz, CDCl$_3$) is consistent with the desired product; IR (KBr) 3400, 1740, 1720, 1610 cm$^{-1}$; MS (CI low res) m/e 207, 191, 179, 165, 149.

EXAMPLE 2, COMPOUND 6

3-(2-Oxoethoxy)benzoic acid

A mixture of 1.0 g (7.24 mmol) of 3-hydroxybenzoic acid, 3.0 g (25.3 mmol) of allyl bromide, and 5 g (36.2 mmol) of potassium carbonate in 4 mL of N,N-dimethylformamide is stirred at room temperature for 12 hours. The mixture is diluted with 20 mL of ether and washed five times with 20 mL of water. The organic layer is then washed successively with 20 mL of saturated sodium bicarbonate solution and 20 mL of saturated sodium chloride solution. The organic layer is separated and dried over magnesium sulfate. The mixture is filtered and the organic solution is concentrated in vacuo to give 1.4 g (88%) of 3-(2-propenyloxy)benzoic acid, 2-propenyl ester as a clear colorless oil. The product is utilized in the next reaction without further purification. The $^1$H NMR (300 MHz, CDCl$_3$) is consistent with the desired product; IR (KBr) 1720, 1650, 1600 cm$^{-1}$; MS (CI low res) m/e 219 (M+H), 203, 175, 161; Analysis calculated for $C_{13}H_{14}O_3$: C, 71.54; H, 6.47; found: C, 70.31; H, 5.97.

A solution of 917 mg (4.2 mmol) of 3-(2-propenyloxy) benzoic acid, 2-propenyl ester in 9 mL of methanol/water (3:2) at room temperature is treated with 0.53 mL (5.25 mmol) of 10M sodium hydroxide solution. The solution is allowed to stir for one hours then acidified with 5 mL of 10% sodium bisulfate solution and extracted with 25 mL of ethyl acetate. The organic layer is washed with saturated sodium chloride solution, dried over magnesium sulfate, and concentrated in vacuo to give 732 mg (97%) of 3-(2-propenyloxy)benzoic acid as a white powder. The product is utilized in the next reaction without further purification; m.p. 78°–79°; the $^1$H NMR (300 MHz, CDCl$_3$) is consistent with the desired product; IR (KBr) 3000, 1690, 1620, 1590 cm$^{-1}$; MS (CI low res) m/e 179 (M+H), 161, 135; Analysis calculated for $C_{10}H_{10}O_3$: C, 67.41; H, 5.66; found: C, 67.37; H, 5.59.

A solution of 300 mg (1.68 mmol) of 3-(2-propenyloxy) benzoic acid in 5 mL of methylene chloride is cooled to −78° C. Ozone is introduced by bubbling the gas into the solution through a glass tube until a blue color persists. The solution is then purged with a stream of argon and 1 mL of methyl sulfide is added. The solution is diluted with 20 mL of ether and washed with water. The organic layer is separated and allowed to stand over magnesium sulfate then concentrated in vacuo to give 283 mg (93%) of 3-(2-oxoethoxy)benzoic acid as a colorless oil. The product is utilized in the next reaction without further purification: m.p. 120°–130°; the $^1$H NMR (300 MHz, CDCl$_3$) is consistent with the desired product; IR (KBr) 3400, 3000, 1680, 1590 cm$^{-1}$; MS (CI low res) m/e 181 (M+H), 163, 139, 119.

PREPARATION 3, COMPOUND 7

4-(4-Acetylphenoxy)butanoic acid

A solution of 0.90 g (6.61 mmol) of 4'-hydroxyacetophenone, and 1.93 g (9.92 mmol) of ethyl 4-bromobutyrate in 1.80 mL of N,N-dimethylformamide is stirred for 48 hours, under dry conditions with 2.74 g (19.8 mmol) of potassium carbonate and 0.110 g (0.66 mmol) of potassium iodide. The reaction mixture is then evaporated under vacuum, and the residue partitioned between ether and water. The organic phase is separated, washed thrice with water, dried with magnesium sulfate, filtered, and evaporated under vacuum to give a brown solid. This is recrystallized from a warm ether-hexane mixture. The beige crystals are air dried, leaving 0.84 g (51%) of 4-(4-acetylphenoxy)-butanoic acid, ethyl ester: m.p. 59°–61° C.; IR (KBr) 1740, 1670 cm$^{-1}$; $^1$H-NMR (CDCl$_3$) is consistent with the desired product; MS (FAB) m/e 251.1285 Δ=–0.2 mm$\mu$ (M$^+$+H). Analysis calculated for C$_{14}$H$_{18}$O$_4$: C, 67.18; H, 7.25; O, 25.57. Found: C, 67.16; H, 7.16; O, 25.68.

A sample of 0.25 g (1.00 mmol) of 4-(4-acetylphenoxy) butanoic acid, ethyl ester (example 1) is dissolved in 15 mL of methanol/water (3:2), with stirring. Then, 0.21 g (1.50 mmol) of potassium carbonate is added and the reaction is stirred for 18 hours under an argon atmosphere. Next, the reaction mixture is evaporated under vacuum and the residue dissolved in 20 mL of a 0.1N solution of sodium hydroxide. This basic solution is washed with ether, the aqueous phase acidified by addition of sodium bisulfate, and the resulting mixture extracted with ethyl acetate. This solution is then dried with magnesium sulfate, filtered and evaporated, leaving an off-white solid. This is crystallized from ethyl acetate with the addition of an equal volume of ether. This provides 0.18 g (80%) of 4-(4-acetylphenoxy)butanoic acid as light beige crystals: m.p. 148°–50° C.; IR (KBr) 1730, 1650 cm$^{-1}$; $^1$H-NMR (CDCl$_3$) is consistent with the desired product; MS (FAB) m/e 223.0974 Δ=–0.4 mm$\mu$(M$^+$+H). Analysis calculated for C$_{12}$H$_{14}$O$_4$: C, 64.85; H, 6.35; O, 28.80. Found: C, 64.61; H, 6.36; O, 29.03.

PREPARATION 4, COMPOUND 8

4-(3-Formylphenoxy)butanoic acid

3-Hydroxybenzaldehyde (900 mg, 7.37 mmol) is treated with 2.16 g (11.05 mmol) of ethyl 4-bromobutyrate, 3.06 g (22.11 mmol) of potassium carbonate, and a catalytic amount (110 mg 0.74 mmol) of sodium iodide under the same conditions as in Preparation 3 to give a yellow oil. Purification by flash chromatography using hexane/ethyl acetate (10:1) gives 1.61 g of 4-(3-formylphenoxy)butanoic acid, ethyl ester as a light yellow oil. The $^1$H NMR (300 MHz, CDCl$_3$) is consistent with the desired product; IR (neat) 1730, 1700, 1600, 1580 cm$^{-1}$; MS (CI low res) m/e 237 (M+H), 191, 115.

A solution of 385 mg (1.63 mmol) of 4-(3-formylphenoxy)butanoic acid, ethyl ester and 850 mg (6.15 mmol) of potassium carbonate is stirred in 6 mL of methanol/water (3:2) at room temperature for 8 hours. The solution is then concentrated in vacuo. The residue is dissolved in 10 mL of 0.1N sodium hydroxide solution and washed with 20 mL of ether. The aqueous layer is separated and acidified with sodium bisulfate and extracted with ethyl acetate. The organic layer is washed with saturated sodium chloride solution, then dried over magnesium sulfate. The mixture is then filtered and concentrated in vacuo to give 315 mg of 4-(3-formylphenoxy)butanoic acid as a white solid. The product is utilized in the next reaction without further purification. m.p. 62°–63°; the $^1$H NMR (300 MHz, CDCl$_3$) is consistent with the desired product; IR (KBr) 3400, 3000, 1700, 1690, 1590 cm$^{-1}$; MS (CI low res) m/e 209 (M+H), 191, 123.

PREPARATION 5, COMPOUND 9

4-(4-Formylphenoxy)butanoic acid

4-Hydroxybenzyl alcohol (1 g, 8.06 mmol) is treated with 1.73 g (8.86 mmol) of ethyl 4-bromobutyrate, 3.34 g (24.2 mmol) of potassium carbonate and a catalytic amount (120 mg 0.81 mmol) of sodium iodide under the same conditions as described in Preparation 3 to give 1.73 g of 4-[4-(hydroxymethyl)phenoxy]butanoic acid, ethyl ester as a light brown oil (90%). The product is utilized in the next reaction without further purification. The $^1$H NMR (300 MHz, CDCl$_3$) is consistent with the desired product; IR (neat) 3400, 1730, 1610, 1580, 1510 cm$^{-1}$; MS (CI) m/e 238, 221, 115.

A mixture of 230 mg (0.97 mmol) of 4-[4-(hydroxymethyl)phenoxy]butanoic acid, ethyl ester, 624.2 mg (2.9 mmol) of pyridinium chlorochromate, and a catalytic amount of 4 Å molecular sieve is stirred in 2 mL of methylene chloride at room temperature for 3 hours. The mixture is diluted with 20 mL of ether, filtered and concentrated in vacuo to give 175 mg (76%) of a light yellow oil. The oil (150 mg, 0.63 mmol) is dissolved in 2.3 mL of methanol/water (3:2) and treated with 307 mg (2.22 mmol) of potassium carbonate according to the procedure described for Example 4 to give 100 mg (75%) of 4-(4-formylphenoxy)butanoic acid as a white powder. The product is used without further purification. The $^1$H NMR (300 MHz, CDCl$_3$) is consistent with the desired product; IR (KBr) 3000, 1740, 1660 cm$^{-1}$; MS (CI (low res)) m/e 209 (M+H), 191, 123.

PREPARATION 6, COMPOUND 10

4-(4-Acetyl-2-methylphenoxy)butanoic acid

Utilizing the procedure of Preparation 3, 2.00 g (13.32 mmol) of 4-hydroxy-3-methylacetophenone is alkylated with ethyl 4-bromobutyrate. This produces 3.45 g (98%) of 4-(4-acetyl-2-methylphenoxy)butanoic acid, ethyl ester as a golden oil, after drying at 75° C., under vacuum: IR (neat) 1740, 1675 cm$^{-1}$; $^1$H-NMR (CDCl$_3$) is consistent with the desired product; MS (FAB) m/e 265 (M$^+$+H). Analysis calculated for C$_{15}$H$_{20}$O$_4$: C, 68.16; H, 7.63; O, 24.21. Found: C, 67.92; H, 7.44; O, 24.64.

Following the method of Preparation 3, 2.50 g (9.46 mmol) of 4-(4-acetyl-2-methylphenoxy)butanoic acid, ethyl ester is saponified to give the desired compound as a solid. It is recrystallized from ethyl acetate/ether leaving 1.32 g (59%) of 4-(4-acetyl-2-methylphenoxy)butanoic acid as white crystals: m.p. 114°–16° C.; IR (KBr) 1730, 1650 cm$^{-1}$; $^1$H-NMR (CDCl$_3$) is consistent with the desired product; MS (FAB) m/e 237 (M$^+$+H). Analysis calculated for $C_{13}H_{16}O_4$: C, 66.08; H, 6.83; O, 27.09. Found: C, 65.88; H, 6.92; O, 27.20.

PREPARATION 7, COMPOUND 11

4-(4-Formyl-2-methoxyphenoxy)butanoic acid

4-Hydroxy-3-methoxybenzyl alcohol (1 g, 6.49 mmol) is treated with 1.73 g (7.13 mmol) of ethyl 4-bromobutyrate, 2.69 g (19.46 mmol) of potassium carbonate and a catalytic amount (97.22 mg 0.65 mmol) of sodium iodide as described in Preparation 3 to give 821 mg of 4-[4-(hydroxymethyl)-2-methoxyphenoxy]butanoic acid, ethyl ester as a light brown oil (47%). The $^1$H NMR (300 MHz, CDCl$_3$) is consistent with the desired product; IR (neat) 3500, 1730, 1620, 1600 cm$^{-1}$; MS (CI (low res)) m/e 269 (M+H), 251, 223, 195.

4-[4-(Hydroxymethyl)-2-methoxyphenoxy]butanoic acid, ethyl ester (431 mg, 1.61 mmol) is treated with 1.0 g (4.8 mmol) of pyridinium chlorochromate by the procedure described in Example 5 to give 280 mg (65%) of 4-(4-formyl-2-methoxyphenoxy)butanoic, ethyl ester as a colorless oil. The $^1$H NMR (300 MHz, CDCl$_3$) is consistent with the desired product; IR (neat) 1730, 1690, 1600, 1580 cm$^{-1}$.

4-(4-Formyl-2-methoxyphenoxy)butanoic acid, ethyl ester (240 mg, 0.90 mmol) is dissolved in 3 mL of methanol/water (3:2) and treated with 435 mg (3.15 mmol) of potassium carbonate according to the procedure described for Example 4 to give 125 mg (58%) of 4-(4-formyl-2-methoxyphenoxy)butanoic acid as a white powder: m.p. 143°–148°; the $^1$H NMR (300 MHz, CDCl$_3$) is consistent with the desired product; IR (KBr) 3575, 3500, 1720, 1700, 1680, 1600, 1585 cm$^{-1}$; MS (CI (low res)) m/e 239 (M+H), 221, 207, 153.

PREPARATION 8, COMPOUND 12

4-FormylbenzeneproDanoic acid

A mixture of 253 mg (1.44 mmol) of 4-formylcinnamic acid and 32.61 mg of platinum oxide in 10 mL of methanol is stirred overnight at room temperature under an atmosphere of hydrogen supplied by a balloon. The mixture is filtered through celite and concentrated in vacuo. The residue is dissolved in 0.1N sodium hydroxide solution and washed with ether. The aqueous layer is then acidified and the product is extracted with ethyl acetate. The organic layer is washed with saturated sodium chloride solution and dried over magnesium sulfate. The solvent is removed in vacuo to afford an inseparable mixture of 4-formylphenylpropanoic acid and other reduction products. The mixture is utilized in the next reaction without characterization or further purification.

PREPARATION 9, COMPOUND 13

4-(2,3-Dimethoxy-5-formylphenoxy)butanoic acid

Employing the method of Preparation 3, 3.30 g (18.41 mmol) of 3,4-dimethoxy-5-hydroxybenzaldehyde is alkylated with ethyl 4-bromobutyrate. 4-(2,3-Dimethoxy-5-formylphenoxy)butanoic acid, ethyl ester is obtained as a yellow-orange oil after drying under high vacuum at 60°0 C. (5.45 g, 100%): IR (neat) 1735, 1690 cm$^{-1}$; $^1$H-NMR (CDCl$_3$) is consistent with the desired product; MS (FAB) m/e 297 (M$^+$+H). Analysis calculated for $C_{15}H_{20}O_6$: C, 60.80; H, 6.80; O, 32.40. Found: C, 60.51; H, 6.86; O, 32.63.

Following the procedure of Preparation 3, a sample of 4.70 g (15.86 mmol) of 4-(2,3-dimethoxy-5-formylphenoxy)butanoic acid, ethyl ester is saponified giving the desired compound as a cream colored solid. This is recrystallized from ethyl acetate/ether, leaving 3.65 g (86%) of 4-(2,3-dimethoxy-5-formylphenoxy)butanoic acid as off-white crystals: m.p. 90°–92° C.; IR (KBr) 1710, 1690 cm$^{-1}$; $^1$H-NMR (CDCl$_3$) is consistent with the desired product; MS (FAB) m/e 269 (Me$^+$+H). Analysis calculated for $C_{13}H_{16}O_6$: C, 58.20; H, 6.01; O, 35.79. Found: C, 58.10; H, 6.09; O, 35.81.

PREPARATION 10, COMPOUND 14

4-(4-Acetyl-2,6-dimethoxyphenoxy)butanoic acid

Utilizing the procedure of Preparation 3, 2.61 g (13.32 mmol) of 4-acetyl-2,6-dimethoxyphenol is treated with ethyl 4-bromobutyrate. This gives the desired product after drying at −70° C., under high vacuum, as a brown oil. This is chromatographed on a column of silica gel, and eluted with a 1:1 mixture of ether/hexane leaving 0.40 g (10%) of 4-(4-acetyl-2,6-dimethoxyphenoxy)butanoic acid, ethyl ester as a colorless oil: IR (neat) 1735, 1675 cm$^{-1}$; $^1$H-NMR (CDCl$_3$) is consistent with the desired product; MS (FAB) m/e 311.1489 Δ=+0.6 mm$\mu$ (M$^+$+H). Analysis calculated for $C_{16}H_{22}O_6$: C, 61.92; H, 7.14; O, 30.94. Found: C, 61.48; H, 7.04; O, 31.48.

Following the method of Preparation 3, 0.179 g (0.577 mmol) of 4-(4-acetyl-2,6-dimethoxyphenoxy)-butanoic acid, ethyl ester is treated with potassium carbonate, producing an off-white solid. Recrystallization from ethyl acetate/hexane gives 4-(4-acetyl-2,6-dimethoxyphenoxy)butanoic acid as white crystals (0.14 g, 88%): m.p. 122°–24° C.; IR (KBr) 1735, 1660 cm$^{-1}$; $^1$H-NMR (CDCl$_3$) is consistent with the desired product; MS (FAB) m/e 283 (M$^+$+H). Analysis calculated for $C_{14}H_{18}O_6$: C, 59.57; H, 6.43; O, 34.01. Found: C, 59.34; H, 6.40; O, 34.26.

PREPARATION 11, COMPOUND 15

4-(4-Acetyl-2-methoxyphenoxy)butanoic acid

Employing the procedure of Preparation 3, 2.21 g (13.32 mmol) of 4-hydroxy-3-methoxyacetophenone is alkylated, producing a solid. This is recrystallized as in Preparation 3, leaving 3.23 g (86%) of 4-(4-acetyl-2-methoxyphenoxy)butanoic acid, ethyl ester as white crystals: m.p. 53°–55° C.; IR (KBr) 1745, 1675 cm$^{-1}$; $^1$H-NMR (CDCl$_3$) is consistent with the desired product; MS (FAB) m/e 281 (M$^+$+H). Analysis calculated for $C_{15}H_{20}O_5$: C, 64.27; H, 7.19; O, 28.54. Found: C, 64.26; H, 7.05; O, 28.69.

Following the method of Preparation 3, 2.74 g (9.78 mmol) of 4-(4-acetyl-2-methoxyphenoxy)butanoic acid, ethyl ester is saponified. This produces 4-(4-acetyl-2-methoxyphenoxy)butanoic acid as off-white crystals after recrystallization from ethyl acetate (1.61 g, 87%): m.p. 161°–63° C.; IR (KBr) 1720, 1670 cm$^{-1}$; $^1$H-NMR (CDCl$_3$) is consistent with the desired product; MS (FAB) m/e 253 (M$^+$+H). Analysis calculated for $C_{13}H_{16}O_5$: C, 61.90; H, 6.39; O, 31.71. Found: C, 61.75; H, 6.37; O, 31.88.

PREPARATION 12, COMPOUND 16

4-[4-(3-Oxobutyl)phenoxy]butanoic acid

4-Hydroxybenzylacetone (2 g, 12.18 mmol) is treated with 2.61 g (13.4 mmol) of ethyl 4-bromobutyrate, 5.05 g (36.5 mmol) of potassium carbonate and a catalytic amount (182 mg 1.22 mmol) of sodium iodide in 2 mL N,N-dimethylformamide as described in Preparation 3 to give 2.73 g of 4-[4-(3-oxobutyl)phenoxy]-butanoic, ethyl ester as a light brown oil (80%): m.p. 32°–34°; the $^1$H NMR (300 MHz, CDCl$_3$) is consistent with the desired product; IR (neat) 1730, 1720, 1610, 1580, 1510 cm$^{-1}$; MS (CI (low res)) m/e 279 (M+H), 233, 221; Analysis calculated for C$_{16}$H$_{22}$O$_4$: C, 69.04; H, 7.97; found: C, 68.33; H, 7.68.

4-[4-(3-Oxobutyl)phenoxy]butanoic acid, ethyl ester (716 mg, 2.57 mmol) is dissolved in 5 mL of methanol/water (3:2) and treated with 1.24 g (9.0 mmol) of potassium carbonate according to the procedure described for Example 4 to give 385 mg (60%) of 4-[4-(3-oxobutyl)phenoxy]butanoic acid as a white powder: m.p. 97°–99°; the $^1$H NMR (300 MHz, CDCl$_3$) is consistent with the desired product; IR (neat) 1730, 1700, 1620, 1520 cm$^{-1}$; Analysis calcld for C$_{14}$H$_{18}$O$_4$: C, 67.18; H, 7.25; found: C, 66.55; H, 7.09.

EXAMPLE 13, COMPOUND 17

4-(2-Acetyl-5-methoxyphenoxy)butanoic acid

Following the procedure of Preparation 3, 2.21 g (13.32 mmol) of 2-hydroxy-4-methoxyacetophenone is alkylated and worked up as before to leave 3.40 g (91%) of 4-(2-acetyl-5-methoxyphenoxy)butanoic acid, ethyl ester as a yellow oil: IR (neat) 1740, 1665 cm$^{-1}$; $^1$H-NMR (CDCl$_3$) is consistent with the desired product; MS (FAB) m/e 281 (M$^+$+H). Analysis calculated for C$_{15}$H$_{20}$O$_5$: C, 64.27; H, 7.19; O, 28.54. Found: C, 64.06; H, 7.24; O, 28.70.

Utilizing the method of Preparation 3, 2.50 g (8.92 mmol) of 4-(2-acetyl-5-methoxyphenoxy)butanoic acid, ethyl ester is treated with potassium carbonate, producing a white solid. This is recrystallized from ethyl acetate/ether leaving 1.61 g (71%) of 4-(2-acetyl-5-methoxyphenoxy)butanoic acid as colorless crystals: m.p. 127°–29° C.; IR (KBr) 1720, 1655 cm$^{-1}$; $^1$H-NMR (CDCl$_3$) is consistent with the desired product; MS (FAB) m/e 253 (M$^+$+H). Analysis calculated for C$_{13}$H$_{16}$O$_5$: C, 61.90; H, 6.39; O, 31.71. Found: C, 61.82; H, 6.37; O, 31.81.

PREPARATION 14, COMPOUND 18

4-[4-(3-Oxopropyl)phenoxy]butanoic acid

Following the procedure of Preparation 3, 2.80 g (18.41 mmol) of 3-(4-hydroxyphenyl-1-propanol) is alkylated with ethyl 4-bromobutyrate. The product is dried at 70° C., under high vacuum, leaving 4.70 g (96%) of 4-[4-(3-hydroxypropyl)phenoxy]butanoic acid, ethyl ester as a colorless oil: IR (neat) 3400 (br.), 1735 cm$^{-1}$; $^1$H-NMR (CDCl$_3$) is consistent with the desired product; MS (CI) m/e 267 (M$^+$+H). Analysis calculated for C$_{15}$H$_{22}$O$_4$: C, 67.65; H, 8.33; O, 24.03. Found: C, 67.40; H, 8.20; O, 24.38.

After the method of Preparation 3, 4.13 g (15.51 mmol) of 4-[4-(3-hydroxypropyl)phenoxy]butanoic acid, ethyl ester is saponified with potassium carbonate to produce a solid. This is recrystallized from an ethyl acetate-hexane mixture giving 2.45 (66%) of 4-[4-(3-hydroxypropyl)phenoxy]butanoic acid as white crystals: m.p. 92°–94° C.; IR (KBr) 3420 (br.), 1710 cm$^{-1}$; $^1$H-NMR (CDCl$_3$) is consistent with the desired product; MS (CI) m/e 239 (M$^+$+H). Analysis calculated for C$_{13}$H$_{18}$O$_4$: C, 65.53; H, 7.61; O, 26.86. Found: C, 65.75; H, 7.87; O, 26.38.

A 1.19 g (5.00 mmol) sample of 4-[4-(3-hydroxypropyl) phenoxy]butanoic acid is dissolved with stirring in 250 mL of methylene dichloride. Next, 3.77 g (17.49 mmol) of pyridinium chlorochromate is added, the mixture is stirred for 4 hr, and then filtered through a celite pad. The reaction mixture is then diluted with an equal volume of ether, precipitating out salts. This mixture is then filtered through a silica gel pad, and the filtrate evaporated, giving a brown solid. The solid is recrystallized from an ether-hexane mixture producing 0.21 (18%) of 4-[4-(3-oxopropyl)phenoxy] butanoic acid as off-white crystals: m.p. 100°–03° C.; IR (KBr) 1715 cm$^{-1}$; $^1$H-NMR (CDCl$_3$) is consistent with the desired product; MS (CI) m/e 237 (M$^+$+H). Analysis calculated for C$_{13}$H$_{16}$O$_4$: C, 66.09; H, 6.83; O, 27.09. Found: C, 65.91; H, 6.72; O, 27.35.

EXAMPLE 15, COMPOUND 20

4-[(2-Acetyl-1-naphthalenyl)oxy]butanoic acid

A 3.42 g (18.37 mmol) sample of 1-hydroxy-2-acetonapthone is alkylated as in Preparation 3. The crude product is dried under high vacuum at 60° C. to give 5.21 g (94%) of 4-[(2-acetyl-1-naphthalenyl)oxy]butanoic acid, ethyl ester as a golden liquid: IR (neat) 1730, 1665 cm$^{-1}$; $^1$HNMR (CDCl$_3$) is consistent with the desired product; MS (FAB) m/e 301(M$^+$+H). Analysis calculated for C$_{18}$H$_{20}$O$_4$: C, 71.98; H, 6.71; O, 21.31. Found: C, 72.11; H, 6.58; O, 21.31.

Utilizing the method of Preparation 3, 2.84 g (9.46 mmol) of 4-[(2-acetyl-1-naphthalenyl)oxy]butanoic acid, ethyl ester is saponified. The crude product is recrystallized from ethyl acetate/ether to give 1.15 g (45%) of 4-[(2-acetyl-1-naphthalenyl)oxy]butanoic acid as golden crystals: m.p. 104°–06° C.; IR (KBr) 1720, 1640 cm$^{-1}$; $^1$HNMR (CDCl$_3$) is consistent with the desired product; MS (FAB) m/e 273 (M$^+$+H). Analysis calculated for C$_{16}$H$_{16}$O$_4$: C, 70.58; H, 5.92; O, 23.50. Found: C, 70.40; H, 5.89; O, 23.71.

PREPARATION 16, COMPOUND 21

4-[4-(4-Fluorobenzoyl)phenoxy]butanoic acid

Following the method of Preparation 3, 3.98 g (18.41 mmol) of 4-fluoro-4'-hydroxybenzophenone is alkylated with ethyl 4-bromobutyrate. The crude yellow solid product is recrystallized from ether providing 2.97 g (49%) of 4-[4-(4-fluorobenzoyl)phenoxy]butanoic acid, ethyl ester as white crystals: m.p. 57°–59° C.; IR (KBr) 1735, 1645 cm$^{-1}$; $^1$HNMR (CDCl$_3$) is consistent with the desired product; MS (FAB) m/e 311 (M$^+$+H). Analysis calculated for C$_{19}$H$_{19}$O$_4$F: C, 69.08; H, 5.80; F, 5.75; O, 19.37. Found: C, 69.09; H, 5.62; F, 5.95; O, 19.34.

Utilizing the procedure of Preparation 3, 0.48 g (1.45 mmol) of 4-[4-(4-fluorobenzoyl)phenoxy]butanoic acid, ethyl ester is saponified. The crude white solid product is recrystallized from an ether-hexane mixture leaving 0.16 g (36%) of 4-[4-(4-fluorobenzoyl)phenoxy]butanoic acid as white crystals: m.p. 109°–111° C.; IR (KBr) 1735, 1700 1640 cm$^{-1}$; $^1$HNMR (CDCl$_3$) is consistent with the desired product; MS (FAB) m/e 303 (M$^+$+H). Analysis calculated for C$_{17}$H$_{15}$O$_4$F: C, 67.54; H, 5.00; F, 6.28; O, 21.18. Found: C, 67.28; H, 4.89; F, 6.41; O, 21.42.

EXAMPLE 17, COMPOUND 22

4-(4-Acetylphenyl)-1-piperazinevaleric acid

4'-Piperazinoacetophenone (102 mg) is dissolved in 1 mL of N,N-dimethylformamide. After addition of methyl 5-bromovalerate (0.077 mL) and potassium carbonate (69 mg), the mixture is stirred at room temperature for 65 hours. TLC (10% MeOH/CH$_2$Cl$_2$) should show a single product spot without residual starting material. The reaction solution is evaporated under vacuum. The residue is taken up in methylene chloride, washed twice with water and dried over sodium sulfate. Evaporation of the solvent yields 137 mg of 4-(4-acetylphenyl)-1-piperazinevaleric acid, methyl ester as yellow crystals whose $^1$H-NMR (CDCl$_3$) spectrum is consistent with the assigned structure.

4-(4-Acetylphenyl)-1-piperazinevaleric acid, methyl ester (15.3 mg) is suspended in 0.1 mL of potassium hydroxide solution (33.2 mg/mL). After heating at 100° C. for 150 min, the starting material is completely dissolved and absent by TLC (10% MeOH/CH$_2$Cl$_2$). After acidifying the reaction solution to pH 4 by adding 0.2N HCl, the aqueous solution is extracted with methylene chloride. After evaporation of the organic layer to dryness, the residue is dissolved in methylene chloride and filtered. Evaporation of the organic layer gives 7 mg of 4-(4-acetylphenyl)-1-piperazinevaleric acid as a white solid. $^1$H-NMR (CDCl$_3$) spectrum is consistent with the assigned structure. MS (FAB) m/e 305 (M$^+$+H), 327 (M$^+$+Na), 348 (M$^+$+2Na—H).

PREPARATION 18, COMPOUND 25

4-(2–Chloro-4-formylphenoxy)butanoic acid

Following the procedure of Preparation 3, 2.88 g (18.41 mmol) of 3-chloro-4-hydroxybenzaldehyde is alkylated as before. This produces 4.65 g (93%) of 4-(2-chloro-4-formylphenoxy)butanoic acid, ethyl ester as an orange oil: IR (neat) 1730, 1685 cm$^{-1}$; $^1$HNMR (CDCl$_3$) is consistent with the desired product; MS (CI) m/e 271 (M$^+$+H). Analysis calculated for C$_{13}$H$_{15}$O$_4$Cl: C, 57.68; H, 5.58; Cl, 13.10; O, 23.64. Found: C, 58.05; H, 5.37; Cl, 12.43; O, 24.15.

After the method of Preparation 3, 3.52 g (13.00 mmol) of 4(2-chloro-4-formylphenoxy)butanoic acid, ethyl ester is saponified to give a white solid. This is recrystallized from ethyl acetate resulting in 1.78 g (56%) of 4-(2-chloro-4-formylphenoxy)butanoic acid as white crystals: m.p. 128°–31° C.; IR (KBr) 1730, 1650 cm$^{-1}$; $^1$HNMR (CDCl$_3$) is consistent with the desired product; MS (CI) m/e 243 (M$^+$+H). Analysis calculated for C$_{11}$H$_{11}$O$_4$Cl: C, 54.45; H, 4.57; Cl, 14.61; O, 26.37. Found: C, 54.61; H, 4.70; Cl, 14.25; O, 26.42.

EXAMPLE 19, COMPOUND 26

5-Acetyl-2-(3-carboxypropoxy)benzoic acid, methyl ester

Under dry condition, 3.58 g (18.41 mmol) of 5-acetylsalicylic acid, methyl ester is dissolved in 25 mL of dry N,N-dimethylformamide. To this solution is added 3.07 g (20.58 mmol) of 5-bromo-1-pentene, 6.83 (20.58 mmol) of potassium carbonate, and 0.246 g (1.65 mmol) of potassium iodide, and the reaction mixture is stirred for 24 hours at ambient temperature. Another portion of 5-bromopentene is added to the reaction, followed by one-half portions of the other two reagents above, and stirring is continued for 72 hours. The mixture is then evaporated under high vacuum at 70° C. The residue is partitioned between ether/water and the organic phase is separated, dried with magnesium sulfate, filtered, and evaporated under vacuum to leave 4.60 g (95%) of 5-acetyl-2-(4-pentenyloxy)benzoic acid, methyl ester as a yellow liquid: IR (neat) 1735, 1710, 1680 cm$^{-1}$; $^1$HNMR (CDCl$_3$) is consistent with the desired product; MS (FAB) mle 263 (M$^+$+H). Analysis calculated for C$_{15}$H$_{18}$O$_4$: C, 68.69; H, 6.92; O, 24.40. Found: C, 68.60; H, 6.92; O, 24.46.

A sample of 0.203 g (0.775 mmol) of 5-acetyl-2-(4-pentenyloxy)benzoic acid, methyl ester is dissolved in 5 mL of methylene dichloride, under an argon atmosphere, and cooled to −78° C. in a dry ice acetone bath, with stirring. Next, ozone gas is passed through this solution for 10 min, until it turns a light bluish color. Then 0.5 mL of dimethyl sulfide is added to quench the reaction and it is allowed to warm to room temperature for 2 hours. The mixture is then evaporated under high vacuum, leaving the crude aldehyde product as an oil which is used "as is" for the second step. It is dissolved in 5 mL of N,N-dimethylformamide, and 1.02 g (2.71 mmol) of pyridinium dichromate is added. This reaction mixture is sealed and allowed to stand for 20 hours. It is next poured into 50 mL of water, extracted with ether, and the organic phase is washed with water again, dried with magnesium sulfate, filtered, and evaporated, which gives oily crystals. These are recrystallized from a mixture of ethyl acetate and hexane, producing 0.109 g (50%) of 5-acetyl-2-(3-carboxypropoxy)benzoic acid, methyl ester as white crystals: m.p. 111°–113° C.; IR (KBr) 1725, 1645 cm$^{-1}$; $^1$HNMR (CDCl$_3$) is consistent with the desired product; MS (FAB) m/e 281 (M$^+$+H). Analysis calculated for C$_{14}$H$_{16}$O$_6$: C, 60.00; H, 5.75; O, 34.25. Found: C, 59.96; H, 5.75; O, 34.27.

PREPARATION 20, COMPOUND 27

4-(4-Formyl-2-nitrophenoxy)butanoic acid

4-Hydroxy-3-nitrobenzyl alcohol (1 g, 5.91 mmol) is treated with 1.44 g (7.39 mmol) of ethyl 4-bromobutyrate, 2.86 g (20.69 mmol) of potassium carbonate and a catalytic amount (88 mg .59 mmol) of sodium iodide as described in Preparation 3 to give 1.45 g of 4-[4-(hydroxymethyl)2-nitrophenoxy]butanoic acid, ethyl ester as a light yellow oil (86%). The $^1$H NMR (300 MHz, CDCl$_3$) is consistent with the desired product; IR (neat) 3400, 1730, 1710, 1630, 1580 cm$^{-1}$; MS (CI) m/e 284 (M+H), 238; Analysis calculated for C$_{13}$H$_{17}$O$_6$N: C, 55.12;

H, 6.05; found: C, 55.36; H, 6.03.

4-[4-(Hydroxymethyl)2-nitrophenoxy]butanoic acid, ethyl ester (300 mg, 1.06 mmol) is treated with 799 mg (3.71 mmol) of pyridinium chlorochromate by the procedure described in Example 5 to give 188 mg (63%) of 4-(4-formyl-2-nitrophenoxy)butanoic acid, ethyl ester as a colorless oil. The $^1$H NMR (300 MHz, CDCl$_3$) is consistent with the desired product; IR (neat) 1730, 1700, 1610, 1570 cm$^{-1}$; MS (CI) m/e 282 (M+H).

4-(4-Formyl-2-nitrophenoxy)butanoic acid, ethyl ester (135 mg, 0.48 mmol) is dissolved in 3 mL of methanol/water (3:2) and treated with 232 mg (1.68 mmol) of potassium carbonate according to the procedure described for Example 4 to give 84 mg (69%) of 4-(4-formyl-2-nitrophenoxy) butanoic acid as a yellow powder: m.p. 136°–139°; the $^1$H NMR (300 MHz, CDCl$_3$) is consistent with the desired product; IR (KBr) 3400, 1730, 1700, 1650, 1600, 1570 cm$^{-1}$; MS (CI) m/e 254, 236, 224, 208, 196, 168.

EXAMPLE 21, COMPOUND 28

4-[2- [[(4-Acetylphenyl)amino]methyl]-6-methoxyphenoxy]butanoic acid

4'-(2-Hydroxy-3-methoxybenzylamino)acetophenone (500 mg, 1.84 mmol) is treated with 629 mg (3.22 mmol) of ethyl 4-bromobutyrate, 764 mg (5.53 mmol) of potassium carbonate and a catalytic amount (182 mg, 1.22 mmol) of sodium iodide in 2 mL N,N-dimethylformamide as described in Preparation 3 to give 680 mg of 4-[2-[[(4-acetylphenyl)amino]methyl]-6-methoxyphenoxy]butanoic acid, ethyl ester as a light brown oil (95%). The $^1$H NMR (300 MHz, CDCl$_3$) is consistent with the desired product; IR (neat) 3400, 1730, 1660, 1600 cm$^{-1}$; MS (CI) m/e 386 (M+H), 115; Analysis calculated for C$_{22}$H$_{27}$O$_5$N: C, 68.55; H, 7.06; N, 3.63; found: C, 68.27; H, 6.81; N, 3.54.

4-[2-[[(4-Acetylphenyl)amino]methyl]-6-methoxy-phenoxy]butanoic acid, ethyl ester (250 mg, 0.65 mmol) is dissolved in 5 mL of methanol/water (3:2) and treated with 313 mg (2.27 mmol) of potassium carbonate according to the procedure described for Example 4 to give 166 mg (71%) of 4-[2-[[(4-acetylphenyl)amino]-menthyl]-6-methoxy-phenoxy]butanoic acid as a red colored solid: m.p. 85°–95° C.; The $^1$H NMR (300 MHz, CDCl$_3$) is consistent with the desired product; IR (KBr) 3400, 1720, 1630, 1580 cm$^{-1}$; MS (CI) m/e calculated for C$_{20}$H$_{23}$O$_5$NNa: 380.1473, found 380.1482; 358 (M+H), 233, 223, 221, 136.

EXAMPLE 22, COMPOUND 29

5-Acetyl-2-(3-carboxyproroxy)-benzoic acid, 1-(3-bromorropyl) ester

To a solution of 0.744 g (3.00 mmol) of 5-acetyl-2-(4-pentenyloxy)-benzoic acid (Example 19), under an argon atmosphere, with stirring, in 36 mL of methylene dichloride, is added 1.67 g (12.0 mmol) of 3-bromopropanol. This is followed by 0.912 g (9.0 mmol) of triethyl amine and by 1.66 g (3.75 mmol) of benzotriazol-1-yloxytris (dimethylamino) phosphonium hexafluorophosphate and the reaction is stirred for 20 hours. The mixture is then evaporated, under high vacuum at 65° C. The residue is partitioned between ether and water, the ether phase is washed twice more with water, dried with magnesium sulfate, filtered, and evaporated leaving a gum. This is chromatographed on a column of silica gel, and eluted with ethyl acetate/hexane (1:2) to give 0.80 g (72%) of 5-acetyl-2-(4-pentenyloxy)-benzoic acid, 1-(3-bromopropyl) ester as a colorless oil: IR (neat) 1730, 1700, 1680 cm$^{-1}$; $^1$HNMR (CDCl$_3$) is consistent with the desired product; MS (FAB) m/e 369 (M$^+$+H). Analysis calculated for C$_{17}$H$_{21}$O$_4$Br: C, 55.30; H, 5.73; O, 17.33; Br 21.64. Found: C, 55.34; H, 5.44; O, 17.34; Br 21.88.

Following the procedure of Example 19, 0.377 g (1.02 mmol) of 5-acetyl-2-(4-pentenyloxy)-benzoic acid, 1-(3-bromopropyl) ester is ozonized, and then further oxidized with pyridinium dichromate producing a colorless gum which partially crystallizes. This is recrystallized from a mixture of equal parts of ethyl acetate and hexane leaving 0.277 g (70%) of 5-acetyl-2-(3-carboxypropoxy)-benzoic acid, 1-(3-bromopropyl) ester as white crystals: m.p. 103°–05° C.; IR (KBr) 1730, 1645 cm$^{-1}$; $^1$HNMR (CDCl$_3$) is consistent with the title product; MS (CI) m/e 389 (M$^+$+H). Analysis calculated for C$_{16}$H$_{19}$O$_6$Br: C, 49.63; H, 4.95; O, 24.79; Br, 20.63. Found: C, 49.90; H, 4.75; O, 24.94; Br, 20.39.

PREPARATION 23, COMPOUND 30

4-(4-Acetyl-3-fluorophenoxy)butanoic acid

A solution of 2-fluoro-4-methoxyacetophenone in 5 mL of DMSO is stirred at 100° C. in the presence of 730 mg (15 mmol) of sodium cyanide to give a dark viscous sludge. The mixture is allowed to cool, then poured into 50 mL of ice water and acidified with 6N aqueous HCl. The acidic solution is extracted with ethyl acetate (50 mL×2) and the organic layers are combined and washed with water. The organic layer is then extracted twice with 1.0N aqueous sodium hydroxide solution. The basic layer is washed once with ether, then acidified with solid sodium bisulfate and extracted with ethyl acetate twice. The ethyl acetate layers are combined, then washed with 10% sodium bisulfate solution and saturated sodium chloride solution. The organic phase is dried over magnesium sulfate and concentrated in vacuo at ambient temperature to give 143 mg (31%) of an oil.

The oil isolated above is dissolved in 1 mL of N,N-dimethylformamide and treated with 205 mg (1.05 mmol) of ethyl 4-bromobutyrate, 4.07 g (2.95 mmol) of potassium carbonate and a catalytic amount (1.26 mg, 0.008 mmol) of sodium iodide according to the procedure described in Preparation 3 to give 39 g of 4-(4-acetyl-3-fluorophenoxy) butanoic acid, ethyl ester as a light brown oil (17%). The $^1$H NMR (300 MHz, CDCl$_3$) is consistent with the desired product; MS (CI (low res)) m/e calculated for C$_{14}$H$_{18}$O$_4$F: 269.1189, found 269.1191.

4-(4-Acetyl-3-fluorophenoxy)butanoic acid, ethyl ester (20 mg, 0.0745 mmol) is dissolved in 1 mL of methanol/ water (3:2) and treated with 30.91 mg (0.22 mmol) of potassium carbonate according to the procedure described for Example 4 to give 14 mg (82%) of 4-(4-acetyl-3-fluorophenoxy)butanoic acid as a white powder: m.p. 110°–111° C.; The $^1$H NMR (300 MHz, CDCl$_3$) is consistent with the desired product; IR (KBr) 1710, 1670, 1610 cm$^{-1}$; MS m/e calculated for C$_{12}$H$_{13}$O$_4$FNa: 263.0695, found 263.0699.

EXAMPLE 24, COMPOUND 31

(2-Acetyl-henoxy)butanoic acid

2-Acetylphenol (1 g, 7.34 mmol) is treated with 1.79 g (9.18 mmol) of ethyl 4-bromobutyrate, 3.55 g (25.71 mmol) of potassium carbonate and a catalytic amount (11 mg, 0.07 mmol) of sodium iodide as described in Preparation 3 to give 1.84 g of (2-acetylphenoxy)-butyric acid, ethyl ester as a light yellow oil which solidified upon standing: m.p. 43°–45° C.; The $^1$H NMR (300 MHz, CDCl$_3$) is consistent with the desired product; IR (neat) 1730, 1660, 1600 cm$^{-1}$; MS (CI) m/e 251 (M+H), 232, 205.

(2-Acetylphenoxy)butanoic acid, ethyl ester (500 mg, 2.00 mmol) is dissolved in 3 mL of methanol/water (3:2) and treated with 828 mg (5.99 mmol) of potassium carbonate according to the procedure described for Example 4 to give 412 mg (93%) of (2-acetylphenoxy)butanoic acid as a white powder. The $^1$H NMR (300 MHz, CDCl$_3$) is consistent with the desired product; IR (KBr) 1710, 1670, 1590 cm$^{-1}$; MS m/e calculated for C$_{12}$H$_{15}$O$_4$: 223.0970, found 223.0971.

EXAMPLE 25, COMPOUND 32

2-Acetyl-10H-phenothiazine-10-hexanoic acid

A solution of 500 mg (2.07 mmol) of 2-acetylphenothiazine in 8 mL of tetrahydrofuran is cooled to −78° C. and 4.14 mL (2.07 mmol) of a 0.5M solution of potassium bis(trimethylsilyl)amide in toluene is added. After five minutes, a solution of [(6-bromohexyl)oxy]-(1,1-dimethylethyl)dimethyl silane in 2 mL of tetrahydrofuran is added and the reaction is allowed to warm to room temperature. The mixture is diluted with 25 mL of ethyl acetate and washed with 10% sodium bisulfate solution and saturated sodium chloride solution, then dried over magnesium sulfate and concentrated in vacuo to give a dark colored residue. Flash chromatography (3:1 hexane/ethyl acetate) provides 318 mg (33%) of 1-[10-[6-[[(1,1-dimethylethyl) dimethylsilyl]oxy]hexyl]-10H-phenothiazin-2-yl]ethanone as a dark colored oil. The $^1$H NMR (300 MHz, CDCl$_3$) is consistent with the desired product; IR (neat) 1680, 1600, 1560 cm$^{-1}$; MS m/e calculated for C$_{26}$H$_{37}$NO$_2$SSi: 455.2314, found 455.2312.

A solution of 150 mg (0.33 mmol) of 1-[10-[6-[[(1,1-dimethylethyl)dimethylsilyl]oxy]hexyl]-10H-phenothiazin-2-yl]ethanone in 0.6 mL of tetrahydrofuran is treated with 0.41 mL (0.41 mmol) of 1M tetrabutylammonium fluoride in tetrahydrofuran. The reaction is stirred for 3 hours at room temperature, then diluted with 20 mL of ethyl acetate. The organic layer is washed successively with 10% sodium bisulfate solution and saturated sodium chloride solution, then dried over magnesium sulfate and concentrated in vacuo to give 114 mg of 1-[10-(6-hydroxyhexyl)-10H-phenothiazin-2-yl]ethanone as a dark oil. The $^1$H NMR (300 MHz, CDCl$_3$) is consistent with the desired product; IR (neat) 3400, 1680, 1590, 1560 cm$^{-1}$; MS m/e calculated for C$_{20}$H$_{23}$NO$_2$S: 341.1449, found 341.1456.

A solution of 41 mg (0.12 mmol) of 1-[10-(6-hydroxyhexyl)-10H-phenothiazin-2-yl]ethanone in 0.16 mL of N,N-dimethylformamide is treated with 158 mg (0.42 mmol) of pyridinium dichromate and stirred at room temperature for 12 hours. The mixture is diluted with ether and filtered through a pad of celite with the aid of 100 mL of ether. The filtrate is washed successively with 10% sodium bisulfate solution and saturated sodium chloride solution, then dried over magnesium sulfate and concentrated in vacuo to give 10 mg (23%) of 2-acetyl-10H-phenothiazine-10-hexanoic acid as a dark residue. The $^1$H NMR (300 MHz, CDCl$_3$) is consistent with the desired product. MS (CI) m/e 323 (M$^+$+H).

EXAMPLE 26, COMPOUND 34

5-Acetyl-2-(3-carboxypropoxy)-N-(2-dimethylaminoethyl)-benzamide

A sample of 0.140 g (0.50 mmol) of 5-acetyl-2-(3-carboxypropoxy)-benzoic acid, methyl ester (Example 19) is heated on a steam bath, under dry conditions with 5.49 mL (50.0 mmol) of N,N-dimethylethylenediamine for 5 hours. The mixture is allowed to cool for 20 hours to ambient temperature and evaporated under vacuum at 55° C. The brown gum produced is triturated with ether, and the remaining residue taken up in water and acidified with hydrochloric acid. This is then extracted with ethyl acetate, and the aqueous solution is evaporated under vacuum, leaving a gum. It is next triturated with hot chloroform and this solution is evaporated to give a brown glass. This is chromatographed on a preparatory silica gel plate which is eluted with a 9/1 mixture of chloroform to methanol. The product band is cut from the plate, triturated with the above solvent mixture, filtered, and evaporated leaving 0.025 g (15%) of 5-acetyl-2-(3-carboxypropoxy)-N-(2-dimethylaminoethyl)-benzamide as a light brown gum: MS (FAB) m/e 337.1753 Δ=+0.9 mm$\mu$ (M$^+$+H), 359 (M$^+$+Na). $^1$HNMR (CDCl$_3$) is consistent with the desired product.

EXAMPLE 27, COMPOUND 35

5-Acetyl-2-(3-carboxyproroxy)-N-(2-trimethylaminoethyl)-benzamide, internal salt To 100 mg of 5-acetyl-2-(3-carboxypropoxy)-N-(2-dimethylaminoethyl)-benzamide in 2 mL of methanol and 8 mL of pH 8.6 phosphate buffer is added 0.5 mL of dimethyl sulfate. The reaction pH is monitored about every 30 minutes and 0.1N sodium hydroxide is added as needed to return the pH to ~8.5. After 4 hours the solvents are removed under vacuum and the product is purified on BioSil A with a methanol-in-chloroform gradient to give 5-acetyl-2-(3-carbomethoxypropoxy)-N-(2-trimethylaminoethyl)-benzamide, chloride which is taken on to the next step. $^1$H-NMR (CDCl$_3$): 8.6 ppm (1H, d), 8.1 ppm (1H, dd), 7.1 ppm (1H, d), 4.3 ppm (2H, t), 4.0 ppm (2H, br t), 3.9 ppm (2H, br s), 3.7 ppm (3H, s), 3.7 ppm (1H, t), 3.3 ppm (9H, s), 2.1 ppm (3H, s), 2.1 ppm (2H, t), 2.3 ppm (2H, m).

The above product is dissolved in 2 mL of tetrahydrofuran and treated with an excess of 1N sodium hydroxide for 16 hours at ambient temperature. The organic cosolvent is removed under vacuum and the aqueous solution which remains is acidified with 1N HCl to a pH of about 5. The solution is then evaporated under vacuum to give a glass which crystallizes on standing. The resultant 5-acetyl-2-(3-carboxypropoxy)-N-(2-trimethylaminoethyl)benzamide, internal salt can be used without further purification. MS (FAB) m/e 351 (M$^+$+H).

EXAMPLE 28, COMPOUND 36

5-Acetyl-2-[N-(2-dimethylaminoethyl)-3-carboxamidopropoxy]benzoic acid, internal salt To 1.16 g of 5-acetylsalicylic acid, methyl ester in 10 mL of N,N-dimethylformamide is added 1 g of chloroacetic acid, methyl ester and 1.2 g of potassium carbonate. After stirring this mixture at ambient temperature for 16 hours the reaction is filtered, diluted with ethyl acetate, and washed once with water and twice with brine. The ethyl acetate is dried with magnesium sulfate, filtered, and evaporated to give 5-acetyl-2-(carboxymethoxy)benzoic acid as a crude product. Crystallization from methanol at −15° C. gives 0.6 g of white crystals. $^1$H-NMR (CDCl$_3$): 8.5 ppm (1H, d), 8.1 ppm (1H, dd), 6.9 ppm (1H, d), 4.8 ppm (2H, s), 4.0 ppm (3H, s), 3.8 ppm (3H, s), 2.6 ppm (3H, s). 450 mg of the above product is stirred in 1 mL of N,N-dimethylethylenediamine at ambient temperature for 16 hours. The reaction is then diluted with ethyl acetate and water. The water layer is extracted five times with ethyl acetate and the ethyl acetate from the various extractions is pooled, dried with magnesium sulfate, filtered, and evaporated to give 380 mg of 5-acetyl-2-[N-(2-dimethylaminoethyl)-3-carboxamidopropoxy]benzoic acid, methyl ester as a yellowish oil which is pure enough for further use. $^1$H-NMR (CDCl$_3$): 8.6 ppm (1H, d), 8.2 ppm (1H, dd), 8.1 ppm (1H, br t), 7.0 ppm (1H, d), 4.7 ppm (2H, s), 4.0 ppm (3H, s), 3.5 ppm (2H, q), 2.7 ppm (3H, s), 2.6 ppm (2H, t), 2.3 ppm (6H, s).

To 280 mg of the above compound in 15 mL of methanol and 5 mL of chloroform is added 1 mL of methyl iodide. After 3 hr at ambient temperature the volatile components are removed. 1H-NMR indicates the presence of the desired 5-acetyl-2-[N-(2-trimethylaminoethyl)-3-carboxamidopropoxy]benzoic acid, methyl ester, iodide. $^1$H-NMR (CDCl$_3$+CD$_3$OD): 8.8 ppm (1H, br t), 8.6 ppm (1H, d), 8.2 ppm (1H, dd), 7.1 ppm (1H, d), 4.7 ppm (2H, s), 4.0 ppm (3H, s), 3.9 ppm (2H, q), 3.8 ppm (2H, t), 3.4 (9H, s), 2.6 ppm (3H, s).

The above compound is dissolved in ~5 mL of methanol. Five equivalents of sodium hydroxide is added as a 5N solution in water. After 5 hours at ambient temperature the pH is adjusted to ~7.5 with dilute HCl and the volatile components are removed under vacuum to give a crude product containing 5-acetyl-2-[N-(2-trimethylaminoethyl)-3-carboxamidopropoxy]benzoic acid, internal salt. MS (CI) m/e 323 (M$^+$+H).

SYNTHESIS OF STRUCTURES B (Scheme 1)
General Procedure

The drug-hydrazide derivative (Q-Sp-S-S-W wherein Q=$H_2$NHN—) is dissolved in alcohol or other compatible organic solvent containing ~3 to 10 equivalents of the carbonyl linker and ~1–10% acetic acid or other appropriate acid catalyst. A minimal amount of solvent gives a faster reaction. Anhydrous conditions give the best results as the condensation is an equilibrium reaction. The reaction is allowed to proceed at a temperature of ~20°–60° C. until complete by HPLC or alternately by TLC. This requires from a few hours to a day or more depending on the linker and the specific reaction conditions. The solvents are removed in vacuo and the crude product is purified on an appropriate silica gel, such as BIOSIL-A™, using an appropriate solvent system, such as a gradient of 0 to 20% methanol in either chloroform or ethyl acetate. The products are sufficiently pure for subsequent steps.

EXAMPLE 29

4-Formylphenoxyacetic acid (1) condensed with Calicheamicin N-acetyl gamma dimethyl hydrazide.
HPLC retention time: 4.4 min,
FAB MS: 1641 (M+H),
UV max at 291 and 305 nm (acetate),
$^1$H-NMR: See FIG. 2A.

PREPARATION 30

4-Formylbenzoic acid (2) condensed with Calicheamicin N-acetyl gamma dimethyl hydrazide.
HPLC retention time: 5.2 min,
FAB MS: 1611 (M+H),
UV max at 292 and 302 nm (ethanol),
$^1$H-NMR: See FIG. 23.

PREPARATION 31

Figure 26:
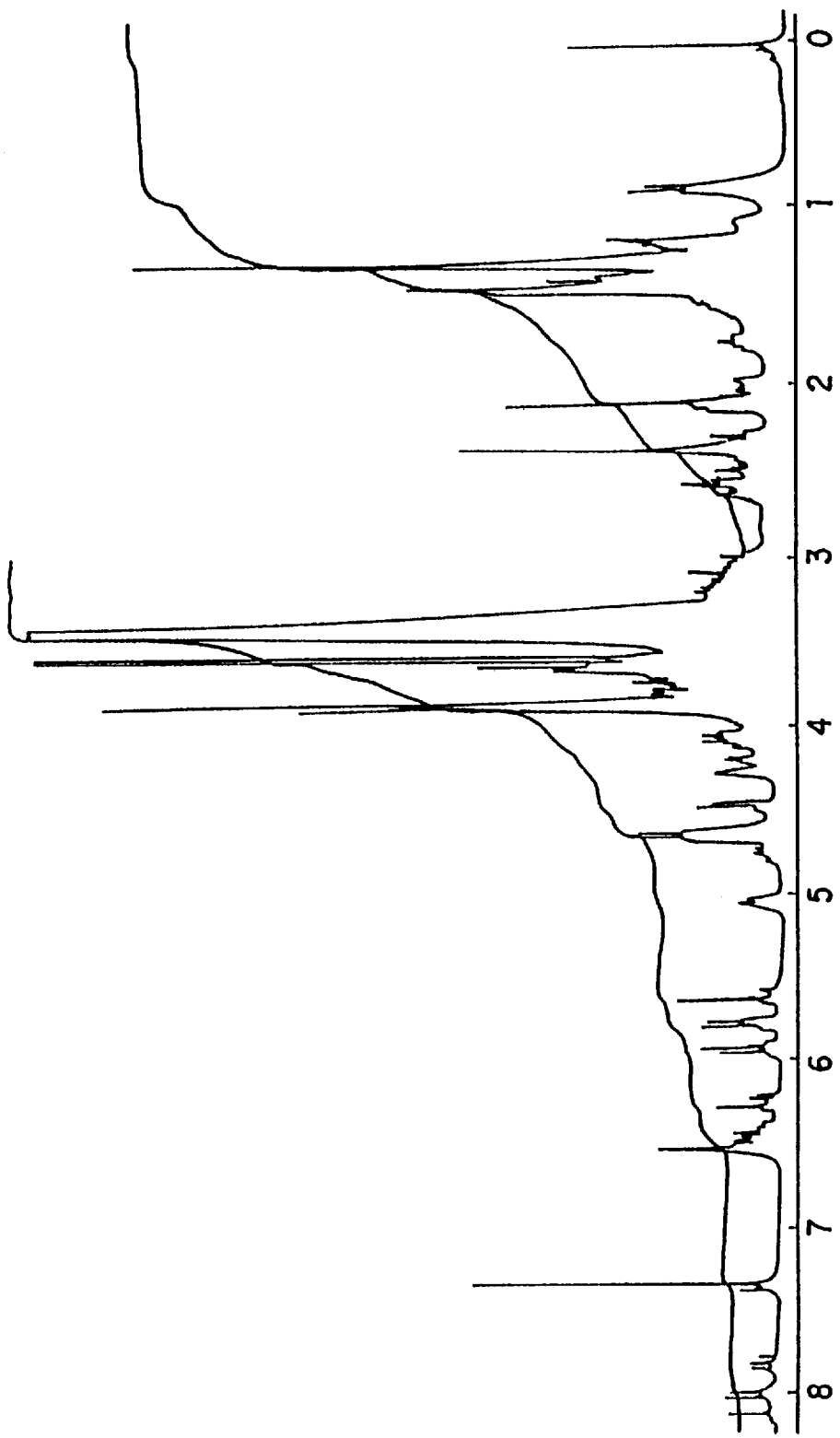
FIG. 26: The proton magnetic resonance spectrum of 4-formyl-3-methoxyphenoxyacetic acid condensed with Calicheamicin N-acetyl gamma dimethyl hydrazide.

4-Formyl-3-methoxyphenoxyacetic acid (3) condensed with Calicheamicin N-acetyl gamma dimethyl hydrazide.
HPLC retention time: 4.7 min,
FAB MS: 1671 (M+H),
UW max at 282, 291, and 325 nm (ethanol),
$^1$H-NMR: See FIG. 26.

PREPARATION 32

Figure 27:
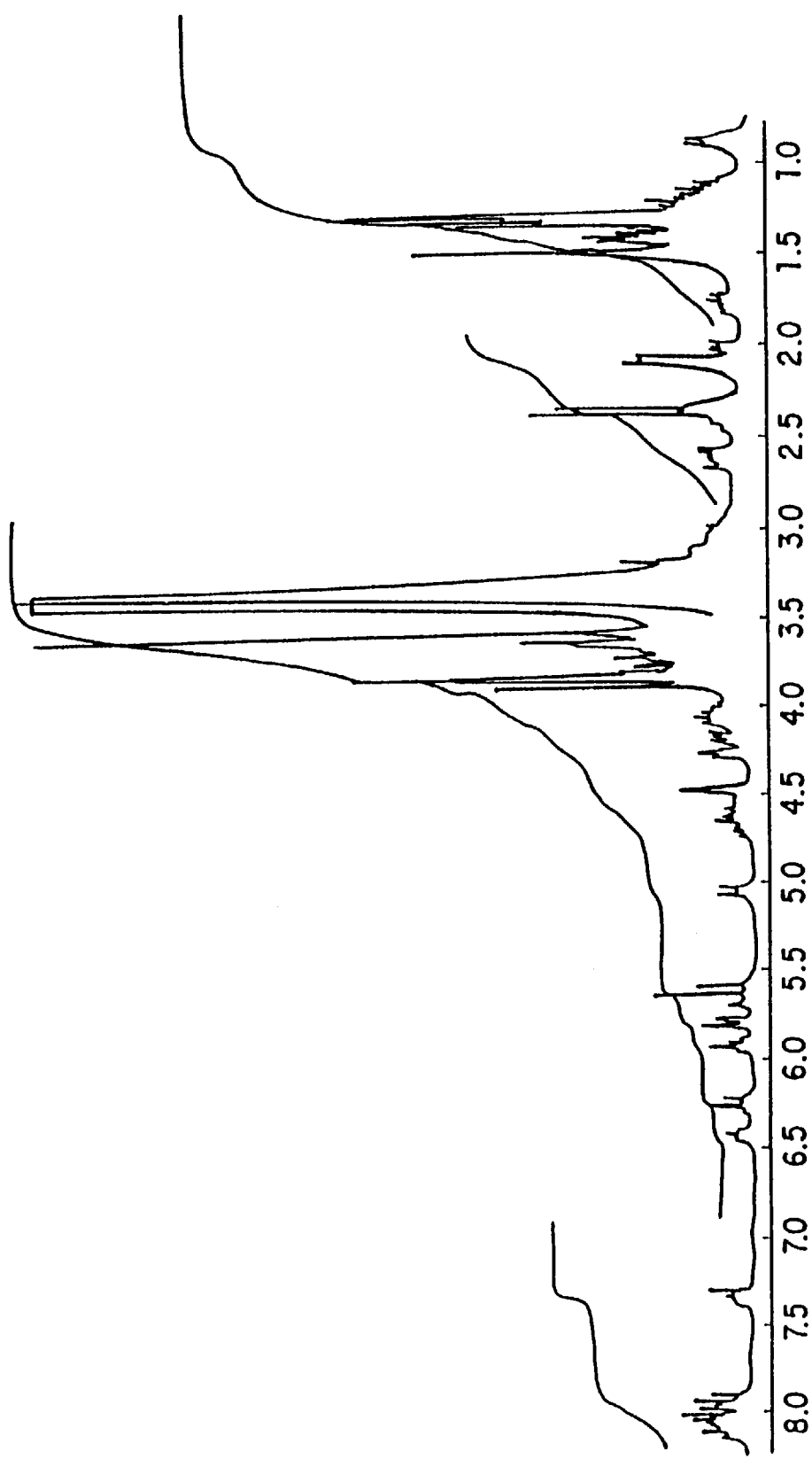
FIG. 27: The proton magnetic resonance spectrum of 6-formyl-2-naphthoic acid condensed with Calicheamicin N-acetyl gamma dimethyl hydrazide.

6-Formyl-2-naphthoic acid (4) condensed with Calicheamicin N-acetyl gamma dimethyl hydrazide.
HPLC retention time: 6.1 min,
FAB MS: 1661 (M+H),
UV max at 257, 267, 277, 313, and 321 nm (ethanol),
$^1$H-NMR: See FIG. 27.

PREPARATION 33

4-(2-Oxoethoxy)benzenepropanoic acid (5) condensed with Calicheamicin N-acetyl gamma dimethyl hydrazide.
HPLC retention time: 6.0 min,
FAB MS: 1669 (M+H),
UV—no maxima.

PREPARATION 34

3-(2-Oxoethoxy)benzoic acid (6) condensed with Calicheamicin N-acetyl gamma dimethyl hydrazide.
HPLC retention time: 5.5 min,
FAB MS: 1641 (M+H),
UV—no maxima.

PREPARATION 35

Figure 28:
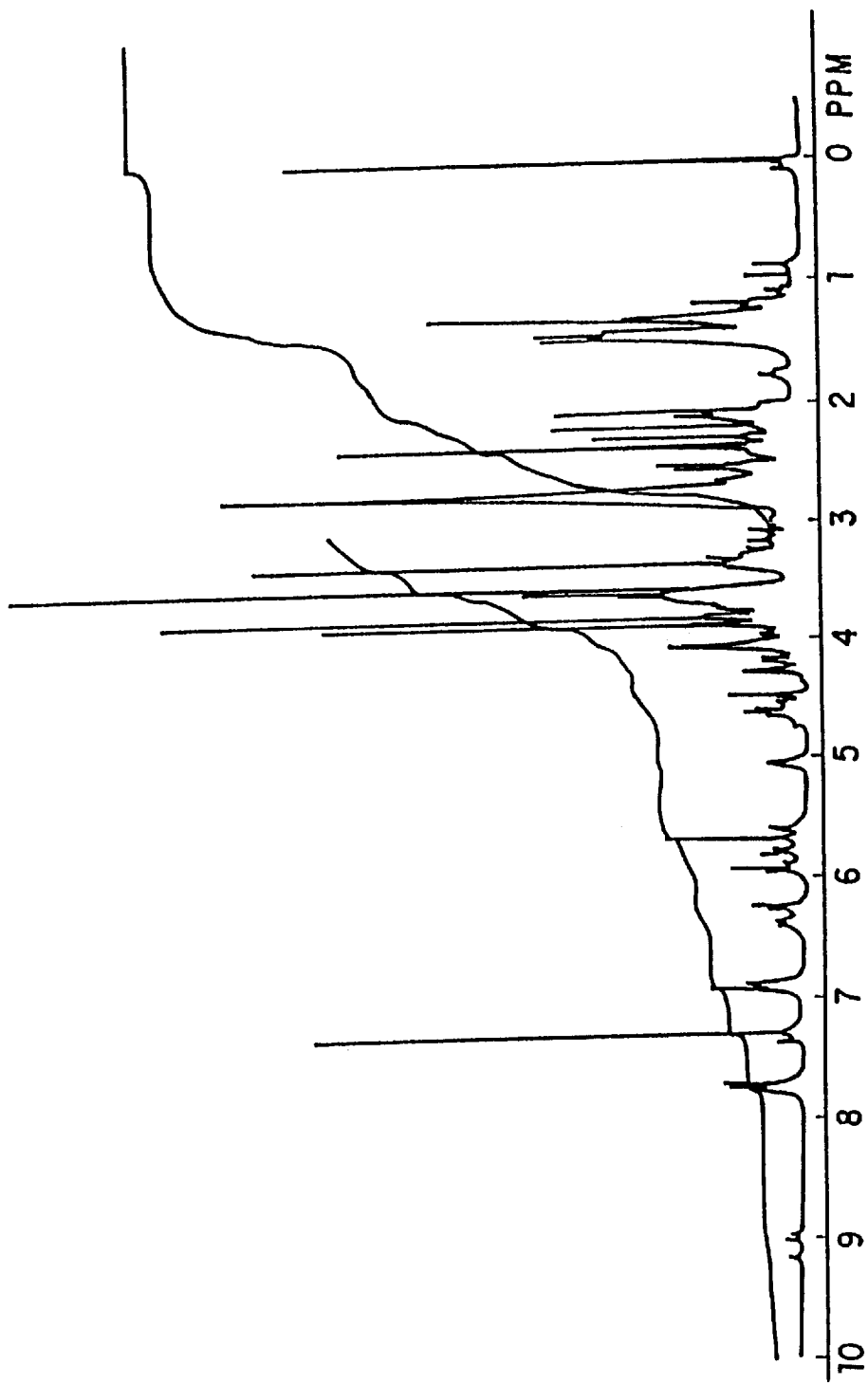
FIG. 28. The proton magnetic resonance spectrum of 4-(4-acetylphenoxy)butanoic acid condensed with Calicheamicin N-acetyl gamma dimethyl hydrazide.

4-(4-Acetylphenoxy)butanoic acid (7) condensed with Calicheamicin N-acetyl gamma dimethyl hydrazide.
HPLC retention time: 6.4 min,
FAB MS: 1683 (M+H),
UV max at 285 nm (ethanol),
$^1$H-NMR: See FIG. 28.

PREPARATION 36

4-(4-Acetylphenoxy)butanoic acid (7) condensed with calicheamicin gamma dimethyl hydrazide.
HPLC retention time: 6.2 min,
UV max at 285 nm (ethanol).

PREPARATION 37

4-(3-Formylphenoxy)butanoic acid (8) condensed with Calicheamicin N-acetyl gamma dimethyl hydrazide.
HPLC retention time: 6.3 min,
FAB MS: 1669 (M+H).

PREPARATION 38

Figure 30:
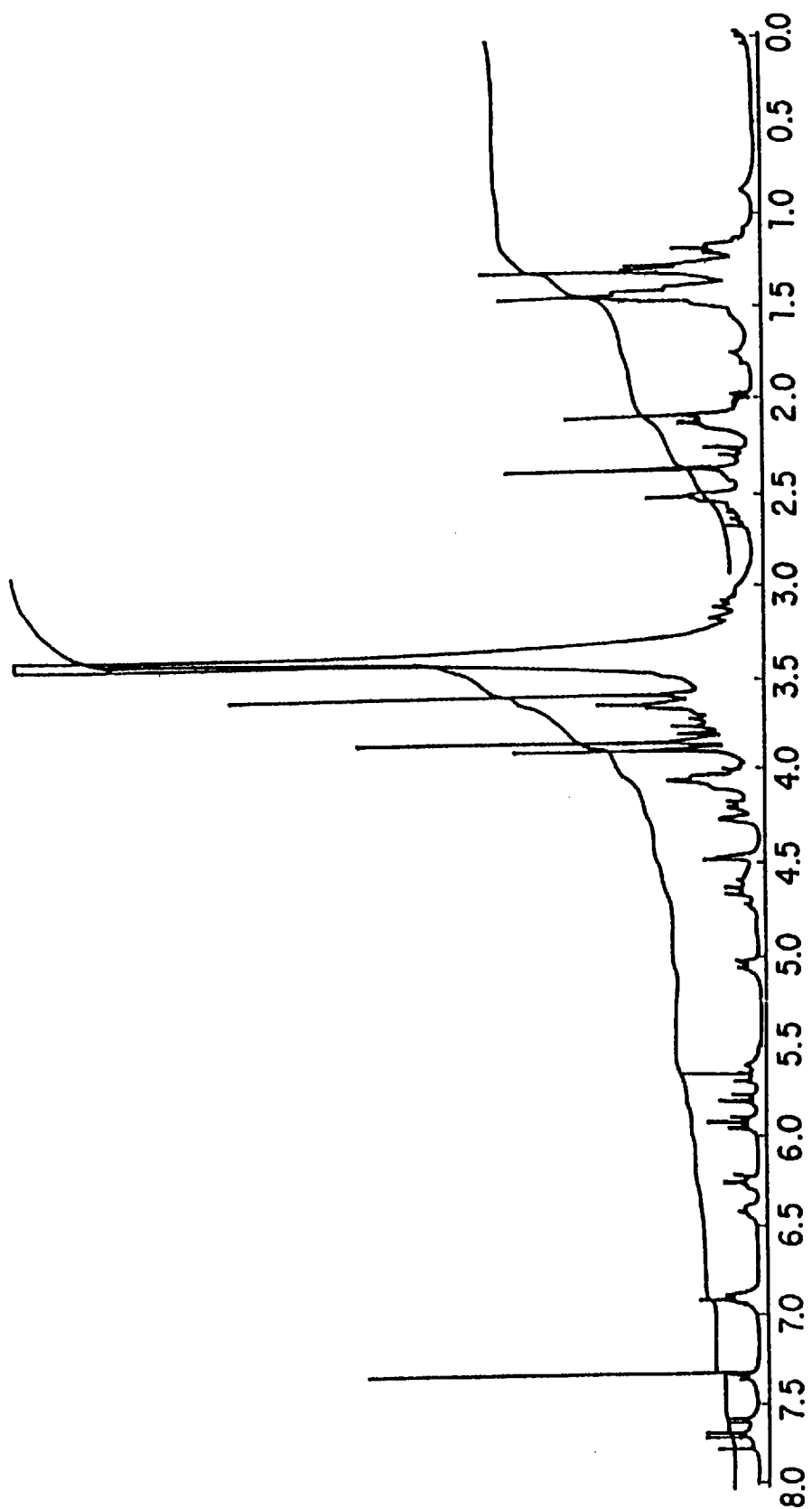
FIG. 30: The proton magnetic resonance spectrum of 4-(4-formylphenoxy)butanoic acid condensed with Calicheamicin N-acetyl gamma dimethyl hydrazide.

4-(4-Formylphenoxy)butanoic acid (9) condensed with Calicheamicin N-acetyl gamma dimethyl hydrazide.
HPLC retention time: 6.1 min,
FAB MS: 1669 (M+H),
UV max at 291 nm (ethanol),
$^1$H-NMR: See FIG. 30.

PREPARATION 39

4-(4-Acetyl-2-methylphenoxy)butanoic acid (10) condensed with Calicheamicin N-acetyl gamma dimethyl hydrazide.
HPLC retention time: 6.8 min,
FAB MS: 1697 (M+H).

EXAMPLE 40

4-(4-Formyl-2-methoxyphenoxy)butanoic acid (11) condensed with Calicheamicin N-acetyl gamma dimethyl hydrazide.
HPLC retention time: 5.5 min,
FAB MS: 1699 (M+H),
UV max at 284, 300, and 316 nm (acetonitrile).

EXAMPLE 41

4-Formylbenzenepropanoic acid (12) condensed with Calicheamicin N-acetyl gamma dimethyl hydrazide.
HPLC retention time: 5.6 min,
FAB MS: 1639 (M+H).

EXAMPLE 42

4-(2,3-Dimethoxy-5-formylphenoxy)butanoic acid (13) condensed with Calicheamicin N-acetyl gamma dimethyl hydrazide.
HPLC retention time: 5.8 min,
FAB MS: 1729 (M+H),
UV max at 302 nm (ethanol).

EXAMPLE 43

4-(4-Acetyl-2,6-dimethoxyphenoxy)butanoic acid (14) condensed with Calicheamicin N-acetyl gamma dimethyl hydrazide.

HPLC retention time: 6.0 min,
FAB MS: 1743 (M+H),
UV max at 287 nm (ethanol),.

EXAMPLE 44

4- (4-Acetyl-2-methoxyphenoxy)butanoic acid (15) condensed with Calicheamicin N-acetyl gamma dimethyl hydrazide.

HPLC retention time: 6.1 min,
FAB MS: 1713 (M+H),
UV max at 284 nm (ethanol).

EXAMPLE 45

4-[4-(3-Oxobutyl)phenoxy]butanoic acetic acid (16) condensed with Calicheamicin N-acetyl gamma dimethyl hydrazide.

HPLC retention time: 6.6 min,
FAB MS: 1611 (M+H),
UV—no maxima.

EXAMPLE 46

4-(2-Acetyl-5-methoxyphenoxy]butanoic acid (17) condensed with Calicheamicin N-acetyl gamma dimethyl hydrazide.

HPLC retention time: 6.5 min,
FAB MS: 1713 (M+H),
UV—no maxima.

EXAMPLE 47

4-[4-(3-Oxopropyl)phenoxy]butanoic acid (18) condensed with Calicheamicin N-acetyl gamma dimethyl hydrazide.

HPLC retention time: 9.8 min,
FAB MS: 1697 (M+H),
UV—no maxima.

EXAMPLE 48

4-Acetylbenzenebutanoic acid (19) condensed with Calicheamicin N-acetyl gamma dimethyl hydrazide.

HPLC retention time: 6.4 min,
FAB MS: 1667 (M+H),
UV max at 281 nm (ethanol).

EXAMPLE 49

4-[(2-Acetyl-1-naphthalenyl)oxy] butanoic acid (20) condensed with Calicheamicin N-acetyl gamma dimethyl hydrazide.

HPLC retention time: 7.8 min,
FAB MS: 1733 (M+H),
UV—no maxima.

EXAMPLE 50

4-[4-(4-Fluorobenzoyl)phenoxy]butanoic acid (21) condensed with Calicheamicin N-acetyl gamma dimethyl hydrazide.

HPLC retention time: 8.4 min,
FAB MS: 1763 (M+H),
UV max at 284 nm (ethanol).

EXAMPLE 51

4-(4-Acetylphenyl)-1-piperazinepentanoic acid (22) condensed with Calicheamicin N-acetyl gamma dimethyl hydrazide.

HPLC retention time: 5.0 min,
FAB MS: 1641 (M+H),
UV max at 322 nm (ethanol).

EXAMPLE 52

11-(4-Acetylphenoxy)undecanoic acid (23) condensed with Calicheamicin N-acetyl gamma dimethyl hydrazide.

HPLC retention time: 4.8 min (65% acetonitrileisocratic),
FAB MS: 1781 (M+H),
UV max at 286 nm (ethanol).

EXAMPLE 53

5-[(4-Acetylphenyl)amino]-5-oxopentanoic acid (24) condensed with Calicheamicin N-acetyl gamma dimethyl hydrazide.

HPLC retention time: 5.2 min,
FAB MS: 1710 (M+H),
UV max at 295 nm (ethanol).

EXAMPLE 54

4-(2-Chloro-4-formylphenoxy)butanoic acid (25) condensed with Calicheamicin N-acetyl gamma dimethyl hydrazide.

HPLC retention time: 6.5 min,
FAB MS: 1704 (M+H),
UV max at 292 nm (ethanol).

EXAMPLE 55

5-Acetyl-2-(3-carboxypropoxy)benzoic acid (26), methyl ester condensed with Calicheamicin N-acetyl gamma dimethyl hydrazide.

HPLC retention time: 6.1 min,
FAB MS: 1741 (M+H),
UV max at 285 nm (ethanol).

EXAMPLE 56

4-(4-Formyl-2-nitrophenoxy)butanoic acid (27) condensed with Calicheamicin N-acetyl gamma dimethyl hydrazide.

HPLC retention time: 6.2 min,
FAB MS: 1741 (M+H),
UV max at 294 nm (ethanol).

EXAMPLE 57

4-[2-[[(4-Acetylphenyl)amino]methyl]-6-methoxyphenoxy]butanoic acid (28) condensed with Calicheamicin N-acetyl gamma dimethyl hydrazide.

HPLC retention time: 7.7 min,
FAB MS: 1818 (M+H),
UV max at 323 nm (ethanol).

EXAMPLE 58

4-(4-Acetyl-3-fluorophenoxy)butanoic acid (30) condensed with Calicheamicin N-acetyl gamma dimethyl hydrazide.

HPLC retention time: 6.1 min,
FAB MS: 1701 (M+H),
UV max at 273 nm (ethanol).

EXAMPLE 59

4-(2-Acetylphenoxy)butanoic acid (31) condensed with Calicheamicin N-acetyl gamma dimethyl hydrazide.
HPLC retention time: 6.1 min,
FAB MS: 1683 (M+H),
W—no maxima.

EXAMPLE 60

2-Acetyl-10H-phenothiazine-10-hexanoic acid (32) condensed with Calicheamicin N-acetyl gamma dimethyl hydrazide.
HPLC retention time: 6.2 min,
FAB MS: 1833 (M+NH$_4$),
UV max at 281, strong shoulder at 356 nm (CH$_3$CN).

EXAMPLE 61

4-Acetylphenylacetic acid (33) condensed with Calicheamicin N-acetyl gamma dimethyl hydrazide.
HPLC retention time: 5.0 min,
FAB MS: 1639 (M+H),
UV max at 281 nm (acetonitrile).

SYNTHESIS OF STRUCTURES C (Scheme 1)

General Procedure

The carboxylic acid-hydrazones as obtained above are converted to the OSu esters ($Z^3$=N-succinimidyloxy) by dissolving them in an appropriate solvent such as acetonitrile or acetonitrile containing 10–20% N,N-dimethylforamide or tetrahydrofuran for better solubilization and adding ~2–5 equivalents of N-hydroxysuccinimide and ~2–10 equivalents of 1-(3-dimethylaminopropyl)-3-ethylcarbodiimide (EDCI) as the hydrochloride salt. The reaction is allowed to proceed at ambient temperature until complete as measured by HPLC or alternately by TLC, which is usually 1 to 8 hours. The solvents are then removed and the crude product is purified on an appropriate silica gel, such as BIOSIL-A™, using an appropriate solvent system, such as a gradient of 0 to 20% methanol in either chloroform or ethyl acetate. The products are then sufficiently pure for the conjugation step.

EXAMPLE 62

4-Formylphenoxyacetic acid (1) condensed with Calicheamicin N-acetyl gamma dimethyl hydrazide, N-hydroxysuccimide ester.
HPLC retention time: 6.5 min.

EXAMPLE 63

4-Formylbenzoic acid (2) condensed with Calicheamicin N-acetyl gamma dimethyl hydrazide, N-hydroxysuccimide ester.
HPLC retention time: 6.6 min,
FAB MS: 1708 (M+H),
UV max at 310 nm (acetonitrile).

EXAMPLE 64

4-Formyl-3-methoxyphenoxyacetic acid (3) condensed with Calicheamicin N-acetyl gamma dimethyl hydrazide, N-hydroxysuccimide ester.
HPLC retention time: 7.0 min.
FAB MS: 1768 (M+H),
UV max at 279, 288, and 320 nm (acetonitrile).

EXAMPLE 65

6-Formyl-2-naphthoic acid (4) condensed with Calicheamicin N-acetyl gamma dimethyl hydrazide, N-hydroxysuccimide ester.
HPLC retention time: 7.4 min,
FAB MS: 1758 (M+H),
UV max at 272 and 323 nm (ethanol).

EXAMPLE 66

4-(2-Oxoethoxy)benzenepropanoic acid (5) condensed with Calicheamicin N-acetyl gamma dimethyl hydrazide, N-hydroxysuccimide ester.
HPLC retention time: 7.1 min.
FAB MS: 1766 (M+H),
W—no maxima.

EXAMPLE 67

3-(2-Oxoethoxy)benzoic acid (6) condensed with Calicheamicin N-acetyl gamma dimethyl hydrazide, N-hydroxysuccimide ester.
HPLC retention time: 7.7 min,
UV—no maxima.

Figure 29:
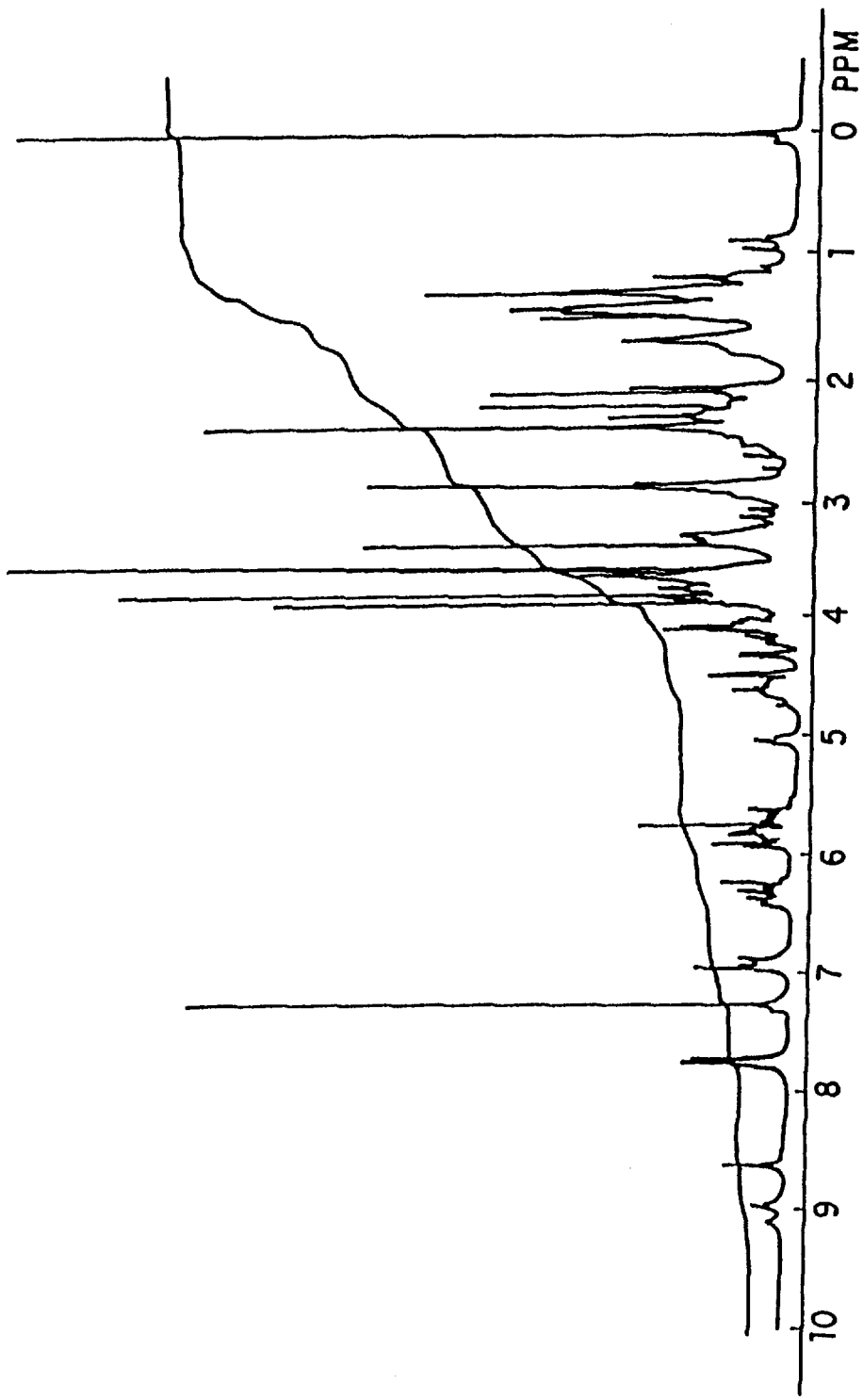
FIG. 29: The proton magnetic resonance spectrum of 4-(4-acetylphenoxy)butanoic acid condensed with Calicheamicin N-acetyl gamma dimethyl hydrazide, N-hydroxysuccinimide ester.

EXAMPLE 68A 4-(4-Acetylphenoxy)butanoic acid (7) condensed with Calicheamicin N-acetyl gamma dimethyl hydrazide, N-hydroxysuccimide ester.
HPLC retention time: 7.5 min,
FAB MS: 1780 (M+H),
UV max at 283 nm (acetonitrile),
$^1$H-NMR: See FIG. 29.

EXAMPLE 68B 4-(4-Acetylphenoxy)butanoic acid (7) condensed with Calicheamicin N-acetyl gamma dimethyl hydrazide, (1-hydroxy-2,5-dioxo-3-pyrrolidinesulfonic acid, monosodium salt) ester (i.e. ester with "sulfonato-N-hydroxysuccimide").
HPLC retention time: 5.2 min,
UV max at 278 nm (ethanol).

EXAMPLE 69

4-(4-Acetylphenoxy)butanoic acid (7) condensed with calicheamicin gamma dimethyl hydrazide, N-hydroxysuccimide ester.
HPLC retention time: 7.6 min,
UV max at 283 nm (acetonitrile).

EXAMPLE 70

4-(3-Formylphenoxy)butanoic acid (8) condensed with Calicheamicin N-acetyl gamma dimethyl hydrazide, N-hydroxysuccimide ester.
HPLC retention time: 7.4 min,
FAB MS: 1766 (M+H),
UV max at 283 nm (acetonitrile).

EXAMPLE 71

4-(4-Formylphenoxy)butanoic acid (9) condensed with Calicheamicin N-acetyl gamma dimethyl hydrazide, N-hydroxysuccimide ester.

HPLC retention time: 7.0 min,
FAB MS: 1766 (M+H),
UV max at 289 nm (acetonitrile).

EXAMPLE 72

4-(4-Acetyl-2-methylphenoxy)butanoic acid (10) condensed with Calicheamicin N-acetyl gamma dimethyl hydrazide, N-hydroxysuccimide ester.

HPLC retention time: 8.2 min,
FAB MS: 1794 (M+H).

EXAMPLE 73

4-(4-Formyl-2-methoxyphenoxy)butanoic acid (11) condensed with Calicheamicin N-acetyl gamma dimethyl hydrazide, N-hydroxysuccimide ester.

HPLC retention time: 6.6 min,
FAB MS: 1796 (M+H).

EXAMPLE 74

4-Formylbenzenepropanoic acid (12) condensed with Calicheamicin N-acetyl gamma dimethyl hydrazide, N-hydroxysuccimide ester.

HPLC retention time: 6.7 min,
FAB MS: 1736 (M+H).

EXAMPLE 75

4-(2,3-Dimethoxy-5-formylphenoxy)butanoic acid (13) condensed with Calicheamicin N-acetyl gamma dimethyl hydrazide, N-hydroxysuccimide ester.

HPLC retention time: 6.7 min,
FAB MS: 1826 (M+H),
UV max at 298 nm (ethanol).

EXAMPLE 76

4-(4-Acetyl-2,6-dimethoxyphenoxy)butanoic acid (14) condensed with Calicheamicin N-acetyl gamma dimethyl hydrazide, N-hydroxysuccimide ester.

HPLC retention time: 7.7 min,
FAB MS: 1840 (M+H),
UV max at 286 nm (acetonitrile).

EXAMPLE 77

4-(4-Acetyl-2-methoxyphenoxy)butanoic acid (1S) condensed with Calicheamicin N-acetyl gamma dimethyl hydrazide, N-hydroxysuccimide ester.

HPLC retention time: 7.2 min,
FAB MS: 1810 (M+H),
UV max at 284 nm (acetonitrile).

EXAMPLE 78

4-[4-(3-Oxobutyl)phenoxy]butanoic acid (16) condensed with Calicheamicin N-acetyl gamma dimethyl hydrazide, N-hydroxysuccimide ester.

HPLC retention time: 7.9 min,
FAB MS: 1808 (M+H),
UV—no maxima.

EXAMPLE 79

4-[2-Acetyl-5-methoxyphenoxy]butanoic acid (17) condensed with Calicheamicin N-acetyl gamma dimethyl hydrazide, N-hydroxysuccimide ester.

HPLC retention time: 7.4 min,
FAB MS: 1810 (M+H),
UV—no maxima.

EXAMPLE 80

4-[4-(3-Oxopropyl)phenoxy]butanoic acid (18) condensed with Calicheamicin N-acetyl gamma dimethyl hydrazide, N-hydroxysuccimide ester.

HPLC retention time: 13.1 min,
FAB MS: 1794 (M+H),
UV—no maxima.

EXAMPLE 81

4-Acetylbenzenebutanoic acid (19) condensed with Calicheamicin N-acetyl gamma dimethyl hydrazide, N-hydroxysuccimide ester.

HPLC retention time: 7.7 min.

EXAMPLE 82

4-[(2-Acetyl-1-naphthalenyl)oxy] butanoic acid (20) condensed with Calicheamicin N-acetyl gamma dimethyl hydrazide, N-hydroxysuccimide ester.

HPLC retention time: 9.4 min,
FAB MS: 1830 (M+H),
UV—no maxima.

EXAMPLE 83

4-[4-(4-Fluorobenzoyl)phenoxy]butanoic acid (21) condensed with Calicheamicin N-acetyl gamma dimethyl hydrazide, N-hydroxysuccimide ester.

HPLC retention time: 9.3 min,
FAB MS: 1860 (M+H),
UV max at 284 nm (ethanol).

EXAMPLE 84

4-(4-Acetylphenyl)-1-piperazinepentanoic acid (22) condensed with Calicheamicin N-acetyl gamma dimethyl hydrazide, N-hydroxysuccimide ester.

HPLC retention time: 6.3 min,
FAB MS: 1863 (M+H),
UV max at 306 nm (1:1 acetonitrile/chloroform).

EXAMPLE 85

11-(4-Acetylphenoxy)undecanoic acid (23) condensed with Calicheamicin N-acetyl gamma dimethyl hydrazide, N-hydroxysuccimide ester.

HPLC retention time: 15.5 min,
FAB MS: 1878 (M+H),
UV max at 284 nm (ethanol).

EXAMPLE 86

5-[(4-Acetylphenyl)amino]-5-oxopentanoic acid (24) condensed with Calicheamicin N-acetyl gamma dimethyl hydrazide, N-hydroxysuccimide ester.

HPLC retention time: 6.2 min,
FAB MS: 1807 (M+H),
UV max at 292 nm (acetonitrile).

EXAMPLE 87

4-(2–Chloro-4-formylphenoxy)butanoic acid (25) condensed with Calicheamicin N-acetyl gamma dimethyl hydrazide, N-hydroxysuccimide ester.

HPLC retention time: 7.5 min,
FAB MS: 1800 (M+H),
UV max at 290 nm (acetonitrile).

EXAMPLE 88

5-Acetyl-2-(3-carboxypropoxy)benzoic acid (26), methyl ester condensed with Calicheamicin N-acetyl gamma dimethyl hydrazide, N-hydroxysuccimide ester.

HPLC retention time: 7.2 min,
FAB MS: 1838 (M+H),
UV max at 284 nm (acetonitrile).

EXAMPLE 89

4-(4-Formyl-2-nitrophenoxy)butanoic acid (27) condensed with Calicheamicin N-acetyl gamma dimethyl hydrazide, N-hydroxysuccimide ester.

HPLC retention time: 7.1 min,
FAB MS: 1811 (M+H),
UV max at 293 nm (ethanol).

EXAMPLE 90

4-[2-[[(4-Acetylphenyl)amino]methyl]-6-methoxyphenoxy]butanoic acid (28) condensed with Calicheamicin N-acetyl gamma dimethyl hydrazide, N-hydroxysuccimide ester.

HPLC retention time: 9.2 min,
FAB MS: 1916 (M+H),
UV max at 309 nm (acetonitrile).

EXAMPLE 91

4-(4-Acetyl-3-fluorophenoxy)butanoic acid (30) condensed with Calicheamicin N-acetyl gamma dimethyl hydrazide, N-hydroxysuccimide ester.

HPLC retention time: 8.2 min,
FAB MS: 1798 (M+H),
UV max at 270 nm (ethanol).

EXAMPLE 92

4-(2-Acetylphenoxy)butanoic acid (31) condensed with Calicheamicin N-acetyl gamma dimethyl hydrazide, N-hydroxysuccimide ester.

HPLC retention time: 8.1 min,
FAB MS: 1780 (M+H),
UV—no maxima.

EXAMPLE 93

2-Acetyl-10H-phenothiazine-10-hexanoic acid (32) condensed with Calicheamicin N-acetyl gamma dimethyl hydrazide, N-hydroxysuccimide ester.

HPLC retention time: 8.3 min,
FAB MS: 1930 (M+NH$_4$),
UV max at 281 nm (acetonitrile).

EXAMPLE 94

4-Acetylphenylacetic acid (33) condensed with Calicheamicin N-acetyl gamma dimethyl hydrazide, N-hydroxysuccimide ester.

HPLC retention time: 7.2 min,
FAB MS: 1736 (M+H),
UV max at 280 nm (acetonitrile).

SYNTHESIS OF STRUCTURES D (Method A-Scheme 1)

General Procedure

The activated ester from above is dissolved in an appropriate organic solvent, such as dimethylformamide, and added to a solution of antibody at ~1–15 mg/mL in an appropriate buffer, such as pH 7.4 phosphate (50 mM, 100 mM salt) such that the concentration of organic co-solvent is ~10–30% and ~2–10 equivalents of active ester are used per mole of antibody. The conjugation reaction is allowed to proceed at ambient temperature for ~4–24 hours. The solution is concentrated by use of a semipermeable membrane, if necessary, and purified by standard size-exclusion chromatography, such as with SEPHACRYL S™-200 gel. The monomer fractions are pooled and the loading of drug on the antibody is estimated by UV-VIS absorbance at 280 nm for antibody and 333 nm or other appropriate wavelength for the calicheamicin hydrazones.

SYNTHESIS OF STRUCTURES E (Scheme 2)

General Procedure

The carboxylic acids of the spacers are activated as the OSu esters ($Z^3$=N-succinimidyloxy) by dissolving them in an appropriate solvent such as tetrahydrofuran containing 10–20% dimethylformamide and adding ~2–3 equivalents of N-hydroxysuccinimide and ~2–5 equivalents of 1-(3-dimethylaminopropyl)-3-ethylcarbodiimide (EDCI) as the hydrochloride salt. The reaction is allowed to proceed at ambient temperature until complete as assessed by TLC, which is usually 1 to 8 hours. The solvents are then removed and the crude product is purified on an appropriate silica gel, such as BIOSIL-A™, using an appropriate solvent system, such as a gradient of 0 to 5% methanol in chloroform. The products are generally purified further by recrystallization from a mixture of ethyl acetate-hexanes or other appropriate solvents.

The following preparations were made by the above procedure:

(SuOH=N-hydroxysuccinimide)

PREPARATION 95

4-Formylphenoxy acetic acid (1), N-hydroxysuccinimide ester.

CI MS: 278 (MH$^+$), NMR (CDCl$_3$+D$_6$-DMSO): 9.9 ppm (1H, s, CH=O), 7.9 and 7.1 (2H each, d, ArH), 5.2 (2H, s, OCH$_2$), 2.9 (4H, s, CH$_2$CH$_2$).

PREPARATION 96

4-Formyl-3-methoxyphenoxy acetic acid (3), N-hydroxysuccinimide ester.

CI MS: 308 (MH$^+$), NMR (CDCl$_3$): 10.3 ppm (1H, s, CH=O), 7.8 (1H, d, ArH), 6.6 (1H, dt, ArH), 6.55 (1H, d, ArH), 5.1 (2H, s, OCH$_2$), 3.95, (3H, s, OCH$_3$), 2.9 (4H, s, CH$_2$CH$_2$).

PREPARATION 97

4-(4-Acetylphenoxy)butanoic acid (7), N-hydroxysuccinimide ester.

CI MS: 320 (MH$^+$), NMR (CDCl$_3$): 7.9 and 7.0 (2H each, d, ArH), 4.2 (2H, s, OCH$_2$), 2.9 (6H, m, CH$_2$CH$_2$+O=CCH$_2$), 2.6 (3H, s, O=CCH$_3$), 2.3 (2H, m, CH$_2$).

SYNTHESIS OF STRUCTURES F (Scheme 2)

General Procedure

The activated ester from above is dissolved in an appropriate organic solvent, such as N,N-dimethylformamide, and added to a solution of antibody at ~1–15 mg/mL in an appropriate buffer, such as pH 7.4 phosphate (50 mM, 100 mM salt) such that the concentration of organic co-solvent is ~10–25% and ~2–20 equivalents of active ester are used per mole of antibody. The conjugation reaction is allowed to proceed at ambient temperature for ~4–24 hours. The buffer is exchanged and the organic co-solvents and by-products are removed by use of a desalting column such as a PD-10 using pH 5.5 acetate buffer (25 mM acetate, 100 mM NaCd). The solution is concentrated by use of a semipermeable membrane, if necessary, and the product is used without further purification for the following step. The number of carbonyl groups incorporated per antibody is usually about half the number of equivalents of OSu ester used and can be further quantified by use of p-nitrophenyl hydrazine or other comparable method, if desired.

SYNTHESIS OF STRUCTURES D (Method B-Scheme 2)

General Procedure

The drug hydrazide derivative is dissolved in an appropriate organic solvent, such as N,N-dimethylformamide, and added to a solution of antibody-linker conjugate (structure F) from the previous step at ~1–15 mg/mL in an appropriate buffer, such as pH acetate (25 mM, 100 mM salt) such that the concentration of organic co-solvent is ~10–15% and ~2–15 equivalents of hydrazide are used per mole of antibody. The conjugation reaction is allowed to proceed at ambient temperature for ~4–24 hours. The buffer is exchanged and the organic co-solvents and by-products are removed by use of a desalting column such as a PD-10 using pH 7.4 buffer (50 mM phosphate, 100 mM NaCl). The solution is concentrated by use of a semipermeable membrane, if necessary, and purified by standard size-exclusion chromatography, such as with SEPHACRYL™ S-200 gel. The monomer fractions are pooled and the loading of drug on the antibody is estimated by UV-VIS absorbence at 280 nm for antibody and 333 nm or other appropriate wavelength for the calicheamicin hydrazones.

EXAMPLE 98 (METHOD A AND B)

Conjugate of 4-formylphenoxyacetic acid (1) condensed with Calicheamicin N-acetyl gamma dimethyl hydrazide and h-P67.6.

Loading: 1.0 M/M, Rel. Affinity: 0.65,

In vitro $IC_{50}$: 0.23 ng/mL, Spec. Index: 1,600,

In vivo: 29% T/C (2 µg×3 doses—5/5 alive-28d),

Ex vivo: 95% inhibition.

EXAMPLE 99 (METHOD A AND B)

Conjugate of 4-formylphenoxyacetic acid (1) condensed with Calicheamicin N-acetyl gamma dimethyl hydrazide and m-P67.6.

Loading: 1.5 M/M, Rel. Affinity: 0.77,

In vitro $IC_{50}$: 0.068 ng/mL, Spec. Index: 3,600,

Ex vivo: 90% inhibition.

EXAMPLE 100 (METHOD A)

Conjugate of 4-formylphenoxyacetic acid (1) condensed with Calicheamicin N-acetyl gamma dimethyl hydrazide and m-CT-M-01.

Loading: 2.0 M/M, Rel. Affinity: 0.84,

In vitro $IC_{50}$: 1.5 ng/mL, Spec. Index: 59.

EXAMPLE 101 (METHOD A)

Conjugate of 4-formylbenzoic acid (2) condensed with Calicheamicin N-acetyl gamma dimethyl hydrazide and h-P67.6.

Loading: 4.8 M/M, Rel. Affinity: 0.99,

In vitro $IC_{50}$: 4.8 ng/mL, Spec. Index: >125,

Ex vivo: 63% inhibition.

EXAMPLE 102 (METHOD A)

Conjugate of 4-formylbenzoic acid (2) condensed with Calicheamicin N-acetyl gamma dimethyl hydrazide and m-P67.6.

Loading: 4.0 M/M, Rel. Affinity: 1.05,

In vitro $IC_{50}$: 4.0 ng/mL, Spec. Index: >125.

EXAMPLE 103 (METHOD A)

Conjugate of 4-formylbenzoic acid (2) condensed with Calicheamicin N-acetyl gamma dimethyl hydrazide and m-CT-M-01.

Loading: 2.3 M/M, Rel. Affinity: 0.90,

In vitro $IC_{50}$: 5.6 ng/mL, Spec. Index: 32.

EXAMPLE 104 (METHOD A AND B)

Conjugate of 4-formyl-3-methoxyphenoxyacetic acid (3) condensed with Calicheamicin N-acetyl gamma dimethyl hydrazide and h-P67.6.

Loading: 0.8 M/M, Rel. Affinity: 0.81,

In vitro $IC_{50}$: 0.30 ng/mL, Spec. Index: 375.

EXAMPLE 105 (METHOD A AND B)

Conjugate of 4-formyl-3-methoxyphenoxyacetic acid (3) condensed with Calicheamicin N-acetyl gamma dimethyl hydrazide and m-P67.6.

Loading: 0.9 M/M, Rel. Affinity: 0.76,

In vitro $IC_{50}$: 0.12 ng/mL, Spec. Index: 1,200,

Ex vivo: 90% inhibition.

EXAMPLE 106 (METHOD A)

Conjugate of 4-formyl-3-methoxyphenoxyacetic acid (3) condensed with Calicheamicin N-acetyl gamma dimethyl hydrazide and m-CT-M-01.

Loading: 2.1 M/M, Rel. Affinity: 0.88,

In vitro $IC_{50}$: 5.6 ng/mL, Spec. Index: 12.

EXAMPLE 107 (METHOD A)

Conjugate of 6-formyl-2-naphthoic acid (4) condensed with Calicheamicin N-acetyl gamma dimethyl hydrazide and m-P67.6.

Loading: 2.0 M/M, Rel. Affinity: 0.73,

In vitro $IC_{50}$: 0.047 ng/mL, Spec. Index: 675.

EXAMPLE 108 (METHOD A)

Conjugate of 4-(2-oxoethoxy)benzenepropanoic acid (5) condensed with Calicheamicin N-acetyl gamma dimethyl hydrazide and h-P67.6.

Loading: 1.1 M/M, Rel. Affinity: 1.09,

In vitro $IC_{50}$: 2.22 ng/mL, Spec. Index: 125.

EXAMPLE 109 (METHOD A)

Conjugate of 4-(2-oxoethoxy)benzenepropanoic acid (5) condensed with Calicheamicin N-acetyl gamma dimethyl hydrazide and m-P67.6.

Loading: 0.6 M/M, Rel. Affinity: 1.11,

In vitro $IC_{50}$: 0.45 ng/mL, Spec. Index: 200,

Ex vivo: 71% inhibition.

EXAMPLE 110 (METHOD A)

Conjugate of 3-(2-oxoethoxy)benzoic acid (j) condensed with Calicheamicin N-acetyl gamma dimethyl hydrazide and h-P67.6.

Loading: 1.3 M/M, Rel. Affinity: 1.19,
In vitro $IC_{50}$: 0.69 ng/mL, Spec. Index: 100.

EXAMPLE 111 (METHOD A)

Conjugate of 3-(2-oxoethoxy)benzoic acid (6) condensed with Calicheamicin N-acetyl gamma dimethyl hydrazide and m-P67.6.

Loading: 0.8 M/M, Rel. Affinity: 1.91,
In vitro $IC_{50}$: 0.32 ng/mL, Spec. Index: 175.

EXAMPLE 112 (METHOD A)

Conjugate of 4-(4-acetylphenoxy)butanoic acid (7) condensed with Calicheamicin N-acetyl gamma dimethyl hydrazide and h-P67.6.

Loading: 2.7 M/M, Rel. Affinity: 0.75,
In vitro $IC_{50}$: 0.098 ng/mL, Spec. Index: 6,400,
In vivo: 0% T/C (1 μg×3 doses, 5/5 alive-28d),
  0% T/C (3 μg×3 doses, 5/5 alive-28d),
  0% T/C (6 μg×3 doses, 5/5 alive-28d),
Ex vivo: 96% inhibition.

EXAMPLE 113 (METHOD A)

Conjugate of 4-(4-acetylphenoxy)butanoic acid (7) condensed with calicheamicin gamma dimethyl hydrazide and h-P67.6.

Loading: 3.2 M/M, Rel. Affinity: 0.78,
In vitro $IC_{50}$: 0.001 ng/mL, Spec. Index: 10,000

EXAMPLE 114 (METHOD A OR B)

Conjugate of 4-(4-acetylphenoxy)butanoic acid (7) condensed with Calicheamicin N-acetyl gamma dimethyl hydrazide and m-P67.6.

Loading: 1.7 M/M, Rel. Affinity: 0.96,
In vitro $IC_{50}$: 0.017 ng/mL, Spec. Index: 29,500,
In vivo: 22% T/C (0.5 μg×3 doses, 5/5 alive-28d),
  0% T/C (1 μg×3 doses, 5/5 alive-28d),
  1% T/C (3 μg×3 doses, 5/5 alive-28d),
  0% T/C (6 μg×3 doses, 2/5 alive-28d),
Ex vivo: 98% inhibition.

EXAMPLE 115 (METHOD A)

Conjugate of 4-(4-acetylphenoxy)butanoic acid (7) condensed with Calicheamicin N-acetyl gamma dimethyl hydrazide and h-CT-M-01.

Loading: 3.4 M/M, Rel. Affinity: not determined,
In vitro $IC_{50}$: 0.048 ng/mL, Spec. Index: 6,200.

EXAMPLE 116 (METHOD A)

Conjugate of 4-(4-acetylphenoxy)butanoic acid (7) condensed with calicheamicin N-acetyl gamma dimethyl hydrazide and m-A33.

Loading: 1.1 M/M, Rel. Affinity: 0.68,
In vitro $IC_{50}$: 3.32 ng/mL, Spec. Index: 0.72.
In vivo: 4% T/C (3 μg×3 doses, 5/5 alive-28d),
  5% T/C (6 μg×3 doses, 5/5 alive-28d).

EXAMPLE 117 (METHOD A)

Conjugate of 4-(4-acetylphenoxy)butanoic acid (7) condensed with calicheamicin N-acetyl gamma dimethyl hydrazide and h-A33.

Loading: 1.8 M/M, Rel. Affinity: 1.13,
In vitro $IC_{50}$: 4.03 ng/mL, Spec. Index: 0.96.

EXAMPLE 118 (METHOD A)

Conjugate of 4-(4-acetylphenoxy)butanoic acid (7) condensed with calicheamicin gamma dimethyl hydrazide and h-A33.

Loading: 2.8 M/M, Rel. Affinity: 0.91,
In vitro $IC_{50}$: 3.55 ng/mL, Spec. Index: 2.6.

EXAMPLE 119 (METHOD A)

Conjugate of 4-(4-acetylphenoxy)butanoic acid (7) condensed with calicheamicin N-acetyl gamma dimethyl hydrazide and anti-Tac.

Loading: 2.1 M/M, Rel. Affinity: not determined,
In vitro $IC_{50}$: 0.004 ng/mL, Spec. Index: 250,
Ex vivo: $IC_{50}$: 1.0 ng/mL, Spec. Index: 100.

EXAMPLE 120 (METHOD A)

Conjugate of 4-(3-formylphenoxy)butanoic acid (8) condensed with Calicheamicin N-acetyl gamma dimethyl hydrazide and m-P67.6.

Loading: 1.7 M/M, Rel. Affinity: 1.00,
In vitro $IC_{50}$: 0.38 ng/mL, Spec. Index: 1,700.

EXAMPLE 121 (METHOD A)

Conjugate of 4-(4-formylphenoxy)butanoic acid (9) condensed with Calicheamicin N-acetyl gamma dimethyl hydrazide and h-P67.6.

Loading: 2.8 M/M, Rel. Affinity: 0.56,
In vitro $IC_{50}$: 0.52 ng/mL, Spec. Index: 2,900,
In vivo: 12% T/C (1 μg×3 doses, 5/5 alive-28d),
  9% T/C (3 μg×3 doses, 5/5 alive-28d),
  3% T/C (6 μg×3 doses, 4/5 alive-28d),
Ex vivo: 98% inhibition.

EXAMPLE 122 (METHOD A)

Conjugate of 4-(4-formylphenoxy)butanoic acid (9) condensed with Calicheamicin N-acetyl gamma dimethyl hydrazide and m-P67.6.

Loading: 1.8 M/M, Rel. Affinity: 0.70,
In vitro $IC_{50}$: 0.087 ng/mL, Spec. Index: 11,000,
In vivo: 17% T/C (0.5 μg×3 doses, 5/5 alive-28d),
  23% T/C (1 μg×3 doses, 5/5 alive-28d),
  9% T/C (3 μg×3 doses, 5/5 alive-28d),
  0% T/C (6 μg×3 doses, 5/5 alive-28d).

EXAMPLE 123 (METHOD A)

Conjugate of 4-(4-acetyl-2-methylphenoxy)butanoic acid (10) condensed with Calicheamicin N-acetyl gamma dimethyl hydrazide and h-P67.6.

Loading: 3.5 M/M, Rel. Affinity: 1.16,
In vitro $IC_{50}$: 0.45 ng/mL, Spec. Index: 2,900.

EXAMPLE 124 (METHOD A)

Conjugate of 4-(4-acetyl-2-methylphenoxy)butanoic acid (10) condensed with Calicheamicin N-acetyl gamma dimethyl hydrazide and m-P67.6.

Loading: 1.6 M/M, Rel. Affinity: 1.07,
In vitro $IC_{50}$: 0.041 ng/mL, Spec. Index: 5,100.

EXAMPLE 125 (METHOD A)

Conjugate of 4-(4-formyl-2-methoxyphenoxy)butanoic acid (11) condensed with Calicheamicin N-acetyl gamma dimethyl hydrazide and h-P67.6.

Loading: 2.6 M/M, Rel. Affinity: 0.73,
In vitro $IC_{50}$: 3.8 ng/mL, Spec. Index: 575.

EXAMPLE 126 (METHOD A)

Conjugate of 4-(4-formyl-2-methoxyphenoxy)butanoic acid (11) condensed with Calicheamicin N-acetyl gamma dimethyl hydrazide and m-P67.6.

Loading: 1.9 M/M, Rel. Affinity: 0.22,
In vitro $IC_{50}$: 0.13 ng/mL, Spec. Index: 1,800.

EXAMPLE 127 (METHOD A)

Conjugate of 4-formylbenzenepropanoic acid (12) condensed with Calicheamicin N-acetyl gamma dimethyl hydrazide and h-P67.6.

Loading: 2.5 M/M, Rel. Affinity: 0.73,
In vitro $IC_{50}$: 1.0 ng/mL, Spec. Index: 950.

EXAMPLE 128 (METHOD A)

Conjugate of 4-formylbenzenepropanoic acid (12) condensed with Calicheamicin N-acetyl gamma dimethyl hydrazide and m-P67.6.

Loading: 1.6 M/M, Rel. Affinity: 0.73,
In vitro $IC_{50}$: 0.12 ng/mL, Spec. Index: 2,000.

EXAMPLE 129 (METHOD A)

Conjugate of 4-(2,3-dimethoxy-5-formylphenoxy)butanoic acid (13) condensed with Calicheamicin N-acetyl gamma dimethyl hydrazide and h-P67.6.

Loading: 1.0 M/M, Rel. Affinity: 1.16,
In vitro $IC_{50}$: 1.1 ng/mL, Spec. Index: >375.

EXAMPLE 130 (METHOD A)

Conjugate of 4-(2,3-Dimethoxy-5-formylphenoxy)butanoic acid (13) condensed with Calicheamicin N-acetyl gamma dimethyl hydrazide and m-P67.6.

Loading: 1.8 M/M, Rel. Affinity: 1.08,
In vitro $IC_{50}$: 0.062 ng/mL, Spec. Index: >9,800.

EXAMPLE 131 (METHOD A)

Conjugate of 4-(4-acetyl-2,6-dimethoxyphenoxy)butanoic acid (14) condensed with Calicheamicin N-acetyl gamma dimethyl hydrazide and h-P67.6.

Loading: 2.6 M/M, Rel. Affinity: 1.07,
In vitro $IC_{50}$: 0.24 ng/mL, Spec. Index: >1,700.

EXAMPLE 132 (METHOD A)

Conjugate of 4-(4-acetyl-2,6-dimethoxyphenoxy)butanoic acid (14) condensed with Calicheamicin N-acetyl gamma dimethyl hydrazide and m-P67.6.

Loading: 1.7 M/M, Rel. Affinity: 1.18,
In vitro $IC_{50}$: 0.015 ng/mL, Spec. Index: >40,500.

EXAMPLE 133 (METHOD A)

Conjugate of 4-(4-acetyl-2-methoxyphenoxy)butanoic acid (15) condensed with Calicheamicin N-acetyl gamma dimethyl hydrazide and h-P67.6.

Loading: 2.3 M/M, Rel. Affinity: 0.78,
In vitro $IC_{50}$: 0.23 ng/mL, Spec. Index: 875.

EXAMPLE 134 (METHOD A)

Conjugate of 4-(4-acetyl-2-methoxyphenoxy)butanoic acid (15) condensed with Calicheamicin N-acetyl gamma dimethyl hydrazide and m-P67.6.

Loading: 1.7 M/M, Rel. Affinity: 0.80,
In vitro $IC_{50}$: 0.029 ng/mL, Spec. Index: 13,500.

EXAMPLE 135 (METHOD A)

Conjugate of 4-[4-(3-oxobutyl)phenoxy]butanoic acid (16) condensed with Calicheamicin N-acetyl gamma dimethyl hydrazide and m-P67.6.

Loading: 0.5 M/M, Rel. Affinity: not determined,
In vitro $IC_{50}$: 9 ng/mL, Spec. Index: 2.

EXAMPLE 136 (METHOD A)

Conjugate of 4-[2-acetyl-5-methoxyphenoxy]butanoic acid (17) condensed with Calicheamicin N-acetyl gamma dimethyl hydrazide and h-P67.6.

Loading: 2.3 M/M, Rel. Affinity: 0.98,
In vitro $IC_{50}$: 0.088 ng/mL, Spec. Index: 1,100.

EXAMPLE 137 (METHOD A)

Conjugate of 4-[2-acetyl-5-methoxyphenoxy]butanoic acid (17) condensed with Calicheamicin N-acetyl gamma dimethyl hydrazide and m-P67.6.

Loading: 1.6 M/M, Rel. Affinity: 1.20,
In vitro $IC_{50}$: 0.0098 ng/mL, Spec. Index: 21,500.

EXAMPLE 138 (METHOD A)

Conjugate of 4-[4-(3-oxopropyl)phenoxy]butanoic acid (18) condensed with Calicheamicin N-acetyl gamma dimethyl hydrazide and h-P67.6.

Loading: 1.0 M/M, Rel. Affinity: 0.80,
In vitro $IC_{50}$: 1.1 ng/mL, Spec. Index: 80.

EXAMPLE 139 (METHOD A)

Conjugate of 4-[4-(3-oxopropyl)phenoxy]butanoic acid (18) condensed with Calicheamicin N-acetyl gamma dimethyl hydrazide and m-P67.6.

Loading: 0.6 M/M, Rel. Affinity: 1.21,
In vitro $IC_{50}$: 0.62 ng/mL, Spec. Index: 90.

EXAMPLE 140 (METHOD A)

Conjugate of 4-acetylbenzenebutanoic acid (19) condensed with Calicheamicin N-acetyl gamma dimethyl hydrazide and h-P67.6.

Loading: 2.6 M/M, Rel. Affinity: 0.50,
In vitro $IC_{50}$: 0.012 ng/mL, Spec. Index: 2,600,
In vivo: 23% T/C (0.5 µg×3 doses, 5/5 alive-28d),
   10% T/C (1 µg×3 doses, 5/5 alive-28d),
   4% T/C (3 µg×3 doses, 4/5 alive-28d),
   0% T/C (6 µg×3 doses, 2/5 alive-28d),
Ex vivo: 99% inhibition.

EXAMPLE 141 (METHOD A)

Conjugate of 4-acetylbenzenebutanoic acid (19) condensed with Calicheamicin N-acetyl gamma dimethyl hydrazide and m-P67.6.

Loading: 2.2 M/M, Rel. Affinity: 0.42,
In vitro IC$_{50}$: 0.0082 ng/mL, Spec. Index: 31,500,
In vivo: 21% T/C (0.5 μg×3 doses, 5/5 alive-28d),
25% T/C (1 μg×3 doses, 5/5 alive-28d),
0% T/C (3 μg×3 doses, 4/5 alive-28d),
0% T/C (6 μg×3 doses, 1/5 alive-28d),
Ex vivo: 99% inhibition.

EXAMPLE 142 (METHOD A)

Conjugate of 4-[(2-acetyl-1-naphthalenyl)oxy] butanoic acid (20) condensed with Calicheamicin N-acetyl gamma dimethyl hydrazide and h-P67.6.

Loading: 2.5 M/M, Rel. Affinity: 0.50,
In vitro IC$_{50}$: 0.061 ng/mL, Spec. Index: 5,000,
In vivo: 36% T/C (1 μg×3 doses, 5/5 alive-28d),
22% T/C (3 μg×3 doses, 5/5 alive-28d),
11% T/C (6 μg×3 doses, 4/5 alive-28d),
Ex vivo: 76% inhibition.

EXAMPLE 143 (METHOD A)

Conjugate of 4-[(2-acetyl-1-naphthalenyl)oxy] butanoic acid (20) condensed with Calicheamicin N-acetyl gamma dimethyl hydrazide and m-P67.6.

Loading: 1.8 M/M, Rel. Affinity: 0.66,
In vitro IC$_{50}$: 0.0067 ng/mL, Spec. Index: 105,000.

EXAMPLE 144 (METHOD A)

Conjugate of 4-[4-(4-fluorobenzoyl)phenoxy]butanoic acid (21) condensed with Calicheamicin N-acetyl gamma dimethyl hydrazide and h-P67.6.

Loading: 2.5 M/M, Rel. Affinity: 0.67,
In vitro IC$_{50}$: 99 ng/mL, Spec. Index: 3.

EXAMPLE 145 (METHOD A)

Conjugate of 4-[4-(4-fluorobenzoyl)phenoxy]butanoic acid (21) condensed with Calicheamicin N-acetyl gamma dimethyl hydrazide and h-P67.6.

Loading: 1.8 M/M, Rel. Affinity: 0.76,
In vitro IC$_{50}$: 63 ng/mL, Spec. Index: 9.

EXAMPLE 146 (METHOD A)

Conjugate of 4-(4-acetylphenyl)-1-piperazinepentanoic acid (22) condensed with Calicheamicin N-acetyl gamma dimethyl hydrazide and h-P67.6.

Loading: 0.1 M/M, Rel. Affinity: 0.98,
In vitro IC$_{50}$: 12 ng/mL, Spec. Index: 2.

EXAMPLE 147 (METHOD A)

Conjugate of 11-(4-acetylphenoxy)undecanoic acid (23) condensed with Calicheamicin N-acetyl gamma dimethyl hydrazide and h-P67.6.

Loading: 0.5 M/M, Rel. Affinity: 0.80,
In vitro IC$_{50}$: 0.43 ng/mL, Spec. Index: 175.

EXAMPLE 148 (METHOD A)

Conjugate of 11-(4-acetylphenoxy)undecanoic acid (23) condensed with Calicheamicin N-acetyl gamma dimethyl hydrazide and m-P67.6.

Loading: 0.4 M/M, Rel. Affinity: 1.16,
In vitro IC$_{50}$: 0.47 ng/mL, Spec. Index: 125.

EXAMPLE 149 (METHOD A)

Conjugate of 5-[(4-acetylphenyl)amino]-5-oxopentanoic acid (24) condensed with Calicheamicin N-acetyl gamma dimethyl hydrazide and m-P67.6.

Loading: 2.0 M/M, Rel. Affinity: 0.73,
In vitro IC$_{50}$: <0.005 ng/mL, Spec. Index: >1,200.

EXAMPLE 150 (METHOD A)

Conjugate of 4-(2-chloro-4-formylphenoxy)butanoic acid (25) condensed with Calicheamicin N-acetyl gamma dimethyl hydrazide and h-P67.6.

Loading: 2.0 M/M, Rel. Affinity: 0.31,
In vitro IC$_{50}$: 0.0071 ng/mL, Spec. Index: 1,500.

EXAMPLE 151 (METHOD A)

Conjugate of 5-acetyl-2-(3-carboxypropoxy)benzoic acid (26), methyl ester condensed with Calicheamicin N-acetyl gamma dimethyl hydrazide and h-P67.6.

Loading: 2.0 M/M, Rel. Affinity: 0.79,
In vitro IC$_{50}$: <0.005 ng/mL, Spec. Index: >9,600.

EXAMPLE 152 (METHOD A)

Conjugate of 4-(4-formyl-2-nitrophenoxy)butanoic acid (27) condensed with Calicheamicin N-acetyl gamma dimethyl hydrazide and h-P67.6.

Loading: 1.5 M/M, Rel. Affinity: 1.3,
In vitro IC$_{50}$: 0.023 ng/mL, Spec. Index: >4,500.

EXAMPLE 153 (METHOD A)

Conjugate of 4-[2-[[(4-acetylphenyl)amino]methyl]-6-methoxyphenoxy]butanoic acid (28) condensed with Calicheamicin N-acetyl gamma dimethyl hydrazide and h-P67.6.

Loading: 2.0 M/M, Rel. Affinity: 0.85,
In vitro IC$_{50}$: <0.005 ng/mL, Spec. Index: >5,000.

EXAMPLE 154 (METHOD A)

Conjugate of 4-(4-acetyl-3-fluorophenoxy)butanoic acid (30) condensed with Calicheamicin N-acetyl gamma dimethyl hydrazide and h-P67.6.

Loading: 1.5 M/M, Rel. Affinity: 1.01,
In vitro IC$_{50}$: 0.005 ng/mL, Spec. Index: 4,800.

EXAMPLE 155 (METHOD A)

Conjugate of 4-(2-Acetylphenoxy)butanoic acid (31) condensed with Calicheamicin N-acetyl gamma dimethyl hydrazide and h-P67.6.

Loading: 1.5 M/M, Rel. Affinity: 0.95,
In vitro IC$_{50}$: <0.005 ng/mL, Spec. Index: >7,000.

EXAMPLE 156 (METHOD A)

Conjugate of 2-acetyl-10H-phenothiazine-10-hexanoic acid (32) condensed with Calicheamicin N-acetyl gamma dimethyl hydrazide and h-P67.6.

Loading: 1.5 M/M, Rel. Affinity: 1.25,
In vitro IC$_{50}$: 0.021 ng/mL, Spec. Index: 2,300.

EXAMPLE 157 (METHOD A)

Conjugate of 4-acetylphenylacetic acid (33) condensed with Calicheamicin N-acetyl gamma dimethyl hydrazide and h-P67.6.

Loading: 1.4 M/M, Rel. Affinity: 0.91,

In vitro $IC_{50}$: <0.005 ng/mL, Spec. Index: 4,700.

The described conjugates are useful for inhibiting the growth of unwanted cells which is an important part of the invention. Accordingly, the invention also includes pharmaceutical compositions, most preferably a parenteral composition suitable for injection into the body of a warm-blooded mammal. Such compositions are formulated by methods which are commonly used in pharmaceutical chemistry. The conjugates are acceptably soluble in physiologically-acceptable fluids, such as physiological saline solutions and other aqueous solutions which can safely be administered parenterally.

Products for parenteral administration are often formulated and distributed in solid, preferably freeze-dried form, for reconstitution immediately before use. Such formulations are useful compositions of the present invention. Their preparation is well understood by pharmaceutical chemists; in general, they comprise mixtures of inorganic salts, to confer isotonicity, and dispersing agents, such as sucrose, to allow the dried preparation to dissolve quickly upon reconstitution. Such formulations are reconstituted with highly purified water or physiologically acceptable buffers to a known concentration, based on the drug. A preferred freeze-dried pharmaceutical composition for inhibiting the growth of cells is obtained by freeze-drying an approximately 1 mg/ml solution of the conjugate dissolved in about 5 mM sodium phosphate buffer at a pH of about 7.4 containing about 100 mM sodium chloride and about 100 mM sucrose. For the conjugate, which has the formula $Z^3[CO-Alk^1-Sp^1-Ar-Sp^2-Alk^2-C(Z^1)=Z^2]m$, $Z^3$ is preferably antibody h-CT-M-01 or h-p67.6; $Alk^1$ is preferably $C_4$ alkylene; $Sp^1$ is preferably —O—; Ar is preferably 1,4-phenylene; $Alk^2$ and $Sp^2$ preferably are together a bond; $Z^1$ is preferably $C_1$ alkyl; and $Z^2$ is preferably calicheamicin N-acetyl gamma dimethyl hydrazide.

The optimum dosage and administration schedule of conjugates of the invention must be determined by the treating physician, in light of the patient's condition.

It is customary, of course, to administer cytotoxic drugs in the form of divided doses, with intervals of days or weeks between each series of doses. The conjugates are effective over a wide dosage range, and dosages per week will usually fall within the range from about 1 to about 10,000 $\mu g/m^2$ of drug, more preferably in the range from about 10 to about 200 $\mu g/m^2$.

---

We claim:

1. A process for preparing the targeted derivatives of formula $$Z^3(CO-Alk^1-Sp^1-Ar-Sp^2-Alk^2-C(Z^1)=Z^2)m$$

wherein $Z^3$ is a protein selected from mono- and polyclonal antibodies, their antigen-recognizing fragments, and their chemically or genetically manipulated counterparts;

$Alk^1$ and $Alk^2$ are independently a bond or branched or unbranched ($C_1$–$C_{10}$) alkylene chain;

$Sp^1$ is a bond, —S—, —O—, —CONH—, —NHCO—, —NR'—, —N(CH$_2$CH$_2$)$_2$N—, or -X-Ar'-Y-(CH$_2$)$_n$-Z wherein X, Y, and Z are independently a bond, —NR'—, —S—, or —O—, with the proviso that when n=0, then at least one of Y and Z must be a bond and Ar' is 1,2-, 1,3-, or 1,4-phenylene optionally substituted with one, two, or three groups of ($C_1$–$C_5$) alkyl, ($C_1$–$C_4$) alkoxy, ($C_1$–$C_4$) thioalkoxy, halogen, nitro, COOR', CONHR', O(CH$_2$)$_n$COOR', S(CH$_2$)$_n$COOR', O(CH$_2$)$_n$CONHR', or S(CH$_2$)$_n$CONHR', with the proviso that when $Alk^{1'}$ is a bond, $Sp^{1'}$ is a bond;

n is an integer from 0 to 5;

R' is a branched or unbranched ($C_1$–$C_5$) chain optionally substituted by one or two groups of —OH, ($C_1$–$C_4$) alkoxy, ($C_1$–$C_4$) thioalkoxy, halogen, nitro, ($C_1$–$C_3$) dialkylamino, or ($C_1$–$C_3$) trialkylammonium-A⁻ where A⁻ is a pharmaceutically acceptable anion completing a salt;

Ar is 1,2-, 1,3-, or 1,4-phenylene optionally substituted with one, two, or three groups of ($C_1$–$C_6$) alkyl, ($C_1$–$C_5$) alkoxy, ($C_1$–$C_4$) thioalkoxy, halogen, nitro, or COOR', CONHR', O(CH$_2$)$_n$COOR', S(CH$_2$)$_n$COOR', O(CH$_2$)$_n$CONHR', or S(CH$_2$)$_n$CONHR' wherein n and R' are as defined above or a 1,2-, 1,3-, 1,4-, 1,5-, 1,6-, 1,7-, 1,8-, 2,3-, 2,6-, or 2,7-naphthylidene or

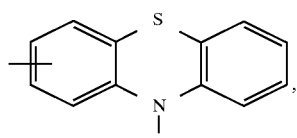

each naphthylidene or phenothiazine optionally substituted with one, two, three, or four groups of ($C_1$–$C_6$) alkyl, ($C_1$–$C_5$) alkoxy, ($C_1$–$C_4$) thioalkoxy, halogen, nitro, COOR', CONHR', O(CH$_2$)$_n$COOR', S(CH$_2$)$_n$COOR', O(CH$_2$)$_n$CONHR', or S(CH$_2$)$_n$CONHR' wherein n and R' are as defined above, with the proviso that when Ar is naphthylidene, $Z^1$ is not hydrogen and with the proviso that when Ar is phenothiazine, $Sp^1$ is a bond only connected to nitrogen;

$Sp^2$ is a bond, —S—, or —O—, with the proviso that when $Alk^2$ is a bond, $Sp^2$ is a bond;

$Z^1$ is H, ($C_1$–$C_5$) alkyl, or phenyl optionally substituted with one, two, or three groups of ($C_1$–$C_5$) alkyl, ($C_1$–$C_4$) alkoxy, ($C_1$–$C_4$) thioalkoxy, halogen, nitro, COOR', CONHR', O(CH$_2$)$_n$COOR', S(CH$_2$)$_n$COOR', O(CH$_2$)$_n$CONHR', or S(CH$_2$)$_n$CONHR' wherein n and R' are as defined above;

$z^2$ is Q-Sp-S-S-W, wherein W is

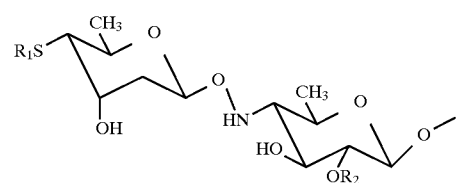

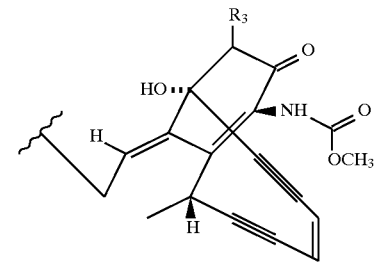

$R_1$ is 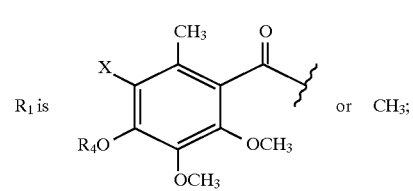 or $CH_3$;

-continued

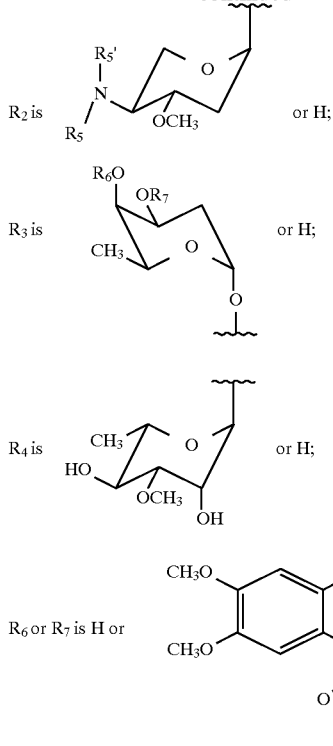

$R_6$ or $R_7$ is H or ;

$R_5$ is —$CH_3$, —$C_2H_5$, or —$CH(CH_3)_2$; X is an iodine or bromine atom; $R_5'$ is a hydrogen or the group RCO, wherein R is hydrogen, branched or unbranched ($C_1$–$C_{10}$) alkyl or ($C_1$–$C_{10}$) alkylene group, a ($C_6$–$C_{11}$) aryl group, a ($C_6$–$C_{11}$) aryl-alkyl ($C_1$–$C_5$) group, or a heteroaryl or heteroaryl- alkyl ($C_1$–$C_5$) group wherein heteroaryl is 2- or 3-furyl, 2- or 3-thienyl, 2- or 3-(N-methylpyrrolyl), 2-, 3-, or 4-pyridyl, 2-, 4-, or 5-(N-methylimidizolyl), 2-, 4-, or 5-oxazolyl, 2-, 3-, 5-, or 6-pyrimidinyl, 2-, 3-, 4-, 5-, 6-, 7-, or 8-quinolyl, or 1-, 3-, 4-, 5-, 6-, 7-, or 8-isoquinolyl, all aryl and heteroaryl optionally substituted by one or more hydroxy, amino, carboxy, halo, nitro, lower ($C_1$–$C_3$) alkoxy, or lower ($C_1$–$C_5$) thioalkoxy groups;

Sp is a straight or branched-chain divalent or trivalent ($C_1$–$C_{18}$) radical, divalent or trivalent aryl or heteroaryl radical, divalent or trivalent ($C_3$–$C_{18}$) cycloalkyl or heterocycloalkyl radical, divalent or trivalent aryl- or heteroaryl-alkyl ($C_1$–$C_{18}$) radical, divalent or trivalent cycloalkyl- or heterocycloalkyl-alkyl ($C_1$–$C_{18}$) radical or divalent or trivalent ($C_2$–$C_{18}$) unsaturated alkyl radical, wherein heteroaryl is furyl, thienyl, N-methylpyrrolyl, pyridinyl, N-methylimidazolyl, oxazolyl, pyrimidinyl, quinolyl, isoquinolyl, N-methylcarbazoyl, aminocoumarinyl, or phenazinyl and wherein when Sp is a trivalent radical, Sp may be additionally substituted by lower ($C_1$–$C_5$) dialkylamino, lower ($C_1$–$C_5$) alkoxy, hydroxy, or lower ($C_1$–$C_5$) alkylthio groups;

Q is =NHNCO—, =NHNCS—, =NHNCONH—, =NHNCSNH—, or =NO—; and m is from about 0.1 to 15;

comprising the steps of:

(a) reacting $H_2Z^2$ with a compound of formula

HOCO-Alk$^1$-Sp$^1$-Ar-Sp$^2$-Alk$^2$-C(Z$^1$)=O, in an alcoholic solvent with a boiling point of less than about 100° C. in the presence of about 5% acetic acid or a carboxylic acid catalyst at about 20° to 70° C. for about 1 to 24 hours, wherein Alk$^1$ and Alk$^2$, Sp$^1$, n, R', Sp$^2$, Z$^1$, and Ar are as defined above, to produce an intermediate of formula HOCO-Alk$^1$-Sp$^1$-Ar-Sp$^2$-Alk$^2$-C(Z$^1$)=Z$^2$, wherein Alk$^1$, Sp$^1$, Ar, Sp$^2$, Alk$^2$, Z$^1$, and Z$^2$ are as defined above;

(b) isolating the intermediate of step (a);

(C) reacting the isolated intermediate of step (b) with N-hydroxysuccinimide, 2, 3, 5, 6-tetrafluorophenol, pentafluorophenol, 4-nitrophenol, 2,4-dinitrophenol, or N-hydroxysulfosuccinimide in the presence of DCC, EDCI, or other carbodiimide in an inert organic solvent such as acetonitrile or acetonitrile containing 5–50% DMF to generate the compound Z$^3$CO-Alk$^1$-Sp$^1$-Ar-Sp$^2$-Alk$^2$-C(Z$^1$)=Z$^2$, wherein Alk$^1$, Sp$^1$, Ar, Sp$^2$, Alk$^2$, Z$^1$, and Z$^2$ are as defined above; and Z$^3$ is

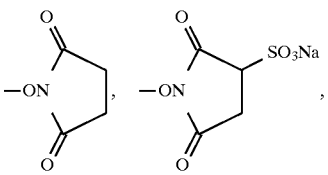

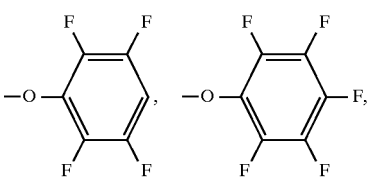

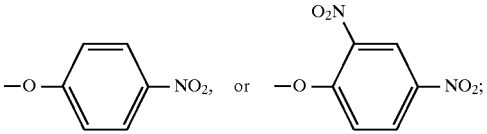

and (d) reacting the compound generated in step (C) of formula

Z$^3$CO-Alk$^1$-Sp$^1$-Ar-Sp$^2$-Alk$^2$-C(Z$^1$)=Z$^2$ with a carrier Z$^3$, wherein Z$^3$ is a protein selected from mono- and polyclonal antibodies, their antigen-recognizing fragments, and their chemically or genetically manipulated counterparts, in an aqueous, buffered solution at a pH of between 6.5 and 9.0 and a temperature of 4° to 40° C. for 1 to 48 hours to generate the targeted derivatives of formula Z$^3$(CO-Alk$^1$-Sp$^1$-Ar-Sp$^2$-Alk$^2$-C(Z$^1$)=Z$^2$)m defined above.

2. The process of claim 1, wherein Alk$^2$ and Sp$^2$ are together a bond and Z$^1$ is H or ($C_1$–$C_5$) alkyl.

3. The process of claim 2, wherein Sp$^1$ is a bond, —S—, —O—, —CONH—, —NHCO—, or —NR', with the proviso that when Sp$^1$ is a bond, Alk$^1$ is a bond.

4. The process of claim 3, wherein Ar is 1,2-, 1,3-, or 1,4-phenylene optionally substituted with one, two, or three groups of ($C_1$–$C_6$) alkyl, ($C_1$–$C_5$) alkoxy, ($C_1$–$C_4$)

thioalkoxy, halogen, nitro, or COOR', CONHR', O(CH$_2$)$_n$ COOR', S(CH$_2$)$_n$COOR', O(CH$_2$)$_n$CONHR', or S(CH$_2$)$_n$CONHR' or a 1,2-, 1,3-, 1,4-, 1,5-, 1,6-, 1,7-, 1,8-, 2,3-, 2,6-, or 2,7-naphthylidene, each optionally substituted With one, two, three, or four groups of (C$_1$–C$_6$) alkyl, (C$_1$–C$_5$) alkoxy, (C$_1$–C$_4$) thioalkoxy, halogen, nitro, COOR', CONHR', O(CH$_2$)$_n$COOR', S(CH$_2$)$_n$COOR', O(CH$_2$)$_n$CONHR', or S(CH$_2$)$_n$CONHR'.

5. The process of claim 4, wherein a covalent bond to the Z$^3$ protein is an amide formed from a reaction with the lysine side chains of the Z$^3$ protein.

6. The process of claim 5, wherein Z$^2$ is Q-Sp-S-S-W and W is

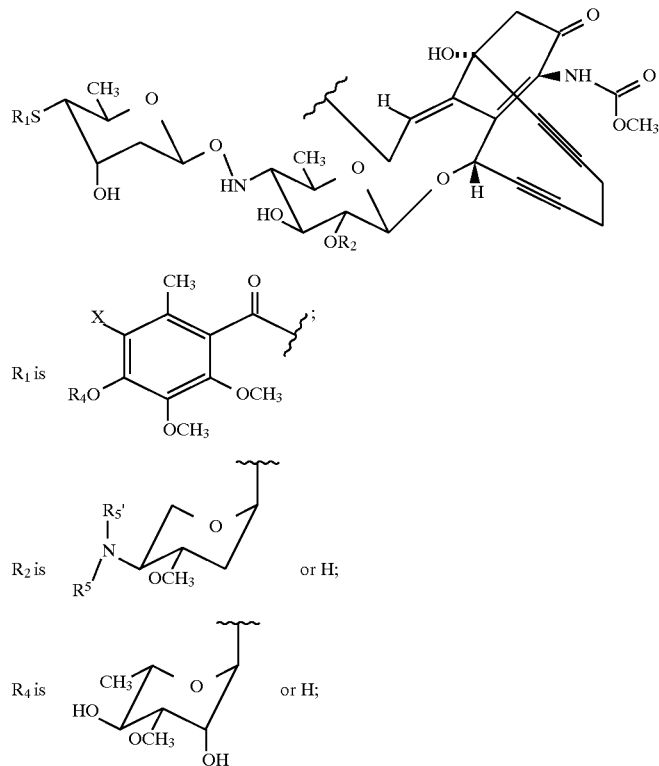

R$_5$, X, R$_5$', R, and Sp are as defined in claim 1, and Q is =NHNCO—.

7. The process of claim 6, wherein the alcoholic solvent of step (a) is methanol; the carboxylic acid catalyst of step (a) is 5% acetic acid; the isolated intermediate of step (b) is reacted in step (C) with N-hydroxysuccinimide in the presence of EDCI in acetonitrile; and the aqueous buffered solution of step (d) is phosphate buffer having a pH of 7.4 to 8.0.

8. The process of claim 7, wherein Z$^1$ is (C$_1$–C$_5$) alkyl.

9. The process of claim 8, wherein Ar is 1,2-, 1,3-, or 1,4-phenylene optionally substituted with one, two, or three groups of (C$_1$–C$_6$) alkyl, (C$_1$–C$_5$) alkoxy, (C$_1$–C$_4$) thioalkoxy, halogen, nitro, or COOR', CONHR', O(CH$_2$)$_n$COOR', S(CH$_2$)$_n$COOR', O(CH$_2$)$_n$CONHR', or S(CH$_2$)$_n$CONHR'.

10. The process of claim 9, wherein Sp$^1$ is —O—, Alk$^1$ is C$_4$ alkylene, Ar is 1,4-phenylene, and Z$^1$ is C$_1$ alkyl.

11. The process of claim 10, wherein Z$^3$ is antibody h-P67.6, h-CT-M-01, m-CT-M-01, h-A33, m-A33 or anti-Tac.

12. The process of claim 11, wherein Z$^2$ is calicheamicin gamma dimethyl hydrazide or calicheamicin N-acetyl gamma dimethyl hydrazide.

13. The process of claim 12, wherein Z$^3$ is antibody h-CT-M-01 and Z$^2$ is calicheamicin N-acetyl gamma dimethyl hydrazide.

14. The process of claim 12, wherein Z$^3$ is antibody h-P67.6 and Z$^2$ is calicheamicin N-acetyl gamma dimethyl hydrazide.

15. The process of claim 4, wherein Sp$^1$ is —O—or a bond; Alk$^1$ is a bond or branched or unbranched (C$_1$–C$_{10}$) alkylene chain, with the proviso that when Alk$^1$ is a bond, Sp$^1$ is a bond; Z$^1$ is (C$_1$–C$_5$) alkyl; and Z$^2$ is calicheamicin N-acetyl gamma dimethyl hydrazide.

* * * * *

UNITED STATES PATENT AND TRADEMARK OFFICE
CERTIFICATE OF CORRECTION

PATENT NO. : 5,877,296

DATED : March 2, 1999

INVENTOR(S) : Philip Ross Hamann, et al

It is certified that error appears in the above-identified patent and that said Letters Patent is hereby corrected as shown below:

On the Title Page, Item [75] Inventors should read: -- Philip Ross Hamann, Garnerville; Lois Hinman, N. Tarrytown; Irwin Hollander, Monsey, all of N.Y. ---.

Signed and Sealed this

Sixteenth Day of May, 2000

*Attest:*

Q. TODD DICKINSON

*Attesting Officer*     *Director of Patents and Trademarks*

SEQUENCE LISTING ( 1 ) GENERAL INFORMATION:

( i i i ) NUMBER OF SEQUENCES: 73

( 2 ) INFORMATION FOR SEQ ID NO:1:

( i ) SEQUENCE CHARACTERISTICS:
        ( A ) LENGTH: 426 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 22..420

( x i ) SEQUENCE DESCRIPTION: SEQ ID NO:1:

```
GGACTGTTCG AAGCCGCCAC C ATG TCT GTC CCC ACC CAA GTC CTC GGA CTC      51
                         Met Ser Val Pro Thr Gln Val Leu Gly Leu
                          1               5                    10

CTG CTG CTG TGG CTT ACA GAT GCC AGA TGC GAT ATC CAG CTC ACT CAG      99
Leu Leu Leu Trp Leu Thr Asp Ala Arg Cys Asp Ile Gln Leu Thr Gln
              15                   20                  25

AGT CCA AGT ACT CTC AGT GCC AGT GTA GGT GAT AGG GTC ACC ATC ACT     147
Ser Pro Ser Thr Leu Ser Ala Ser Val Gly Asp Arg Val Thr Ile Thr
             30                  35                  40

TGT AGG GCC TCT GAA TCT CTC GAT AAC TAT GGT ATC AGG TTC CTC ACT     195
Cys Arg Ala Ser Glu Ser Leu Asp Asn Tyr Gly Ile Arg Phe Leu Thr
            45                   50                  55

TGG TTC CAG CAG AAA CCA GGT AAA GCC CCA AAG CTC CTC ATG TAT GCC     243
Trp Phe Gln Gln Lys Pro Gly Lys Ala Pro Lys Leu Leu Met Tyr Ala
        60                   65                  70

GCC TCT AAC CAG GGT TCT GGT GTA CCA TCT AGA TTC AGT GGT AGT GGT     291
Ala Ser Asn Gln Gly Ser Gly Val Pro Ser Arg Phe Ser Gly Ser Gly
```

```
                         75                          80                             85                            90
AGT  GGT  ACT  GAG  TTC  ACT  CTC  ACT  ATC  AGT  AGT  CTC  CAG  CCA  GAT  GAT        339
Ser  Gly  Thr  Glu  Phe  Thr  Leu  Thr  Ile  Ser  Ser  Leu  Gln  Pro  Asp  Asp
                    95                       100                      105

TTC  GCC  ACT  TAT  TAT  TGT  CAG  CAG  ACT  AAA  GAA  GTA  CCA  TGG  TCT  TTC        387
Phe  Ala  Thr  Tyr  Tyr  Cys  Gln  Gln  Thr  Lys  Glu  Val  Pro  Trp  Ser  Phe
               110                      115                      120

GGT  CAG  GGT  ACT  AAA  GTA  GAA  GTA  AAA  CGT  ACG  GGCCGG                         426
Gly  Gln  Gly  Thr  Lys  Val  Glu  Val  Lys  Arg  Thr
          125                      130
```

( 2 ) INFORMATION FOR SEQ ID NO:2:

( i ) SEQUENCE CHARACTERISTICS:
        ( A ) LENGTH: 133 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Ser  Val  Pro  Thr  Gln  Val  Leu  Gly  Leu  Leu  Leu  Leu  Trp  Leu  Thr
 1                   5                        10                       15

Asp  Ala  Arg  Cys  Asp  Ile  Gln  Leu  Thr  Gln  Ser  Pro  Ser  Thr  Leu  Ser
               20                       25                       30

Ala  Ser  Val  Gly  Asp  Arg  Val  Thr  Ile  Thr  Cys  Arg  Ala  Ser  Glu  Ser
          35                       40                       45

Leu  Asp  Asn  Tyr  Gly  Ile  Arg  Phe  Leu  Thr  Trp  Phe  Gln  Gln  Lys  Pro
     50                       55                       60

Gly  Lys  Ala  Pro  Lys  Leu  Leu  Met  Tyr  Ala  Ala  Ser  Asn  Gln  Gly  Ser
 65                      70                       75                       80

Gly  Val  Pro  Ser  Arg  Phe  Ser  Gly  Ser  Gly  Ser  Gly  Thr  Glu  Phe  Thr
                    85                       90                       95

Leu  Thr  Ile  Ser  Ser  Leu  Gln  Pro  Asp  Asp  Phe  Ala  Thr  Tyr  Tyr  Cys
               100                      105                      110

Gln  Gln  Thr  Lys  Glu  Val  Pro  Trp  Ser  Phe  Gly  Gln  Gly  Thr  Lys  Val
          115                      120                      125

Glu  Val  Lys  Arg  Thr
130
```

( 2 ) INFORMATION FOR SEQ ID NO:3:

( i ) SEQUENCE CHARACTERISTICS:
        ( A ) LENGTH: 449 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 22..444

( x i ) SEQUENCE DESCRIPTION: SEQ ID NO:3:

```
GCGCGCAAGC  TTGCCGCCAC  C  ATG  GAA  TGG  AGC  TGG  GTC  TTT  CTC  TTC  TTC        51
                           Met  Glu  Trp  Ser  Trp  Val  Phe  Leu  Phe  Phe
                            1                   5                        10

CTG  TCA  GTA  ACT  ACA  GGA  GTC  CAT  TCT  GAG  GTG  CAG  CTG  GTG  CAG  TCT    99
Leu  Ser  Val  Thr  Thr  Gly  Val  His  Ser  Glu  Val  Gln  Leu  Val  Gln  Ser
```

-continued

|  |  | 15 |  |  |  |  |  | 20 |  |  |  |  | 25 |  |  |
|---|---|---|---|---|---|---|---|---|---|---|---|---|---|---|---|
| GGA | GCA | GAG | GTG | AAG | AAG | CCT | GGA | TCT | TCT | GTG | AAG | GTG | TCT | TGT | AAG | 147
| Gly | Ala | Glu | Val | Lys | Lys | Pro | Gly | Ser | Ser | Val | Lys | Val | Ser | Cys | Lys |
|  |  | 30 |  |  |  |  |  | 35 |  |  |  |  | 40 |  |  |
| GCA | TCT | GGA | TAC | ACA | ATT | ACA | GAC | TCC | AAT | ATT | CAC | TGG | GTG | AGA | CAG | 195
| Ala | Ser | Gly | Tyr | Thr | Ile | Thr | Asp | Ser | Asn | Ile | His | Trp | Val | Arg | Gln |
|  |  | 45 |  |  |  |  |  | 50 |  |  |  |  | 55 |  |  |
| GCA | CCT | GGA | CAG | TCC | CTC | GAG | TGG | ATT | GGA | TAC | ATT | TAC | CCT | TAC | AAT | 243
| Ala | Pro | Gly | Gln | Ser | Leu | Glu | Trp | Ile | Gly | Tyr | Ile | Tyr | Pro | Tyr | Asn |
|  |  | 60 |  |  |  |  |  | 65 |  |  |  |  | 70 |  |  |
| GGA | GGA | ACA | GAC | TAC | AAT | CAG | AAG | TTC | AAG | AAT | AGA | GCA | ACA | CTG | ACA | 291
| Gly | Gly | Thr | Asp | Tyr | Asn | Gln | Lys | Phe | Lys | Asn | Arg | Ala | Thr | Leu | Thr |
|  | 75 |  |  |  |  | 80 |  |  |  |  | 85 |  |  |  | 90 |
| GTG | GAC | AAT | CCT | ACG | AAT | ACC | GCC | TAC | ATG | GAG | CTG | TCT | TCT | CTG | AGA | 339
| Val | Asp | Asn | Pro | Thr | Asn | Thr | Ala | Tyr | Met | Glu | Leu | Ser | Ser | Leu | Arg |
|  |  |  |  | 95 |  |  |  |  | 100 |  |  |  |  | 105 |  |
| TCT | GAG | GAC | ACA | GAC | TTC | TAC | TAC | TGT | GTG | AAT | GGA | AAT | CCT | TGG | CTG | 387
| Ser | Glu | Asp | Thr | Asp | Phe | Tyr | Tyr | Cys | Val | Asn | Gly | Asn | Pro | Trp | Leu |
|  |  |  | 110 |  |  |  |  | 115 |  |  |  |  | 120 |  |  |
| GCT | TAC | TGG | GGA | CAG | GGA | ACA | CTG | GTG | ACA | GTG | TCT | TCT | GCC | TCA | ACG | 435
| Ala | Tyr | Trp | Gly | Gln | Gly | Thr | Leu | Val | Thr | Val | Ser | Ser | Ala | Ser | Thr |
|  |  | 125 |  |  |  |  |  | 130 |  |  |  |  | 135 |  |  |
| AAG | GGC | CCG | CGCGC |  |  |  |  |  |  |  |  |  |  |  |  | 449
| Lys | Gly | Pro |  |  |  |  |  |  |  |  |  |  |  |  |  |
|  |  | 140 |  |  |  |  |  |  |  |  |  |  |  |  |  |

( 2 ) INFORMATION FOR SEQ ID NO:4:

( i ) SEQUENCE CHARACTERISTICS:
        ( A ) LENGTH: 141 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| Met | Glu | Trp | Ser | Trp | Val | Phe | Leu | Phe | Phe | Leu | Ser | Val | Thr | Thr | Gly |
|---|---|---|---|---|---|---|---|---|---|---|---|---|---|---|---|
| 1 |  |  |  | 5 |  |  |  |  | 10 |  |  |  |  | 15 |  |
| Val | His | Ser | Glu | Val | Gln | Leu | Val | Gln | Ser | Gly | Ala | Glu | Val | Lys | Lys |
|  |  |  | 20 |  |  |  |  | 25 |  |  |  |  | 30 |  |  |
| Pro | Gly | Ser | Ser | Val | Lys | Val | Ser | Cys | Lys | Ala | Ser | Gly | Tyr | Thr | Ile |
|  |  | 35 |  |  |  |  | 40 |  |  |  |  | 45 |  |  |  |
| Thr | Asp | Ser | Asn | Ile | His | Trp | Val | Arg | Gln | Ala | Pro | Gly | Gln | Ser | Leu |
|  | 50 |  |  |  |  | 55 |  |  |  |  | 60 |  |  |  |  |
| Glu | Trp | Ile | Gly | Tyr | Ile | Tyr | Pro | Tyr | Asn | Gly | Gly | Thr | Asp | Tyr | Asn |
| 65 |  |  |  |  | 70 |  |  |  |  | 75 |  |  |  |  | 80 |
| Gln | Lys | Phe | Lys | Asn | Arg | Ala | Thr | Leu | Thr | Val | Asp | Asn | Pro | Thr | Asn |
|  |  |  |  | 85 |  |  |  |  | 90 |  |  |  |  | 95 |  |
| Thr | Ala | Tyr | Met | Glu | Leu | Ser | Ser | Leu | Arg | Ser | Glu | Asp | Thr | Asp | Phe |
|  |  |  | 100 |  |  |  |  | 105 |  |  |  |  | 110 |  |  |
| Tyr | Tyr | Cys | Val | Asn | Gly | Asn | Pro | Trp | Leu | Ala | Tyr | Trp | Gly | Gln | Gly |
|  |  | 115 |  |  |  |  | 120 |  |  |  |  | 125 |  |  |  |
| Thr | Leu | Val | Thr | Val | Ser | Ser | Ala | Ser | Thr | Lys | Gly | Pro |  |  |  |
|  | 130 |  |  |  |  | 135 |  |  |  |  | 140 |  |  |  |  |

( 2 ) INFORMATION FOR SEQ ID NO:5:

( i ) SEQUENCE CHARACTERISTICS:
        ( A ) LENGTH: 214 amino acids
        ( B ) TYPE: amino acid
        ( C ) STRANDEDNESS: single -continued (D) TOPOLOGY: linear (ii) MOLECULE TYPE: protein (xi) SEQUENCE DESCRIPTION: SEQ ID NO:5:

| Asp | Ile | Gln | Met | Thr | Gln | Ser | Pro | Ser | Thr | Leu | Ser | Ala | Ser | Val | Gly |
|---|---|---|---|---|---|---|---|---|---|---|---|---|---|---|---|
| 1 | | | | 5 | | | | | 10 | | | | | 15 | |
| Asp | Arg | Val | Thr | Ile | Thr | Cys | Arg | Ala | Ser | Gln | Ser | Ile | Asn | Thr | Trp |
| | | | 20 | | | | | 25 | | | | | 30 | | |
| Leu | Ala | Trp | Tyr | Gln | Gln | Lys | Pro | Gly | Lys | Ala | Pro | Lys | Leu | Leu | Met |
| | | 35 | | | | | 40 | | | | | 45 | | | |
| Tyr | Lys | Ala | Ser | Ser | Leu | Glu | Ser | Gly | Val | Pro | Ser | Arg | Phe | Ile | Gly |
| | 50 | | | | | 55 | | | | | 60 | | | | |
| Ser | Gly | Ser | Gly | Thr | Glu | Phe | Thr | Leu | Thr | Ile | Ser | Ser | Leu | Gln | Pro |
| 65 | | | | | 70 | | | | | 75 | | | | | 80 |
| Asp | Asp | Phe | Ala | Thr | Tyr | Tyr | Cys | Gln | Gln | Tyr | Asn | Ser | Asp | Ser | Lys |
| | | | | 85 | | | | | 90 | | | | | 95 | |
| Met | Phe | Gly | Gln | Gly | Thr | Lys | Val | Glu | Val | Lys | Gly | Thr | Val | Ala | Ala |
| | | | 100 | | | | | 105 | | | | | 110 | | |
| Pro | Ser | Val | Phe | Ile | Phe | Pro | Pro | Ser | Asp | Glu | Gln | Leu | Lys | Ser | Gly |
| | | 115 | | | | | 120 | | | | | 125 | | | |
| Thr | Ala | Ser | Val | Val | Cys | Leu | Leu | Asn | Asn | Phe | Tyr | Pro | Arg | Glu | Ala |
| | | 130 | | | | | 135 | | | | | 140 | | | |
| Lys | Val | Gln | Trp | Lys | Val | Asp | Asn | Ala | Leu | Gln | Ser | Gly | Asn | Ser | Gln |
| 145 | | | | | 150 | | | | | 155 | | | | | 160 |
| Glu | Ser | Val | Thr | Glu | Gln | Asp | Ser | Lys | Asp | Ser | Tyr | Tyr | Ser | Leu | Ser |
| | | | | 165 | | | | | 170 | | | | | 175 | |
| Ser | Thr | Leu | Thr | Leu | Ser | Lys | Ala | Asp | Tyr | Glu | Lys | His | Lys | Val | Tyr |
| | | | 180 | | | | | 185 | | | | | 190 | | |
| Ala | Cys | Glu | Val | Thr | His | Gln | Gly | Leu | Ser | Ser | Pro | Val | Thr | Lys | Ser |
| | | 195 | | | | | 200 | | | | | 205 | | | |
| Phe | Asn | Arg | Gly | Glu | Cys | | | | | | | | | | |
| | | | | 210 | | | | | | | | | | | |

(2) INFORMATION FOR SEQ ID NO:6:

(i) SEQUENCE CHARACTERISTICS:
      (A) LENGTH: 252 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:6:

| Xaa | Val | Gln | Leu | Val | Gln | Ser | Gly | Ala | Glu | Val | Lys | Lys | Pro | Gly | Ser |
|---|---|---|---|---|---|---|---|---|---|---|---|---|---|---|---|
| 1 | | | | 5 | | | | | 10 | | | | | 15 | |
| Ser | Val | Lys | Val | Ser | Cys | Lys | Ala | Ser | Gly | Gly | Thr | Phe | Ser | Arg | Ser |
| | | | 20 | | | | | 25 | | | | | 30 | | |
| Ala | Ile | Ile | Trp | Val | Arg | Gln | Ala | Pro | Gly | Gln | Gly | Leu | Glu | Trp | Met |
| | | | 35 | | | | | 40 | | | | | 45 | | |
| Gly | Gly | Ile | Val | Pro | Met | Phe | Gly | Pro | Pro | Asn | Tyr | Ala | Gln | Lys | Phe |
| | | | 50 | | | | | 55 | | | | | 60 | | |
| Gln | Gly | Arg | Val | Thr | Ile | Thr | Ala | Asp | Glu | Ser | Thr | Asn | Thr | Ala | Tyr |
| 65 | | | | | 70 | | | | | 75 | | | | | 80 |
| Met | Glu | Leu | Ser | Ser | Leu | Arg | Ser | Glu | Asp | Thr | Ala | Phe | Tyr | Phe | Cys |
| | | | | 85 | | | | | 90 | | | | | 95 | |
| Ala | Gly | Gly | Tyr | Gly | Ile | Tyr | Ser | Pro | Glu | Glu | Tyr | Asn | Gly | Gly | Leu |

|   |   |   |   |   | 100 |   |   |   |   | 105 |   |   |   |   | 110 |   |   |
|---|---|---|---|---|---|---|---|---|---|---|---|---|---|---|---|---|---|
|   | Val | Thr | Val<br>115 | Ser | Ser | Ala | Ser | Thr<br>120 | Lys | Gly | Pro | Ser | Val<br>125 | Phe | Pro | Leu |   |
|   | Ala | Pro<br>130 | Ser | Ser | Lys | Ser | Thr<br>135 | Ser | Gly | Gly | Thr | Ala<br>140 | Ala | Leu | Gly | Cys |   |
|   | Leu | Val | Lys | Asp | Tyr | Phe<br>150 | Pro | Glu | Pro | Val | Thr<br>155 | Val | Ser | Trp | Asn | Ser<br>160 |   |
|   | Gly | Ala | Leu | Thr | Ser<br>165 | Gly | Val | His | Thr | Phe<br>170 | Pro | Ala | Val | Leu | Gln<br>175 | Ser |   |
|   | Ser | Gly | Leu | Tyr<br>180 | Ser | Leu | Ser | Ser | Val<br>185 | Val | Thr | Val | Pro | Ser<br>190 | Ser | Ser |   |
|   | Leu | Gly | Thr<br>195 | Gln | Thr | Tyr | Ile | Cys<br>200 | Asn | Val | Asn | His | Lys<br>205 | Pro | Ser | Asn |   |
|   | Thr | Lys<br>210 | Val | Asp | Lys | Arg | Val<br>215 | Glu | Pro | Lys | Ser | Cys<br>220 | Asp | Lys | Thr | His |   |
|   | Thr<br>225 | Cys | Pro | Pro | Cys | Pro<br>230 | Ala | Pro | Glu | Leu | Leu<br>235 | Gly | Gly | Pro | Ser | Val<br>240 |   |
|   | Phe | Leu | Phe | Pro | Pro<br>245 | Lys | Pro | Lys | Asp | Thr<br>250 | Leu | Met |   |   |   |   |   |

( 2 ) INFORMATION FOR SEQ ID NO:7:

( i ) SEQUENCE CHARACTERISTICS:
        ( A ) LENGTH: 417 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..417

( x i ) SEQUENCE DESCRIPTION: SEQ ID NO:7:

```
ATG  GAA  TGG  AGC  TGG  GTC  TTT  CTC  TTC  TTC  CTG  TCG  GTA  ACC  ACA  GGT        48
Met  Glu  Trp  Ser  Trp  Val  Phe  Leu  Phe  Phe  Leu  Ser  Val  Thr  Thr  Gly
 1                  5                       10                      15

GTC  CAT  TGC  CAG  ATC  CAG  CTG  CAG  CAG  TCT  GGA  CCT  GAG  CTG  GTG  AAG        96
Val  His  Cys  Gln  Ile  Gln  Leu  Gln  Gln  Ser  Gly  Pro  Glu  Leu  Val  Lys
                 20                      25                      30

CCT  GGG  GCT  TCA  GTG  AAG  ATA  TCC  TGC  AAG  GCT  TCT  GGC  TAC  ACC  TTC       144
Pro  Gly  Ala  Ser  Val  Lys  Ile  Ser  Cys  Lys  Ala  Ser  Gly  Tyr  Thr  Phe
            35                      40                      45

ACT  GAC  TAC  TAT  ATA  AAC  TGG  ATG  AAG  CAG  AAG  CCT  GGA  CAG  GGA  CTT       192
Thr  Asp  Tyr  Tyr  Ile  Asn  Trp  Met  Lys  Gln  Lys  Pro  Gly  Gln  Gly  Leu
       50                      55                      60

GAG  TGG  ATT  GGA  TGG  ATT  GAT  CCT  GGA  AGC  GGT  AAT  ACT  AAG  TAC  AAT       240
Glu  Trp  Ile  Gly  Trp  Ile  Asp  Pro  Gly  Ser  Gly  Asn  Thr  Lys  Tyr  Asn
 65                      70                      75                      80

GAG  AAG  TTC  AAG  GGC  AAG  GCC  ACA  TTG  ACT  GTA  GAC  ACA  TCC  TCC  AGC       288
Glu  Lys  Phe  Lys  Gly  Lys  Ala  Thr  Leu  Thr  Val  Asp  Thr  Ser  Ser  Ser
                      85                      90                      95

ACA  GCC  TAC  ATG  CAG  CTC  AGC  AGC  CTG  ACA  TCT  GAG  GAC  ACT  GCT  GTC       336
Thr  Ala  Tyr  Met  Gln  Leu  Ser  Ser  Leu  Thr  Ser  Glu  Asp  Thr  Ala  Val
                100                     105                     110

TAT  TTC  TGT  GCA  AGA  GAG  AAA  ACG  ACC  TAT  TAC  TAT  GCT  ATG  GAC  TAC       384
Tyr  Phe  Cys  Ala  Arg  Glu  Lys  Thr  Thr  Tyr  Tyr  Tyr  Ala  Met  Asp  Tyr
            115                     120                     125

TGG  GGT  CAA  GGA  ACC  TCA  GTC  ACT  GTC  TCC  GCA                                 417
Trp  Gly  Gln  Gly  Thr  Ser  Val  Thr  Val  Ser  Ala
```

130 135

(2) INFORMATION FOR SEQ ID NO:8:

(i) SEQUENCE CHARACTERISTICS:
        (A) LENGTH: 139 amino acids
        (B) TYPE: amino acid
        (D) TOPOLOGY: linear (ii) MOLECULE TYPE: protein (xi) SEQUENCE DESCRIPTION: SEQ ID NO:8:

```
Met Glu Trp Ser Trp Val Phe Leu Phe Phe Leu Ser Val Thr Thr Gly
 1               5                  10                  15
Val His Cys Gln Ile Gln Leu Gln Gln Ser Gly Pro Glu Leu Val Lys
            20                  25                  30
Pro Gly Ala Ser Val Lys Ile Ser Cys Lys Ala Ser Gly Tyr Thr Phe
        35                  40                  45
Thr Asp Tyr Tyr Ile Asn Trp Met Lys Gln Lys Pro Gly Gln Gly Leu
    50                  55                  60
Glu Trp Ile Gly Trp Ile Asp Pro Gly Ser Gly Asn Thr Lys Tyr Asn
65                  70                  75                  80
Glu Lys Phe Lys Gly Lys Ala Thr Leu Thr Val Asp Thr Ser Ser Ser
                85                  90                  95
Thr Ala Tyr Met Gln Leu Ser Ser Leu Thr Ser Glu Asp Thr Ala Val
              100                 105                 110
Tyr Phe Cys Ala Arg Glu Lys Thr Thr Tyr Tyr Ala Met Asp Tyr
            115                 120                 125
Trp Gly Gln Gly Thr Ser Val Thr Val Ser Ala
        130                 135
```

(2) INFORMATION FOR SEQ ID NO:9:

(i) SEQUENCE CHARACTERISTICS:
        (A) LENGTH: 399 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..399

(xi) SEQUENCE DESCRIPTION: SEQ ID NO:9:

```
ATG AGG TGC CTA GCT GAG TTC CTG GGG CTG CTT GTG CTC TGG ATC CCT     48
Met Arg Cys Leu Ala Glu Phe Leu Gly Leu Leu Val Leu Trp Ile Pro
 1               5                  10                  15

GGA GCC ATT GGG GAT ATT GTG ATG ACT CAG GCT GCA CCC TCT GTT CCT     96
Gly Ala Ile Gly Asp Ile Val Met Thr Gln Ala Ala Pro Ser Val Pro
            20                  25                  30

GTC ACT CCT GGA GAG TCA TTA TCC ATT TCC TGC AGG TCT AGT AAG AGT    144
Val Thr Pro Gly Glu Ser Leu Ser Ile Ser Cys Arg Ser Ser Lys Ser
        35                  40                  45

CTC CTT CAT AGT AAT GGC GAC ACT TTC TTG TAT TGG TTC CTG CAG AGG    192
Leu Leu His Ser Asn Gly Asp Thr Phe Leu Tyr Trp Phe Leu Gln Arg
    50                  55                  60

CCA GGC CAG TCT CCT CAA CTC CTG ATA TAT CGG ATG TCC AAC CTT GCC    240
Pro Gly Gln Ser Pro Gln Leu Leu Ile Tyr Arg Met Ser Asn Leu Ala
65                  70                  75                  80

TCC GGA GTC CCA GAC AGG TTC AGT GGC AGT GGG TCA GGA ACT GCT TTC    288
Ser Gly Val Pro Asp Arg Phe Ser Gly Ser Gly Ser Gly Thr Ala Phe
```

|     |     |     |     | 85  |     |     |     | 90  |     |     |     | 95  |     |     |     |
|-----|-----|-----|-----|-----|-----|-----|-----|-----|-----|-----|-----|-----|-----|-----|-----|
| ACA | CTG | AGA | GTC | AGT | AGA | GTG | GAG | GCT | GAG | GAT | GTG | GGT | GTT | TAT | TAC | 336
| Thr | Leu | Arg | Val | Ser | Arg | Val | Glu | Ala | Glu | Asp | Val | Gly | Val | Tyr | Tyr |
|     |     |     | 100 |     |     |     | 105 |     |     |     | 110 |     |     |     |     |

TGT ATG CAA CAT CTA GAA TAT CCT TTC ACG TTC GGT GCT GGG ACC AAG   384
Cys Met Gln His Leu Glu Tyr Pro Phe Thr Phe Gly Ala Gly Thr Lys
            115                 120                 125

CTG GAG CTG AAA CGG   399
Leu Glu Leu Lys Arg
130

( 2 ) INFORMATION FOR SEQ ID NO:10:

( i ) SEQUENCE CHARACTERISTICS:
        ( A ) LENGTH: 133 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

Met Arg Cys Leu Ala Glu Phe Leu Gly Leu Leu Val Leu Trp Ile Pro
 1               5                  10                  15

Gly Ala Ile Gly Asp Ile Val Met Thr Gln Ala Ala Pro Ser Val Pro
            20                  25                  30

Val Thr Pro Gly Glu Ser Leu Ser Ile Ser Cys Arg Ser Ser Lys Ser
        35                  40                  45

Leu Leu His Ser Asn Gly Asp Thr Phe Leu Tyr Trp Phe Leu Gln Arg
    50                  55                  60

Pro Gly Gln Ser Pro Gln Leu Leu Ile Tyr Arg Met Ser Asn Leu Ala
65                  70                  75                  80

Ser Gly Val Pro Asp Arg Phe Ser Gly Ser Gly Ser Gly Thr Ala Phe
                85                  90                  95

Thr Leu Arg Val Ser Arg Val Glu Ala Glu Asp Val Gly Val Tyr Tyr
            100                 105                 110

Cys Met Gln His Leu Glu Tyr Pro Phe Thr Phe Gly Ala Gly Thr Lys
            115                 120                 125

Leu Glu Leu Lys Arg
130

( 2 ) INFORMATION FOR SEQ ID NO:11:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

GCGCGCAAGC TTGCCGCCAC C   21

( 2 ) INFORMATION FOR SEQ ID NO:12:

( i ) SEQUENCE CHARACTERISTICS:
        ( A ) LENGTH: 96 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

TCTCAGATTC AGCTGGTGCA GTCTGGAGCA GAGGTGAAGA AGCCTGGATC TTCTGTGAAG    60

GTGTCTTGTA AGGCATCTGG ATACACCTTC ACCGAC    96

( 2 ) INFORMATION FOR SEQ ID NO:13:

( i ) SEQUENCE CHARACTERISTICS:
        ( A ) LENGTH: 96 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

TGGATTGACC CTGGATCTGG AAATACAAAG TACAATGAGA AGTTCAAGGG AAGAGTGACA    60

ATTACAGTGG ACACATCCAC GAATACCGCC TACATG    96

( 2 ) INFORMATION FOR SEQ ID NO:14:

( i ) SEQUENCE CHARACTERISTICS:
        ( A ) LENGTH: 89 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

GAGAAGACCA CCTACTACTA CGCAATGGAC TACTGGGGAC AGGGAACACT GGTGACAGTG    60

TCTTCTGCCT CAACGAAGGG CCCGCGCGC    89

( 2 ) INFORMATION FOR SEQ ID NO:15:

( i ) SEQUENCE CHARACTERISTICS:
        ( A ) LENGTH: 96 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

CTGCACCAGC TGAATCTGAG AATGGACTCC TGTAGTTACT GACAGGAAGA AGAGAAAGAC    60

CCAGCTCCAT TCCATGGTGG CGGCAAGCTT GCGCGC    96

( 2 ) INFORMATION FOR SEQ ID NO:16:

( i ) SEQUENCE CHARACTERISTICS:
        ( A ) LENGTH: 96 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

TCCAGATCCA GGGTCAATCC ATCCATCCA CTCGAGTCCC TGTCCAGGTG CCTGTCTCAT    60

CCAATTAATG TAGTAGTCGG TGAAGGTGTA TCCAGA    96

( 2 ) INFORMATION FOR SEQ ID NO:17:

( i ) SEQUENCE CHARACTERISTICS:
        ( A ) LENGTH: 93 base pairs
        ( B ) TYPE: nucleic acid
        ( C ) STRANDEDNESS: single (D) TOPOLOGY: linear (ii) MOLECULE TYPE: DNA (genomic)

(xi) SEQUENCE DESCRIPTION: SEQ ID NO:17:

```
GTAGTAGTAG GTGGTCTTCT CTCTTGCACA GAAGTAGAAT GCTGTGTCCT CAGATCTCAG    60
AGAAGACAGC TCCATGTAGG CGGTATTCGT GGA                                 93
```

(2) INFORMATION FOR SEQ ID NO:18:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:18:

```
GCGCGCGGGC CCTTCGTTGA G                                              21
```

(2) INFORMATION FOR SEQ ID NO:19:

(i) SEQUENCE CHARACTERISTICS:
(A) LENGTH: 139 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:19:

```
Met Glu Trp Ser Trp Val Phe Leu Phe Phe Leu Ser Val Thr Thr Gly
 1               5                  10                  15
Val His Ser Gln Ile Gln Leu Val Gln Ser Gly Ala Glu Val Lys Lys
            20                  25                  30
Pro Gly Ser Ser Val Lys Val Ser Cys Lys Ala Ser Gly Tyr Thr Phe
        35                  40                  45
Thr Asp Tyr Tyr Ile Asn Trp Met Arg Gln Ala Pro Gly Gln Gly Leu
    50                  55                  60
Glu Trp Met Gly Trp Ile Asp Pro Gly Ser Gly Asn Thr Lys Tyr Asn
65                  70                  75                  80
Glu Lys Phe Lys Gly Arg Val Thr Ile Thr Val Asp Thr Ser Thr Asn
                85                  90                  95
Thr Ala Tyr Met Glu Leu Ser Ser Leu Arg Ser Glu Asp Thr Ala Phe
            100                 105                 110
Tyr Phe Cys Ala Arg Glu Lys Thr Thr Tyr Tyr Tyr Ala Met Asp Tyr
        115                 120                 125
Trp Gly Gln Gly Thr Leu Val Thr Val Ser Ser
    130                 135
```

(2) INFORMATION FOR SEQ ID NO:20:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:20:

```
GGACTGTTCG AAGCCGCCAC C                                              21
```

( 2 ) INFORMATION FOR SEQ ID NO:21:

( i ) SEQUENCE CHARACTERISTICS:
        ( A ) LENGTH: 81 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:21:

```
TGGCTTACAG  ATGCCAGATG  CGATATCCAG  ATGACTCAGA  GTCCAAGTAC  TCTCAGTGCC    60

AGTGTAGGTG  ATAGGGTCAC  C                                                 81
```

( 2 ) INFORMATION FOR SEQ ID NO:22:

( i ) SEQUENCE CHARACTERISTICS:
        ( A ) LENGTH: 90 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:22:

```
GGTGACACCT  TCCTCTATTG  GTTCCAGCAG  AAACCAGGTA  AAGCCCCAAA  GCTCCTCATG    60

TATAGGATGA  GTAACCTCGC  CAGTGGTGTA                                        90
```

( 2 ) INFORMATION FOR SEQ ID NO:23:

( i ) SEQUENCE CHARACTERISTICS:
        ( A ) LENGTH: 99 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:23:

```
CAGCCAGATG  ATTTCGCCAC  TTATTATTGT  ATGCAGCATC  TCGAATATCC  ATTCACTTTC    60

GGTCAGGGTA  CTAAAGTAGA  AGTAAAACGT  ACGGGCCGG                             99
```

( 2 ) INFORMATION FOR SEQ ID NO:24:

( i ) SEQUENCE CHARACTERISTICS:
        ( A ) LENGTH: 81 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:24:

```
GCATCTGGCA  TCTGTAAGCC  ACAGCAGCAG  GAGTCCGAGG  ACTTGGGTGG  GGACAGACAT    60

GGTGGCGGCT  TCGAACAGTC  C                                                 81
```

( 2 ) INFORMATION FOR SEQ ID NO:25:

( i ) SEQUENCE CHARACTERISTICS:
        ( A ) LENGTH: 81 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:25:

(2) INFORMATION FOR SEQ ID NO:26:

(i) SEQUENCE CHARACTERISTICS:
        (A) LENGTH: 102 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:26:

```
AGTGGCGAAA TCATCTGGCT GGAGACTACT GATAGTGAGA GTGAACTCAG TACCACTACC    60
ACTACCACTG AATCTAGATG GTACACCACT GGCGAGGTTA CT                      102
```

(2) INFORMATION FOR SEQ ID NO:27:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:27:

```
CCGGCCCGTA CGTTTTACTT C                                              21
```

(2) INFORMATION FOR SEQ ID NO:28:

(i) SEQUENCE CHARACTERISTICS:
        (A) LENGTH: 133 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:28:

```
Met Ser Val Pro Thr Gln Val Leu Gly Leu Leu Leu Leu Trp Leu Thr
 1               5                  10                  15
Asp Ala Arg Cys Asp Ile Gln Met Thr Gln Ser Pro Ser Thr Leu Ser
                20                  25                  30
Ala Ser Val Gly Asp Arg Val Thr Ile Thr Cys Arg Ser Ser Lys Ser
                35                  40                  45
Leu Leu His Ser Asn Gly Asp Thr Phe Leu Tyr Trp Phe Gln Gln Lys
 50                  55                  60
Pro Gly Lys Ala Pro Lys Leu Leu Met Tyr Arg Met Ser Asn Leu Ala
 65                  70                  75                  80
Ser Gly Val Pro Ser Arg Phe Ser Gly Ser Gly Ser Gly Thr Glu Phe
                85                  90                  95
Thr Leu Thr Ile Ser Ser Leu Gln Pro Asp Asp Phe Ala Thr Tyr Tyr
                100                 105                 110
Cys Met Gln His Leu Glu Tyr Pro Phe Thr Phe Gly Gln Gly Thr Lys
                115                 120                 125
Val Glu Val Lys Arg
                130
```

(2) INFORMATION FOR SEQ ID NO:29:

( i ) SEQUENCE CHARACTERISTICS:
( A ) LENGTH: 46 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:29:

GCGCGCAAGC TTGCCGCCAC CATGAAATGC AGCTGGGTCA TTTCTT    46

( 2 ) INFORMATION FOR SEQ ID NO:30:

( i ) SEQUENCE CHARACTERISTICS:
( A ) LENGTH: 44 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:30:

GCGCGCAAGC TTGCCGCCAC CATGGGATGG AGCTTATCAT TCTT    44

( 2 ) INFORMATION FOR SEQ ID NO:31:

( i ) SEQUENCE CHARACTERISTICS:
( A ) LENGTH: 46 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:31:

GCGCGCAAGC TTGCCGCCAC CATGAAGTGT GGTTAAACTG GGTTTT    46

( 2 ) INFORMATION FOR SEQ ID NO:32:

( i ) SEQUENCE CHARACTERISTICS:
( A ) LENGTH: 41 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:32:

GCGCGCAAGC TTGCCGCCAC CATGACTTTG GGTCAGCTTG T    41

( 2 ) INFORMATION FOR SEQ ID NO:33:

( i ) SEQUENCE CHARACTERISTICS:
( A ) LENGTH: 47 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:33:

GCGCGCAAGC TTGCCGCCAC CATGGACTCC AGGCTCAATT TAGTTTT    47

( 2 ) INFORMATION FOR SEQ ID NO:34:

( i ) SEQUENCE CHARACTERISTICS:
( A ) LENGTH: 43 base pairs
( B ) TYPE: nucleic acid
( C ) STRANDEDNESS: single
( D ) TOPOLOGY: linear (i i) MOLECULE TYPE: cDNA (x i) SEQUENCE DESCRIPTION: SEQ ID NO:34:

GCGCGCAAGC TTGCCGCCAC CATGGCTGTC TGGCTCTCTT CTG 43

(2) INFORMATION FOR SEQ ID NO:35:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:35:

GCGCGCAAGC TTGCCGCCAC CATGGATGGA GCGGTCTTTT CTT 43

(2) INFORMATION FOR SEQ ID NO:36:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:36:

GCGCGCAAGC TTGCCGCCAC CATGAGAGTG CTGATTCTTT TGTG 44

(2) INFORMATION FOR SEQ ID NO:37:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:37:

GCGCGCAAGC TTGCCGCCAC CATGGTTGGG TGTGGACTTG CTATT 45

(2) INFORMATION FOR SEQ ID NO:38:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:38:

GCGCGCAAGC TTGCCGCCAC CATGGGCAGA CTTACATTCT CATTCCT 47

(2) INFORMATION FOR SEQ ID NO:39:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:39:

GCGCGCAAGC TTGCCGCCAC CATGGATTTT GGGCTGATTT TTTTTATTG 49

( 2 ) INFORMATION FOR SEQ ID NO:40:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:40:

GCGCGCAAGC TTGCCGCCAC CATGATGGTG TTAAGTCTTC TGTACCT 47

( 2 ) INFORMATION FOR SEQ ID NO:41:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:41:

CAGATGGGCC CTTCGTTGAG GCTGGAGACG TGA 33

( 2 ) INFORMATION FOR SEQ ID NO:42:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:42:

GGACTGTTCG AAGCCGCCAC CATGAAGTTG CCTGTTAGGC TGTTGGTGCT 50

( 2 ) INFORMATION FOR SEQ ID NO:43:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:43:

GGACTGTTCG AAGCCGCCAC CATGGAGCAG ACACACTCCT GTATGGGT 48

( 2 ) INFORMATION FOR SEQ ID NO:44:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:44:

GGACTGTTCG AAGCCGCCAC CATGAGTGTG CTCACTCAGG TCCT 44

( 2 ) INFORMATION FOR SEQ ID NO:45:

( i ) SEQUENCE CHARACTERISTICS:
  ( A ) LENGTH: 44 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:45:

GGACTGTTCG AAGCCGCCAC CATGAGGCCC CTGCTCAGTT TTGG    44

( 2 ) INFORMATION FOR SEQ ID NO:46:

( i ) SEQUENCE CHARACTERISTICS:
    ( A ) LENGTH: 48 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:46:

GGACTGTTCG AAGCCGCCAC CATGGATTTC AGGTGCAGAT TTCAGCTT    48

( 2 ) INFORMATION FOR SEQ ID NO:47:

( i ) SEQUENCE CHARACTERISTICS:
    ( A ) LENGTH: 39 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:47:

GGACTGTTCG AAGCCGCCAC CATGAGGTCT GTAGTCTGG    39

( 2 ) INFORMATION FOR SEQ ID NO:48:

( i ) SEQUENCE CHARACTERISTICS:
    ( A ) LENGTH: 43 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:48:

GGACTGTTCG AAGCCGCCAC CATGGGCTCA AGATGGAGTC ACA    43

( 2 ) INFORMATION FOR SEQ ID NO:49:

( i ) SEQUENCE CHARACTERISTICS:
    ( A ) LENGTH: 45 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:49:

GGACTGTTCG AAGCCGCCAC CATGTGGGGA CTTTTCTTTT TCAAT    45

( 2 ) INFORMATION FOR SEQ ID NO:50:

( i ) SEQUENCE CHARACTERISTICS:
    ( A ) LENGTH: 42 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:50:

GGACTGTTCG AAGCCGCCAC CATGGTTCCC ACTCAGTTCC TT    42

( 2 ) INFORMATION FOR SEQ ID NO:51:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:51:

GGACTGTTCG AAGCCGCCAC CATGTATATA TGTTTGTTGT CTATTTC    47

( 2 ) INFORMATION FOR SEQ ID NO:52:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:52:

GGACTGTTCG AAGCCGCCAC CATGGAAGCC CCAGCTCAGC TTCTCTT    47

( 2 ) INFORMATION FOR SEQ ID NO:53:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:53:

GGATACAGTT GGTGCAGCAT CCGTACGTTT    30

( 2 ) INFORMATION FOR SEQ ID NO:54:

( i ) SEQUENCE CHARACTERISTICS:
        ( A ) LENGTH: 396 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..396

( x i ) SEQUENCE DESCRIPTION: SEQ ID NO:54:

```
ATG  GGC  ATC  AAG  ATG  GAG  TCA  CAG  ACC  CAG  GTC  TTT  GTA  TTC  GTG  TTG      48
Met  Gly  Ile  Lys  Met  Glu  Ser  Gln  Thr  Gln  Val  Phe  Val  Phe  Val  Leu
 1              5                        10                       15

CTC  TGG  TTG  TCT  GGT  GTT  GAT  GGA  GAC  ATT  GTG  ATG  ACC  CAG  TCT  CAA      96
Leu  Trp  Leu  Ser  Gly  Val  Asp  Gly  Asp  Ile  Val  Met  Thr  Gln  Ser  Gln
             20                       25                       30

AAA  TTC  ATG  TCC  ACA  TCA  GTA  GGA  GAC  AGG  GTC  AGC  ATC  ACC  TGC  AAG     144
Lys  Phe  Met  Ser  Thr  Ser  Val  Gly  Asp  Arg  Val  Ser  Ile  Thr  Cys  Lys
        35                       40                       45
```

| | | | | | | | | | | | | | | | | |
|---|---|---|---|---|---|---|---|---|---|---|---|---|---|---|---|---|
| GCC | AGT | CAG | AAT | GTT | CGT | ACT | GTT | GTA | GCC | TGG | TAT | CAA | CAG | AAA | CCA | 192 |
| Ala | Ser | Gln | Asn | Val | Arg | Thr | Val | Val | Ala | Trp | Tyr | Gln | Gln | Lys | Pro | |
| | 50 | | | | 55 | | | | | | | 60 | | | | |
| GGG | CAG | TCT | CCT | AAA | ACA | CTG | ATT | TAC | TTG | GCC | TCC | AAC | CGG | CAC | ACT | 240 |
| Gly | Gln | Ser | Pro | Lys | Thr | Leu | Ile | Tyr | Leu | Ala | Ser | Asn | Arg | His | Thr | |
| 65 | | | | | 70 | | | | | 75 | | | | | 80 | |
| GGA | GTC | CCT | GAT | CGC | TTC | ACA | GGC | AGT | GGA | TCT | GGG | ACA | GAT | TTC | ACT | 288 |
| Gly | Val | Pro | Asp | Arg | Phe | Thr | Gly | Ser | Gly | Ser | Gly | Thr | Asp | Phe | Thr | |
| | | | | 85 | | | | | 90 | | | | | 95 | | |
| CTC | ACC | ATT | AGC | AAT | GTG | CAA | TCT | GAA | GAC | CTG | GCA | GAT | TAT | TTC | TGT | 336 |
| Leu | Thr | Ile | Ser | Asn | Val | Gln | Ser | Glu | Asp | Leu | Ala | Asp | Tyr | Phe | Cys | |
| | | | 100 | | | | | 105 | | | | | 110 | | | |
| CTG | CAA | CAT | TGG | AGT | TAT | CCT | CTC | ACG | TTC | GGC | TCG | GGG | ACA | AAG | TTG | 384 |
| Leu | Gln | His | Trp | Ser | Tyr | Pro | Leu | Thr | Phe | Gly | Ser | Gly | Thr | Lys | Leu | |
| | | 115 | | | | | 120 | | | | | 125 | | | | |
| GAA | GTA | AAA | CGT | | | | | | | | | | | | | 396 |
| Glu | Val | Lys | Arg | | | | | | | | | | | | | |
| | | 130 | | | | | | | | | | | | | | |

(2) INFORMATION FOR SEQ ID NO:55:

(i) SEQUENCE CHARACTERISTICS:
        (A) LENGTH: 132 amino acids
        (B) TYPE: amino acid
        (D) TOPOLOGY: linear (ii) MOLECULE TYPE: protein (xi) SEQUENCE DESCRIPTION: SEQ ID NO:55:

| | | | | | | | | | | | | | | | |
|---|---|---|---|---|---|---|---|---|---|---|---|---|---|---|---|
| Met | Gly | Ile | Lys | Met | Glu | Ser | Gln | Thr | Gln | Val | Phe | Val | Phe | Val | Leu |
| 1 | | | | 5 | | | | | 10 | | | | | 15 | |
| Leu | Trp | Leu | Ser | Gly | Val | Asp | Gly | Asp | Ile | Val | Met | Thr | Gln | Ser | Gln |
| | | | 20 | | | | | 25 | | | | | 30 | | |
| Lys | Phe | Met | Ser | Thr | Ser | Val | Gly | Asp | Arg | Val | Ser | Ile | Thr | Cys | Lys |
| | | | 35 | | | | | 40 | | | | | 45 | | |
| Ala | Ser | Gln | Asn | Val | Arg | Thr | Val | Val | Ala | Trp | Tyr | Gln | Gln | Lys | Pro |
| | 50 | | | | 55 | | | | | | | 60 | | | |
| Gly | Gln | Ser | Pro | Lys | Thr | Leu | Ile | Tyr | Leu | Ala | Ser | Asn | Arg | His | Thr |
| 65 | | | | | 70 | | | | | 75 | | | | | 80 |
| Gly | Val | Pro | Asp | Arg | Phe | Thr | Gly | Ser | Gly | Ser | Gly | Thr | Asp | Phe | Thr |
| | | | | 85 | | | | | 90 | | | | | 95 | |
| Leu | Thr | Ile | Ser | Asn | Val | Gln | Ser | Glu | Asp | Leu | Ala | Asp | Tyr | Phe | Cys |
| | | | 100 | | | | | 105 | | | | | 110 | | |
| Leu | Gln | His | Trp | Ser | Tyr | Pro | Leu | Thr | Phe | Gly | Ser | Gly | Thr | Lys | Leu |
| | | 115 | | | | | 120 | | | | | 125 | | | |
| Glu | Val | Lys | Arg | | | | | | | | | | | | |
| | | 130 | | | | | | | | | | | | | |

(2) INFORMATION FOR SEQ ID NO:56:

(i) SEQUENCE CHARACTERISTICS:
        (A) LENGTH: 413 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 6..413

(xi) SEQUENCE DESCRIPTION: SEQ ID NO:56:

```
CCACC ATG AAC TTT GGG CTC AGC TTG GTT TTC CTT GTC CTA ATT TTA           47
      Met Asn Phe Gly Leu Ser Leu Val Phe Leu Val Leu Ile Leu
       1               5                    10

AAA GGT GTC CAG TGT GAA GTG AAG CTG GTG GAG TCT GGG GGA GGC TTA         95
Lys Gly Val Gln Cys Glu Val Lys Leu Val Glu Ser Gly Gly Gly Leu
 15              20                  25                      30

GTG AAG CCT GGA GGG TCC CTG AAA CTC TCC TGT GCA GCC TCT GGA TTC        143
Val Lys Pro Gly Gly Ser Leu Lys Leu Ser Cys Ala Ala Ser Gly Phe
                 35                  40                  45

GCT TTC AGT ACC TAT GAC ATG TCT TGG GTT CGC CAG ACT CCG GAG AAG        191
Ala Phe Ser Thr Tyr Asp Met Ser Trp Val Arg Gln Thr Pro Glu Lys
             50                  55                  60

AGG CTG GAG TGG GTC GCA ACC ATT AGT AGT GGT GGT AGT TAC ACC TAC        239
Arg Leu Glu Trp Val Ala Thr Ile Ser Ser Gly Gly Ser Tyr Thr Tyr
         65                  70                  75

TAT TTA GAC AGT GTG AAG GGC CGA TTC ACC ATC TCC AGA GAC AGT CCC        287
Tyr Leu Asp Ser Val Lys Gly Arg Phe Thr Ile Ser Arg Asp Ser Pro
     80                  85                  90

AGG AAC ACC CTA TAC CTG CAA ATG AGC AGT CTG AGG TCT GAG GAC ACG        335
Arg Asn Thr Leu Tyr Leu Gln Met Ser Ser Leu Arg Ser Glu Asp Thr
 95                 100                 105                 110

GCC TTG TAT TAC TGT GCA CCG ACT ACG GTA GTC CCG TTT GCT TAC TGG        383
Ala Leu Tyr Tyr Cys Ala Pro Thr Thr Val Val Pro Phe Ala Tyr Trp
                115                 120                 125

GGC CAA GGG ACT CTG GTC ACC GTC TCT GCA                                413
Gly Gln Gly Thr Leu Val Thr Val Ser Ala
             130                 135
```

( 2 ) INFORMATION FOR SEQ ID NO:57:

( i ) SEQUENCE CHARACTERISTICS:
        ( A ) LENGTH: 136 amino acids
        ( B ) TYPE: amino acid
        ( D ) TOPOLOGY: linear ( i i ) MOLECULE TYPE: protein ( x i ) SEQUENCE DESCRIPTION: SEQ ID NO:57:

```
Met Asn Phe Gly Leu Ser Leu Val Phe Leu Val Leu Ile Leu Lys Gly
 1               5                  10                  15

Val Gln Cys Glu Val Lys Leu Val Glu Ser Gly Gly Gly Leu Val Lys
             20                  25                  30

Pro Gly Gly Ser Leu Lys Leu Ser Cys Ala Ala Ser Gly Phe Ala Phe
             35                  40                  45

Ser Thr Tyr Asp Met Ser Trp Val Arg Gln Thr Pro Glu Lys Arg Leu
         50                  55                  60

Glu Trp Val Ala Thr Ile Ser Ser Gly Gly Ser Tyr Thr Tyr Tyr Leu
 65                  70                  75                  80

Asp Ser Val Lys Gly Arg Phe Thr Ile Ser Arg Asp Ser Pro Arg Asn
                 85                  90                  95

Thr Leu Tyr Leu Gln Met Ser Ser Leu Arg Ser Glu Asp Thr Ala Leu
            100                 105                 110

Tyr Tyr Cys Ala Pro Thr Thr Val Val Pro Phe Ala Tyr Trp Gly Gln
        115                 120                 125

Gly Thr Leu Val Thr Val Ser Ala
        130                 135
```

( 2 ) INFORMATION FOR SEQ ID NO:58:

( i ) SEQUENCE CHARACTERISTICS:

(A) LENGTH: 24 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:58:

GCGGGACTGT TCGAAGCCGC CACC 24

(2) INFORMATION FOR SEQ ID NO:59:

(i) SEQUENCE CHARACTERISTICS:
(A) LENGTH: 81 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:59:

CCTGACAAGC TTCGGCGGTG GTACAGACAG GGGTGGGTTC AGGAGCCTGA GGACGACGAC 60

ACCGAATGTC TACGGTCTAC A 81

(2) INFORMATION FOR SEQ ID NO:60:

(i) SEQUENCE CHARACTERISTICS:
(A) LENGTH: 81 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:60:

TGGCTTACAG ATGCCAGATG TGATATCCAG ATGACTCAGA GTCCAAGTAG TCTCAGTGTA 60

AGTGTAGGTG ATAGGGTAAC T 81

(2) INFORMATION FOR SEQ ID NO:61:

(i) SEQUENCE CHARACTERISTICS:
(A) LENGTH: 90 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:61:

TCACATCCAC TATCCCATTG ATAGTGAACA TTCCGGTCAG TCTTACAAGC ATGACAACAT 60

CGGACCATAG TCGTCTTTGG TCCAGAGCGG 90

(2) INFORMATION FOR SEQ ID NO:62:

(i) SEQUENCE CHARACTERISTICS:
(A) LENGTH: 93 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:62:

CAGCAGAAAC CAGGTCTCGC CCCAAAAACT CTCATCTATT TGGCCTCCAA CCGGCACACT 60

GGAGTACCAT CTAGATTCAG TGGTAGCGGT AGT 93

( 2 ) INFORMATION FOR SEQ ID NO:63:

( i ) SEQUENCE CHARACTERISTICS:
          ( A ) LENGTH: 87 base pairs
          ( B ) TYPE: nucleic acid
          ( C ) STRANDEDNESS: single
          ( D ) TOPOLOGY: linear ( i i ) MOLECULE TYPE: cDNA ( x i ) SEQUENCE DESCRIPTION: SEQ ID NO:63:

```
TCTAAGTCAC  CATCGCCATC  ACCATGACTA  AAGTGAAAGT  GATAGTCATC  AGAGGTCGGT        60
CTTCTATAGC  GGTGAATGAA  GACGGAC                                               87
```

( 2 ) INFORMATION FOR SEQ ID NO:64:

( i ) SEQUENCE CHARACTERISTICS:
          ( A ) LENGTH: 90 base pairs
          ( B ) TYPE: nucleic acid
          ( C ) STRANDEDNESS: single
          ( D ) TOPOLOGY: linear ( i i ) MOLECULE TYPE: cDNA ( x i ) SEQUENCE DESCRIPTION: SEQ ID NO:64:

```
GATATCGCCA  CTTACTTCTG  CCTGCAACAT  TGGAGTTATC  CTCTCACGTT  CGGTCAGGGT        60
ACTAAAGTAG  AAGTAAAACG  TACGGGCCGG                                            90
```

( 2 ) INFORMATION FOR SEQ ID NO:65:

( i ) SEQUENCE CHARACTERISTICS:
          ( A ) LENGTH: 21 base pairs
          ( B ) TYPE: nucleic acid
          ( C ) STRANDEDNESS: single
          ( D ) TOPOLOGY: linear ( i i ) MOLECULE TYPE: cDNA ( x i ) SEQUENCE DESCRIPTION: SEQ ID NO:65:

```
CTTCATTTTG  CATGCCCGGC  C                                                     21
```

( 2 ) INFORMATION FOR SEQ ID NO:66:

( i ) SEQUENCE CHARACTERISTICS:
          ( A ) LENGTH: 21 base pairs
          ( B ) TYPE: nucleic acid
          ( C ) STRANDEDNESS: single
          ( D ) TOPOLOGY: linear ( i i ) MOLECULE TYPE: cDNA ( x i ) SEQUENCE DESCRIPTION: SEQ ID NO:66:

```
GCGCGCAAGC  TTGCCGCCAC  C                                                     21
```

( 2 ) INFORMATION FOR SEQ ID NO:67:

( i ) SEQUENCE CHARACTERISTICS:
          ( A ) LENGTH: 90 base pairs
          ( B ) TYPE: nucleic acid
          ( C ) STRANDEDNESS: single
          ( D ) TOPOLOGY: linear ( i i ) MOLECULE TYPE: cDNA ( x i ) SEQUENCE DESCRIPTION: SEQ ID NO:67:

```
CGCGCGTTCG  AACGGCGGTG  GTACCTTACC  TCGACCCAGA  AAGAGAAGAA  GGACAGTCAT        60
TGATGTCCTC  AGGTAAGACT  CCACGTCGAC                                            90
```

(2) INFORMATION FOR SEQ ID NO:68:

(i) SEQUENCE CHARACTERISTICS:
        (A) LENGTH: 96 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:68:

```
GTCCATTCTG AGGTGCAGCT GCTGGAGTCT GGAGGAGGAC TGGTGCAGCC TGGAGGATCT    60
CTGAGACTGT CTTGTGCAGC ATCTGGATTC GCTTTC                              96
```

(2) INFORMATION FOR SEQ ID NO:69:

(i) SEQUENCE CHARACTERISTICS:
        (A) LENGTH: 96 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:69:

```
CGTCGTAGAC CTAAGCGAAA GTCATGGATA CTGTCAAGAA CCCACTCTGT CCGTGGACCT    60
TTTCCTGAGC TCACCCACCG TTGGTAATCA TCACCA                              96
```

(2) INFORMATION FOR SEQ ID NO:70:

(i) SEQUENCE CHARACTERISTICS:
        (A) LENGTH: 90 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:70:

```
GTGGCAACCA TTAGTAGTGG TGGTAGTTAC ACCTACTATT TAGACAGTGT GAAGGGAAGA    60
TTCACAATTT CCAGAGACTC TAGCAAGAAT                                     90
```

(2) INFORMATION FOR SEQ ID NO:71:

(i) SEQUENCE CHARACTERISTICS:
        (A) LENGTH: 96 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:71:

```
AGGTCTCTGA GATCGTTCTT ATGTGACATG GACGTCTACT TAAGAGACGT CCGTCTCCTG    60
AGACGTTAAA TGATGACACG TGGCTGATGC CATCAG                              96
```

(2) INFORMATION FOR SEQ ID NO:72:

(i) SEQUENCE CHARACTERISTICS:
        (A) LENGTH: 89 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:72:

```
TGTGCACCGA  CTACGGTAGT  CCCGTTTGCT  TACTGGGGAC  AGGGAACACT  GGTGACAGTG         60

TCTTCTGCCT  CAACGAAGGG  CCCGCGCGC                                              89
```

( 2 ) INFORMATION FOR SEQ ID NO:73:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:73:

```
GAGTTGCTTC  CCGGGCGCGC  G                                                      21
```